US007041870B2

(12) United States Patent
Tomizuka et al.

(10) Patent No.: US 7,041,870 B2
(45) Date of Patent: May 9, 2006

(54) TRANSGENIC TRANSCHROMOSOMAL RODENTS FOR MAKING HUMAN ANTIBODIES

(75) Inventors: Kazuma Tomizuka, Takasaki (JP); Isao Ishida, Kanagawa (JP); Nils Lonberg, Woodside, CA (US); Edward L. Halk, Sunnyvale, CA (US)

(73) Assignees: Medarex, Inc., Princeton, NJ (US); Kirin Brewery Company Limited, Tokyo (JP)

(*) Notice: Subject to any disclaimer, the term of this patent is extended or adjusted under 35 U.S.C. 154(b) by 210 days.

(21) Appl. No.: 10/000,433

(22) Filed: Nov. 30, 2001

(65) Prior Publication Data

US 2002/0199213 A1 Dec. 26, 2002

Related U.S. Application Data

(60) Provisional application No. 60/250,340, filed on Nov. 30, 2000.

(51) Int. Cl.
*A01K 67/00* (2006.01)
*A01K 67/027* (2006.01)
*C12N 15/00* (2006.01)

(52) U.S. Cl. ............................ 800/13; 800/14; 800/15; 800/16; 800/17; 800/18; 800/19; 800/20; 800/21; 800/22; 800/23; 800/24; 800/25

(58) Field of Classification Search ............. 800/13–25
See application file for complete search history.

(56) References Cited

U.S. PATENT DOCUMENTS

| | | | | |
|---|---|---|---|---|
| 5,175,384 | A | 12/1992 | Krimpenfort | |
| 5,204,244 | A | 4/1993 | Fell et al. | |
| 5,416,260 | A | 5/1995 | Koller | |
| 5,434,340 | A | 7/1995 | Krimpenfort | |
| 5,545,806 | A | 8/1996 | Lonberg et al. | |
| 5,545,807 | A | 8/1996 | Surani | |
| 5,569,825 | A | 10/1996 | Lonberg et al. | |
| 5,625,126 | A | 4/1997 | Lonberg et al. | |
| 5,633,425 | A | 5/1997 | Lonberg et al. | |
| 5,661,016 | A | 8/1997 | Lonberg et al. | |
| 5,698,196 | A | 12/1997 | Matsushima | |
| 5,702,946 | A | 12/1997 | Doerschuk | |
| 5,770,429 | A | 6/1998 | Lonberg et al. | |
| 5,789,650 | A | 8/1998 | Lonberg et al. | |
| 5,814,318 | A | 9/1998 | Lonberg et al. | |
| 5,874,299 | A | 2/1999 | Lonberg et al. | |
| 5,877,397 | A | 3/1999 | Lonberg et al. | |
| 5,939,598 | A | 8/1999 | Kucherlapati et al. | |
| 6,162,963 | A * | 12/2000 | Kucherlapati et al. | 800/18 |
| 6,300,129 | B1 | 10/2001 | Lonberg et al. | |
| 6,632,976 | B1 * | 10/2003 | Tomizuka et al. | 800/18 |
| 2003/0093820 | A1 * | 5/2003 | Green et al. | 800/8 |

FOREIGN PATENT DOCUMENTS

| | | |
|---|---|---|
| EP | 0 315 062 | 5/1989 |
| EP | 0 773 288 | 5/1997 |
| EP | 0 843 961 | 5/1998 |
| EP | 0 972 445 | 1/2000 |
| EP | 1 106 061 | 6/2000 |
| EP | 1 206 906 | 5/2002 |
| WO | WO 90/04036 | 4/1990 |
| WO | WO 90/12878 | 11/1990 |
| WO | WO 91/00906 | 1/1991 |
| WO | WO 91/10741 | 7/1991 |
| WO | WO 92/03918 | 3/1992 |
| WO | WO 96/02576 | 2/1996 |
| WO | WO 02/43478 | 6/2002 |

OTHER PUBLICATIONS

Houdebine, (1994) J. Biotech. 34, p. 281.*
Linder, Lab Animal May 2001;30:34-9.*
Logan and Sharma, Clin Exp Pharmacol Physiol Dec. 1999; 26:1020-25.*
Hammer et al, J Anim Sci 1986;63:269-78.*
Mullins et al, J Clin Invest Apr. 1996;97:1557-60.*
Wall et al, J Dairy Sci 1997;80:2213-24.*
Sigmund, Arteroscler. Throm. Vasc. Biol. 2000;20:1425-9.*
Niemann, Transg. Res. 1998, 7, p. 73-.*
Donovan and Gearhart, Nat Nov. 2001;414:92-97.*
Denning et al, Nat Biotech 2001;19:559-562.*
Nielsen et al, J Cell Biochem. Jan. 2000;76(4):674-85.*
Tomizuka et al, Nat Genetics 1997;16:133-43.*
Bonneville, M., et al., "Blockage of αβ T-cell development by TCR γδ transgenes," *Nature* 342(6252):931-934 (Dec. 1989).
Bonneville, M., et al., "Self-tolerance to transgenic γδ T cells by intrathymic inactivation," *Nature* 344(6262):163-165 (Mar. 1990).
Bonneville, M., et al., "Transgenic Mice Demonstrate that Epithelial Homing of γ/δ T cells is determined by cell lineages independent of T cell receptor specificity," *J. Exp. Med.* 171(4):1015-1026 (Apr. 1990).
Ishida, I., et al., "Expression and characterization of hydroxyindole O-methyltransferase from a cloned cDNA in Chinese hamster ovary cells," *Molecular Brain Res.* 388(3): 185-189 (Sep. 1987).
Ishida, I., et al., "Production of a diverse repertoire of human antibodies in genetically engineered mice," *Microbiol. Immunol.* 42(3):143-150 (1998).
Ishida, I., et al., "Production of anti-virus, viroid plants by genetic manipulations," *Pest Manag. Sci.* 58(11):1132-1136 (Nov. 2002).

(Continued)

*Primary Examiner*—Q. Janice Li
(74) *Attorney, Agent, or Firm*—Darby & Darby P.C.

(57) ABSTRACT

The present invention provides novel transgenic nonhuman mammals capable of producing human sequence antibodies, as well as methods of producing and using these antibodies.

4 Claims, 14 Drawing Sheets

OTHER PUBLICATIONS

Ishida, I., et al., "Production of human monoclonal and polyclonal antibodies in TransChromo animals," *Cloning Stem Cells* 4(1):91-102(2002).
Ishida, I., et al., "T-cell receptor γδ and γ transgenic mice suggest a role of a γ gene silencer in the generation of αβ T cells," *Proc. Natl. Acad. Sci. USA* 87(8):3067-3071 (Apr. 1990).
Ishida, I., et al., "TransChromo Mouse," *Biotechnol. Genet. Eng. Rev*. 19:73-82 (Nov. 2002).
Alt, F.W., et al., "Immunoglobulin genes in transgenic mice", *Trends in Genetics*, 231-236, (Aug. 1985).
Berman, J.E., et. al., "Content and organization of the human lg $V_H$ locus: definition of three new $V_H$ families and linkage to the lg $C_H$ locus", *The EMBO J*. 7:727-738 (1988).
Berton, M.T., et. al., "Synthesis of germ-line .γ1 immunoglobulin heavy-chain transcripts in resting B cells: Induction by interleukin 4 and inhibition by interferon γ.", *Proc. Natl. Acad. Sci*. (*U.S.A.*) 86:2829-2833 (1989).
Bollag, R.J., et al., "Homologous recombination in mammalian cells", *Annu. Rev. Genet*. 23:199-225 (1989).
Bruggemann, M., et al., "A repertoire of monoclonal antibodies with human heavy chains from transgenic mice", *Proc. Natl. Acad. Sci. USA* 86:6709-6713 (1989).
Bruggemann, M., et al., "Human antibody production in transgenic mice: expression from 100 kb of the human IgH locus", *Eur. J. Immunol*. 21:1323-1326 (1991).
Bucchini, D., et al., "Rearrangement of a chicken immunoglobulin gene occurs in the lymphoid lineage of transgenic mice", *Nature* 326:409-411 (1987).
Buttin, G.,, "Exogenous lg gene rearrangement in transgenic mice: a new strategy for human monoclonal antibody production?" *Trends in Genetics*—vol. 3, No. 8, 205-206 (Aug. 1987).
Capecchi, M.R., "Altering the genome by homologous recombination", *Science* 244:1288-1292 (1989).
Capecchi, M.R., "The new mouse genetics: Altering the genome by gene targeting", *Trends in Genetics* 5:70-76 (1989).
Choi, T.K., et al., "Transgenic mice containing a human heavy chain immunoglobulin gene fragment cloned in a yeast artificial chromosome." *Nat Genet*. Jun. 1993;4(2): 117-23.
Coffman, R.L., et al., "A mouse T cell product that preferentially enhances IgA production", *J. Immunol*. 139: 3685-3690 (1987).
Coffman, R.L., and Carty, J, "A T cell activity that enhances polyclonal IgE production and its inhibition by interferon-γ", *J. Immunol*. 136:949-954 (1986).
Davies, N.P., et al., "Creation of Mice Expressing Human Atibody Light Chains by Introduction of a Yeast Artificial Chromosome Containing the Core Region of the Human Immunoglobulin κ Locus." *Biotechnology* (N Y). Aug. 1993;11(8):911-4.
Davies, N.P., et al., "Targeted Alterations in Yeast Artificial Chromosomes for Inter-Species Gene Transfer", *Nucleic Acid Res*. 20: 2693-2698 (1992).
Doetschman, T., et al., "Targetted correction of a mutant HPRT gene in mouse embryonic stem cells", *Nature* 330: 576-578 (1987).
Durdik, J., et al., "Isotype switching by a microinjected μ immunoglobulin heavy chain gene in transgenic mice", *Proc. Natl. Acad. Sci. USA* 86:2346-2350 (1989).
Esser, C., and Radbruch, A., "Rapid induction of transcription of unrearranged Sγ1 switch regions in activated murine B cells by interleukin 4", *The EMBO J*. 8:483-488 (1989).
Ferrier, P., et al., "Separate elements control DJ and VDJ rearrangement in a transgenic recombination substrate", *The EMBO J*. 9:117-125 (1990).
Fishwild, D.M., et al. "High-Avidity human IgGx monoclonal antibodies from a novel strain of minilocus transgenic mice", *Nature Biotechnology* 14:845. (1996).
Forni, L., "Extensive splenic B cell activation in IgM-transgenic mice", *Eur. J. Immunol*. 20:983-989 (1990).
Gerstein, R.M., et al., "Isotype Switching of an Immunoglobulin Heavy Chain Transgene Occurs by DNA Recombination between Different Chromosomes", *Cell* 63: 537-548 (1990).
Goodhardt, M., et al., "Rearrangement and expression of rabbit immunoglobulin κ light chain gene in transgenic mice", *Proc. Natl. Acad. Sci*. (*U.S.A.*) 84:4229-4233 (1987).
Gordon, J., "Transgenic mice in immunology", *The Mount Sinai Journal of Medicine*, 53:223-231 (1986).
Green, L.L., et al., "Antigen-specific human monoclonal antibodies from mice engineered with human lg heavy and light chain YACs", *Nature Genetics* 7:13-21 (1994).
Hagman, J., et al., "Inhibition of immunoglobulin gene rearrangement by the expression of a .λ2 transgene", *J. Exp. Med*. 169:1911-1929 (1989).
Hofker, M.H., et al., "Complete physical map of the human immunoglobulin heavy chain constant region gene complex", *Proc. Natl. Acad. Sci. USA* 86:5567-5571 (1989).
Humphries, C.G., et al., "A new human immunoglobulin $V_H$ family preferentially rearranged in immature B-cell tumours", *Nature* 331:446-449 (1988).
Huxley, C., et al., "The human HPRT gene on a yeast artificial chromosome is functional when transferred to mouse cells by cell fusion." *Genomics* Apr. 1999;9(4):742-50.
Ichihara, Y., et al., "Organization of human immunoglobulin heavy chain diversity gene loci", *The EMBO J*. 7:4141-4150 (1988).
Iglesias, A., et al., "Expression of immunoglobulin delta chain causes allelic exclusion in transgenic mice", *Nature* 330:482-484 (1987).
Jaenisch, R., "Transgenic Animals", *Science* 240:1468-1474 (1988).
Jakobovits, A., et al., "Analysis of homozygous mutant chimeric mice: Deletion of the immunoglobulin heavy-chain joining region blocks B-cell development and antibody production", *Proc. Natl. Acad. Sci. USA* 90:2551-2555 (1993).
James, K., and Bell, G.T., "Human monoclonal antibody production current status and future prospects", *J. of Immunol. Methods* 100:5-40 (1987).
Jasin, M., and Berg, P., "Homologous integration in mammalian cells without target gene selection", *Genes & Development* 2:1353-1363 (1988).
Jung, S., et al., "Shutdown of Class Switching Recombination by Deletion of a Switch Region Control Element", *Science* 259:984-987 (1993).
Kenny, J.J., et al., "Alteration of the B cell surface phenotype, immune response to phosphocholine and the B cell repertoire in M167 .μ plus κ transgenic mice", *J. of Immunol*. 142:4466-4474 (1989).
Kitamura, D., et al., "A B cell-deficient mouse by targeted disruption of the membrane exon of the immunoglobulin .μ chain gene", *Nature* 350:423-426 (1991).

Koller, B.H., and Smithies, O., "Inactivating the $\beta_2$-microglobulin locus in mouse embryonic stem cells by homologous recombination", *Proc. Natl. Acad. Sci. USA* 86:8932-8935 (1989).
Lin, F.L., et al., "Recombination in mouse L cells between DNA introduced into cells and homologous chromosomal sequences", *Proc. Natl. Acad. Sci. USA* 82:1391-1395 (1985).
Linton, P.-J., et al., "Primary Antibody-Forming Cells and Secondary B Cells Are Generated from Separate Precursor Cell Subpopulations", *Cell* 59:1049-1059 (1989).
Lo, D., et al., "Expression of mouse IgA by transgenic mice, pigs and sheep", *Eur. J. Immunol*. 21:1001-1006 (1991).
Lonberg, M., et al., "Antigen-specific human antibodies from mice comprising four distinct genetic modifications", *Nature* 368:856-859 (1994).
Lorenz, W., et al., "Physical map of the human immunoglobulin .κ locus and its implications for the mechanisms of $V_\kappa$ -$J_\kappa$ rearrangement", *Nucl. Acids Res*. 15:9667-9676 (1987).
Lutzker, S., and Alt, F.W., "Structure and Expression of Germ Line Immunoglobulin .γ2b Transcripts", *Mol. Cell Biol*. 8:1849-1852 (1988).
Mansour, S.L., et al., "Disruption of the proto-oncogene *int*-2 in mouse embryo-derived stem cells: a general strategy for targeting mutations to non-selectable genes", *Nature* 336:348-352 (1988).
Miller, J., et al., "Structural alterations in J regions of mouse immunoglobulin λ genes are associated with differential gene expression", *Nature* 295:428-430 (1982).
Mills, F.C., et al., "DNase I hypersensitive sites in the chromatin of human μ immunoglobulin heavy-chain genes", *Nature* 306:809-812 (1983).
Mills, F.C., et al., "Sequences of human immunoglobulin switch regions: implications for recombination and transcription", *Nucl. Acids. Res*. 18:7305-7316 (1991).
Morrison, S.L., "Success in specification", *Nature* 368:812-813 (1994).
Mowatt, M.R., et al., "DNA sequence of the murine .γ1 switch segment reveals novel structural elements", *J. Immunol*. 136:2674-2683 (1986).
Müller, W., et al., "Membrane-bound IgM obstructs B cell development in transgenic mice", *Eur. J. Immunol*. 19:923-928 (1989).
Murray, A.W., and Szostak, J.W., "Construction of artificial chromosomes in yeast", *Nature* 305:189-193 (1983).
Nikaido, T., et al., "Nucleotide Sequences of Switch Regions of Immunoglobulin C and C Genes and Their Comparison", *J. Biol. Chem*. 257:7322-7239 (1982).
Nikaido, T., et al., "Switch region of immunoglobulin Cμ gene is composed of simple tandem repetitive sequences", *Nature* 292:845-848 (1981).
Neuberger, M.S., et al., "Isotype exclusion and transgene down-regulation in immunoglobulin-λ transgenic mice", *Nature* 338:350-352 (1989).
Neuberger, M.S., "Generating high-avidity human Mabs in mice", *Nature Biotechnology* 14:826 (1996).
Nussenzweig, M.C., et al., "Allelic exclusion in transgenic mice carrying mutant human IgM genes", *J. Exp. Med*. 167:1969 (1988).
Kazuki, Y., et al., "Germline transmission of a transferred human chromosome 21 fragment in transchromosomal mice," *J. Hum. Genet*. 46(10):600-603 (2001).
Kuroiwa, Y., et al., "Cloned transchromosomic calves producing human immunoglobulin," *Nat. Biotechnol*. 20(9): 889-894 (Sep. 2002).
Kuroiwa, Y., et al., "Efficient modification of a human chromosome by telomere-directed truncation in high homologous recombination-proficient chicken DT40 cells," *Nucleic Acid Res*. 26(14):3447-3448 (Jul. 1998).
Kuroiwa, Y., et al., "Manipulation of human minichromosomes to carry greater than megabase-sized chromosome inserts," *Nat. Biotechnol*. 18(10):1086-1090 (Oct. 2000).
Kuroiwa, Y., et al., "The use of chromosome-based vectors for animal transgenesis," *Gene Ther*. 9(11):708-712 (Jun. 2002).
Robl, J.M., et al., "Artificial chromosome vectors and expression of complex proteins in transgenic animals," *Theriogenology* 59:107-113 (2003).
Sano, T., et al., "Transgenic potato expressing a double-stranded RNA-specific ribonulcease is resistant to potato spindle tuber viroid," *Nat. Biotechnol*. 15(12):1290-1294 (Nov. 1997).
Shinohara, T., et al., "Stability of transferred human chromosome fragments in cultured cells and in mice," *Chromosome Res*. 8(8):713-725 (2000).
Von Boehmer, et al., "Early expression of a T-cell receptor β-chain transgene suppresses rearrangement of the Vγ4 gene segment," *Proc. Natl. Acad. Sci. USA* 85(24):9729-9732 (Dec. 1988).
Nussenzweig, M.C., et al., "A human immunoglobulin gene reduces the incidence of lymphomas in c-*Myc*-bearing transgenic mice", *Nature* 336:446-450 (1988).
Oettinger, M.A., et al., "RAG-1 and RAG-2, Adjacent Genes That Synergistically Activate V(D)J Recombination", *Science* 248:1517-1523 (1990).
Petters, R.M., "Transgenic mice in immunological research", *Vet. Immunol. Immunopath*. 17:267-278 (1987).
Pettersson, S., et al., "A Second B cell-specific enhancer 3' of the immunoglobulin heavy-chain locus", *Nature* 344:165-168 (1990).
Rabbitts, T.H., et. al., "Human immunoglobulin heavy chain genes: evolutionary comparisons of Cμ, Cδ and Cγ genes and associated switch sequences", *Nucl. Acids Res*. 9:4509-4524 (1981).
Rath, S., et al., "B cell abnormalities induced by a μ Ig transgene extend to L chain isotype usage", *J. of Immunol*. 146:2841 (1991).
Rath, S., et al., "Quantitative analysis of idiotypic mimicry and allelic exclusion in mice with a μ lg Transgene", *J. of Immunol*. 143:2074-2080 (1989).
Ravetch, J.V., et al., "Evolutionary approach to the question of immunoglobulin heavy chain switching: Evidence from cloned human and mouse genes", *Proc. Natl. Acad. Sci*. (*U.S.A*.) 77:6734-6738 (1980).
Reid, L.E., et al., "A single DNA response element can confer inducibility by both α- and γ-interferons", *Proc. Natl. Acad. Sci*. (*U.S.A*.) 86:840-844 (1989).
Ritchie, K.A., et al., "Allelic exclusion and control of endogenous immunoglobulin gene rearrangement in κ transgenic mice", *Nature* 312:517-520 (1984).
Rothman, P., et al., "Structure and expression of germline immunoglobulin γ3 heavy chain gene transcripts: implications for mitogen and lymphokine directed class-switching", *Intl. Immunol*. 2:621-627 (1990).

Rusconi, S., et al., "Transmission and expression of a specific pair of rearranged immunoglobulin μ and κ genes in a transgenic mouse line", *Nature* 314:330-334 (1985).
Sato, T., et al., "Physical linkage of a variable region segment and the joining region segment of the human immunoglobulin heavy chain locus", *Biochem. Biophys. Res. Comm.* 154:264-271 (1988).
Scangos, G., and Bieberich, C., "Gene transfer into mice", *Advances in Genetics* 24: 285-322 (1987).
Sevidy, J.M., and Sharp, P.A., "Positive genetic selection for gene disruption in mammalian cells by homologous recombination", *Proc. Natl. Acad. Sci. USA* 86:227-231 (1989).
Shimizu, A., et al., "Immunoglobulin double-isotype expression by trans-mRNA in a human immunoglobulin transgenic mouse", *Proc. Natl. Acad. Sci. USA* 86:8020-8023 (1989).
Shimizu, A., et al., "Trans-Splicing as a Possible Molecular Mechanism for the Multiple Isotype Expression of the Immunoglobulin Gene", *J. Exp. Med.* 173:1385-1393 (1991).
Shin, E. K., et al., "Physical Map of the 3' Region of the Human Immunoglobulin Heavy Chain Locus: Clustering of Autoanitobyd-realted Variable Segments in One Haplotype", *The EMBO J.* : 10, 3641-3645 (1991).
Sideras, P., et al., "Production of sterile transcripts by Cγ genes in an IgM-producing human neoplastic B cell line that switches to IgG-producing cells", *Intl. Immunol.* 1: 631-642 (1989).
Siebenlist, U., et al., "Human immunoglobulin D segments encoded in tandem multigenic families", *Nature* 294:631-635 (1981).
Smithies, O., et al., "Insertion of DNA sequences into the human chromosomal β-globin locus by homologous recombination", *Nature* 317:230-234 (1985).
Snapper, C.M., and Paul, W.E., "Interferon-γ and B Cell Stimulatory Factor-1 Reciprocally Regulate lg Isotype Production", *Science* 236:944-947 (1987).
Song, K.-Y., et al., "Accurate modification of a chromosomal plasmid by homologous recombination in human cells", *Proc. Natl. Acad. Sci. USA* 84:6820-6824 (1987).
Stavnezer, J., et al., "Immunoglobulin heavy-chain switching may be directed by prior induction of transcripts from constant-region genes", *Proc. Natl. Acad. Sci.* (*U.S.A.*) 85: 7704-7708 (1988).
Storb, U., et al., "Expression, Allelic Exclusion and Somatic Mutation of Mouse Immunoglobulin Kappa Genes", *Immunological Reviews* 89:85-102 (1986).
Storb, U., Immunoglobulin Gene Analysis in Transgenic Mice, in *Immunoglobulin Genes*, Academic Press Limited, pp. 303-326 (1989).
Szurek, P., et al., "Complete nucleotide sequence of the murine γ3 switch region and analysis of switch recombination in two γ3-expressing hybridomas", *J. Immunol.* 135: 620-626 (1985).
Tahara, T., et al., "HLA antibody responses in HLA class I transgenic mice", *Immunogenetics* 32:351-360 (1990).
Takai, T., et al., "Augmented Humoral and Anaphylactic Responses in FcγRII-deficient Mice", Nature 379:346-349 (1996).
Taki, S., et al., "Targeted Insertion of a Variable Region Gene into the Immunoglobulin Heavy Chain Locus", *Science* 262:1268-1271 (1993).
Tanaka, T., et al., "An Antisense Oligonucleotide Complementary to a Sequence in Iγ2b Increase γ2b Germline Transcrips, Stimulates B cell DNA Synthesis, and Inhibits Immunoglobulin Secretion", *The Journal of Experimental Medicine* 175:597-607 (1992).
Taussig, M.J., et al., "Regulation of immunoglobulin gene rearrangement and expression", *Immunology Today* 10:143-146 (1989).
Taylor, L.D., et al., "Human immunoglobulin transgenes undergo rearrangement, somatic mutation and class switching in mice that lack endogenous IgM", *International Immunology* 6:579-591 (1994).
Thomas, K.R., and Capecchi, M.R., "Site-Directed Mutagenesis by Gene Targeting in Mouse Embryo-Derived Stem Cells", *Cell* 51:503-512 (1987).
Thomas, K.R., et al., "High Frequency Targeting of Genes to Specific Sites in the Mammalian Genome", *Cell* 44:419-428 (1986).
Tomizuka, K., et al., "Double Trans-Chromosmic Mice: Maintenance of Two Individual Human Chromosome Fragments Containing lg Heavy and Kappa Loci and Expression of Fully Human Antibodies," *Proc. Nat. Acad. Sci* (*USA*) 97:722-727 (2000).
Uhlmann, E., and Peyman, A., "Antisense Oligonucleotides: A new therapeutic principle," *Chemical Reviews* 90:544-584 (1990).
Vlasov, et al., "Arrest of immunoglobulin G mRNA translation in vitro with an alkylating antisense oligonucleotide derivative", *Chemical Abstracts*, p. 28, 112:229433X (1990).
Wagner, S.D., et al., "Antibodies generated from human immunoglobulin miniloci in transgenic mice." *Nucleic Acids Res*. Apr. 25, 1994;22(8):1389-93.
Weaver, D., et al., "A Transgenic Immunoglobulin Mu Gene Prevents Rearrangement of Endogenous Genes", *Cell* 42: 117-127 (1985).
Weiss, R., "Mice Making Human-Like Antibodies", *The Washington Post*, Apr. 28, 1994.
Yamamura, K.-I., et al., "Cell-type-specific and regulated expression of a human γ1 heavy-chain immunoglobulin gene in transgenic mice", *Proc. Natl. Acad. Sci. USA* 83: 2152-2156 (1986).
Yancopoulos, G.D., and Alt, F.W., "Developmentally Controlled and Tissue-Specific Expression of Unrearranged $V_H$ gene segments", *Cell* 40:271-281 (1985).
Yancopoulos, G.D., and Alt, F.W., "Regulation of the Assembly and Expression of Variable-Region Genes", *Ann. Rev. Immunol.* 4:339-368 (1986).
Yasui, H, et al., "Class switch from μ to δ is mediated by homologous recombination between .$\delta_\mu$ and $\Sigma_\mu$ sequences in human immunoglobulin gene loci", *Eur. J. Immunol.* 19: 1399-1403 (1989).
Zijlstra, M., et al., "Germ-line transmission of a disrupted $\beta_2$-microglobulin gene produced by homologous recombination in embryonic stem cells", *Nature* 342:435-438 (1989).
Zimmer, A., and Gruss, P., "Production of chimaeric mice containing embryonic stem (ES) cells carrying a homoeobox *Hox 1.1* allele mutated by homologous recombination", *Nature* 338:150-153 (1989).

* cited by examiner

| Expected Fragment Sizes (kb) using Probe A | | |
|---|---|---|
| Restriction Digest | Fragment Length wild type | mutant |
| BglI | 15.7 | 7.7 |
| Bst XI | 7.3 | 6.6 |
| Spe I | 9.9 | 7.6 |
| Eco RI | 12.5 | 14.3 |

SEQUENCE LISTING

<160> NUMBER OF SEQ ID NOS: 10

<210> SEQ ID NO 1
<211> LENGTH: 3881
<212> TYPE: DNA
<213> ORGANISM: Artificial Sequence
<220> FEATURE:
<223> OTHER INFORMATION: Description of Artificial Sequence: Kappa light chain plasmid
<223> OTHER INFORMATION: pCK7-96

<400> SEQUENCE: 1

```
tcttccgctt cctcgctcac tgactcgctg cgctcggtcg ttcggctgcg gcgagcggta     60
tcagctcact caaaggcggt aatacggtta tccacagaat caggggataa cgcaggaaag    120
aacatgtgag caaaaggcca gcaaaaggcc aggaaccgta aaaaggccgc gttgctggcg    180
tttttccata ggctccgccc ccctgacgag catcacaaaa atcgacgctc aagtcagagg    240
tggcgaaacc cgacaggact ataaagatac caggcgtttc cccctggaag ctccctcgtg    300
cgctctcctg ttccgaccct gccgcttacc ggatacctgt ccgcctttct cccttcggga    360
agcgtggcgc tttctcatag ctcacgctgt aggtatctca gttcggtgta ggtcgttcgc    420
tccaagctgg gctgtgtgca cgaacccccc gttcagcccg accgctgcgc cttatccggt    480
aactatcgtc ttgagtccaa cccggtaaga cacgacttat cgccactggc agcagccact    540
ggtaacagga ttagcagagc gaggtatgta ggcggtgcta cagagttctt gaagtggtgg    600
cctaactacg gctacactag aaggacagta tttggtatct gcgctctgct gaagccagtt    660
accttcggaa aaagagttgg tagctcttga tccggcaaac aaaccaccgc tggtagcggt    720
ggtttttttg tttgcaagca gcagattacg cgcagaaaaa aaggatctca agaagatcct    780
ttgatctttt ctacggggtc tgacgctcag tggaacgaaa actcacgtta agggattttg    840
gtcatgagat tatcaaaaag gatcttcacc tagatccttt taaattaaaa atgaagtttt    900
aaatcaatct aaagtatata tgagtaaact tggtctgaca gttaccaatg cttaatcagt    960
gaggcaccta tctcagcgat ctgtctattt cgttcatcca tagttgcctg actccccgtc   1020
gtgtagataa ctacgatacg ggagggctta ccatctggcc ccagtgctgc aatgataccg   1080
cgagacccac gctcaccggc tccagattta tcagcaataa accagccagc cggaagggcc   1140
gagcgcagaa gtggtcctgc aactttatcc gcctccatcc agtctattaa ttgttgccgg   1200
gaagctagag taagtagttc gccagttaat agtttgcgca acgttgttgc cattgctaca   1260
ggcatcgtgg tgtcacgctc gtcgtttggt atggcttcat tcagctccgg ttcccaacga   1320
tcaaggcgag ttacatgatc ccccatgttg tgcaaaaaag cggttagctc cttcggtcct   1380
ccgatcgttg tcagaagtaa gttggccgca gtgttatcac tcatggttat ggcagcactg   1440
cataattctc ttactgtcat gccatccgta agatgctttt ctgtgactgg tgagtactca   1500
accaagtcat tctgagaata gtgtatgcgg cgaccgagtt gctcttgccc ggcgtcaata   1560
cgggataata ccgcgccaca tagcagaact ttaaaagtgc tcatcattgg aaaacgttct   1620
tcggggcgaa aactctcaag gatcttaccg ctgttgagat ccagttcgat gtaacccact   1680
cgtgcaccca actgatcttc agcatctttt actttcacca gcgtttctgg gtgagcaaaa   1740
acaggaaggc aaaatgccgc aaaaaaggga ataagggcga cacggaaatg ttgaatactc   1800
atactcttcc tttttcaata ttattgaagc atttatcagg gttattgtct catgagcgga   1860
tacatatttg aatgtattta gaaaaataaa caaatagggg ttccgcgcac atttccccga   1920
```

-continued

```
aaagtgccac ctgacgtcta agaaaccatt attatcatga cattaaccta taaaaatagg   1980

cgtatcacga ggccctttcg tctcgcgcgt ttcggtgatg acggtgaaaa cctctgacac   2040

atgcagctcc cggagacggt cacagcttgt ctgtaagcgg atgccgggag cagacaagcc   2100

cgtcagggcg cgtcagcggg tgttggcggg tgtcggggct ggcttaacta tgcggcatca   2160

gagcagattg tactgagagt gcaccatatg cggtgtgaaa taccgcacag atgcgtaagg   2220

agaaaatacc gcatcaggcg ccattcgcca ttcaggctgc gcaactgttg ggaagggcga   2280

tcggtgcggg cctcttcgct attacgccag ctggcgaaag ggggatgtgc tgcaaggcga   2340

ttaagttggg taacgccagg gttttcccag tcacgacgtt gtaaaacgac ggccagtgcc   2400

aagctagcgg ccgcggtcca accaccaatc tcaaagcttg gtacccggga gcctgttatc   2460

ccagcacagt cctggaagag gcacagggga aataaaagcg gacggaggct ttccttgact   2520

cagccgctgc ctggtcttct tcagacctgt tctgaattct aaactctgag gggtcggat    2580

gacgtggcca ttctttgcct aaagcattga gtttactgca aggtcagaaa agcatgcaaa   2640

gccctcagaa tggctgcaaa gagctccaac aaaacaattt agaactttat taaggaatag   2700

ggggaagcta ggaagaaact caaaacatca agattttaaa tacgcttctt ggtctccttg   2760

ctataattat ctgggataag catgctgttt tctgtctgtc cctaacatgc cctgtgatta   2820

tccgcaaaca acacacccaa gggcagaact ttgttactta aacaccatcc tgtttgcttc   2880

tttcctcagg aactgtggct gcaccatctg tcttcatctt cccgccatct gatgagcagt   2940

tgaaatctgg aactgcctct gttgtgtgcc tgctgaataa cttctatccc agagaggcca   3000

aagtacagtg gaaggtggat aacgccctcc aatcgggtaa ctcccaggag agtgtcacag   3060

agcaggacag caaggacagc acctacagcc tcagcagcac cctgacgctg agcaaagcag   3120

actacgagaa acacaaagtc tacgcctgcg aagtcaccca tcagggcctg agctcgcccg   3180

tcacaaagag cttcaacagg ggagagtgtt agagggagaa gtgcccccac ctgctcctca   3240

gttccagcct gacccctcc catcctttgg cctctgaccc tttttccaca ggggacctac    3300

ccctattgcg gtcctccagc tcatctttca cctcaccccc ctcctcctcc ttggctttaa   3360

ttatgctaat gttggaggag aatgaataaa taaagtgaat ctttgcacct gtggtttctc   3420

tctttcctca atttaataat tattatctgt tgtttaccaa ctactcaatt tctcttataa   3480

gggactaaat atgtagtcat cctaaggcgc ataaccattt ataaaaatca tccttcattc   3540

tattttaccc tatcatcctc tgcaagacag tcctccctca aacccacaag ccttctgtcc   3600

tcacagtccc ctgggccatg gatcctcaca tcccaatccg cggccgcaat tcgtaatcat   3660

ggtcatagct gtttcctgtg tgaaattgtt atccgctcac aattccacac aacatacgag   3720

ccggaagcat aaagtgtaaa gcctggggtg cctaatgagt gagctaactc acattaattg   3780

cgttgcgctc actgcccgct ttccagtcgg gaaacctgtc gtgccagctg cattaatgaa   3840

tcggccaacg cgcggggaga ggcggtttgc gtattgggcg c                       3881
```

<210> SEQ ID NO 2
<211> LENGTH: 4723
<212> TYPE: DNA
<213> ORGANISM: Artificial Sequence
<220> FEATURE:
<223> OTHER INFORMATION: Description of Artificial Sequence: Gamma1 heavy chain plasmid
<223> OTHER INFORMATION: pCG7-96

-continued

<400> SEQUENCE: 2

```
gaactcgagc agctgaagct ttctggggca ggccaggcct gaccttggct ttggggcagg     60
gagggggcta aggtgaggca ggtggcgcca gccaggtgca cacccaatgc ccatgagccc    120
agacactgga cgctgaacct cgcggacagt taagaaccca ggggcctctg cgccctgggc    180
ccagctctgt cccacaccgc ggtcacatgg caccacctct cttgcagcct ccaccaaggg    240
cccatcggtc ttccccctgg caccctcctc caagagcacc tctgggggca cagcggccct    300
gggctgcctg gtcaaggact acttccccga accggtgacg gtgtcgtgga actcaggcgc    360
cctgaccagc ggcgtgcaca ccttcccggc tgtcctacag tcctcaggac tctactccct    420
cagcagcgtg gtgaccgtgc cctccagcag cttgggcacc cagacctaca tctgcaacgt    480
gaatcacaag cccagcaaca ccaaggtgga caagaaagtt ggtgagaggc cagcacaggg    540
agggagggtg tctgctggaa gccaggctca gcgctcctgc ctggacgcat cccggctatg    600
cagccccagt ccagggcagc aaggcaggcc ccgtctgcct cttcacccgg aggcctctgc    660
ccgccccact catgctcagg gagagggtct tctggctttt tccccaggct ctgggcaggc    720
acaggctagg tgcccctaac ccaggccctg cacacaaagg ggcaggtgct gggctcagac    780
ctgccaagag ccatatccgg gaggaccctg cccctgacct aagcccaccc caaaggccaa    840
actctccact ccctcagctc ggacaccttc tctcctccca gattccagta actcccaatc    900
ttctctctgc agagcccaaa tcttgtgaca aaactcacac atgcccaccg tgcccaggta    960
agccagccca ggcctcgccc tccagctcaa ggcgggacag gtgccctaga gtagcctgca   1020
tccagggaca ggccccagcc gggtgctgac acgtccacct ccatctcttc ctcagcacct   1080
gaactcctgg ggggaccgtc agtcttcctc ttccccccaa aacccaagga caccctcatg   1140
atctcccgga cccctgaggt cacatgcgtg gtggtggacg tgagccacga agaccctgag   1200
gtcaagttca actggtacgt ggacggcgtg gaggtgcata atgccaagac aaagccgcgg   1260
gaggagcagt acaacagcac gtaccgtgtg gtcagcgtcc tcaccgtcct gcaccaggac   1320
tggctgaatg gcaaggagta caagtgcaag gtctccaaca aagccctccc agcccccatc   1380
gagaaaacca tctccaaagc caaaggtggg acccgtgggg tgcgagggcc acatggacag   1440
aggccggctc ggcccaccct ctgccctgag agtgaccgct gtaccaacct ctgtccctac   1500
agggcagccc cgagaaccac aggtgtacac cctgccccca tcccgggatg agctgaccaa   1560
gaaccaggtc agcctgacct gcctggtcaa aggcttctat cccagcgaca tcgccgtgga   1620
gtgggagagc aatgggcagc cggagaacaa ctacaagacc acgcctcccg tgctggactc   1680
cgacggctcc ttcttcctct acagcaagct caccgtggac aagagcaggt ggcagcaggg   1740
gaacgtcttc tcatgctccg tgatgcatga ggctctgcac aaccactaca cgcagaagag   1800
cctctccctg tctccgggta aatgagtgcg acggccggca agcccccgct ccccgggctc   1860
tcgcggtcgc acgaggatgc ttggcacgta ccccctgtac atacttcccg ggcgcccagc   1920
atggaaataa agcacccagc gctgccctgg gcccctgcga gactgtgatg gttctttcca   1980
cgggtcaggc cgagtctgag gcctgagtgg catgagggag gcagagcggg tcccactgtc   2040
cccacactgg cccaggctgt gcaggtgtgc ctgggccccc tagggtgggg ctcagccagg   2100
ggctgccctc ggcagggtgg gggatttgcc agcgtggccc tccctccagc agcacctgcc   2160
ctgggctggg ccacgggaag ccctaggagc ccctggggac agacacacag cccctgcctc   2220
tgtaggagac tgtcctgttc tgtgagcgcc cctgtcctcc cgacctccat gcccactcgg   2280
gggcatgcct gcaggtcgac tctagaggat ccccgggtac cgagctcgaa ttcatcgatg   2340
```

-continued

```
atatcagatc tgccggtctc cctatagtga gtcgtattaa tttcgataag ccaggttaac   2400
ctgcattaat gaatcggcca acgcgcgggg agaggcggtt tgcgtattgg gcgctcttcc   2460
gcttcctcgc tcactgactc gctgcgctcg gtcgttcggc tgcggcgagc ggtatcagct   2520
cactcaaagg cggtaatacg gttatccaca gaatcagggg ataacgcagg aaagaacatg   2580
tgagcaaaag gccagcaaaa ggccaggaac cgtaaaaagg ccgcgttgct ggcgtttttc   2640
cataggctcc gcccccctga cgagcatcac aaaaatcgac gctcaagtca gaggtggcga   2700
aacccgacag gactataaag ataccaggcg tttccccctg gaagctccct cgtgcgctct   2760
cctgttccga ccctgccgct taccggatac ctgtccgcct ttctcccttc gggaagcgtg   2820
gcgctttctc aatgctcacg ctgtaggtat ctcagttcgg tgtaggtcgt tcgctccaag   2880
ctgggctgtg tgcacgaacc ccccgttcag cccgaccgct gcgccttatc cggtaactat   2940
cgtcttgagt ccaacccggt aagacacgac ttatcgccac tggcagcagc cactggtaac   3000
aggattagca gagcgaggta tgtaggcggt gctacagagt tcttgaagtg gtggcctaac   3060
tacggctaca ctagaaggac agtatttggt atctgcgctc tgctgaagcc agttaccttc   3120
ggaaaaagag ttggtagctc ttgatccggc aaacaaacca ccgctggtag cggtggtttt   3180
tttgtttgca agcagcagat tacgcgcaga aaaaaaggat ctcaagaaga tcctttgatc   3240
ttttctacgg ggtctgacgc tcagtggaac gaaaactcac gttaagggat tttggtcatg   3300
agattatcaa aaaggatctt cacctagatc cttttaaatt aaaaatgaag ttttaaatca   3360
atctaaagta tatatgagta aacttggtct gacagttacc aatgcttaat cagtgaggca   3420
cctatctcag cgatctgtct atttcgttca tccatagttg cctgactccc cgtcgtgtag   3480
ataactacga tacgggaggg cttaccatct ggccccagtg ctgcaatgat accgcgagac   3540
ccacgctcac cggctccaga tttatcagca ataaaccagc cagccggaag ggccgagcgc   3600
agaagtggtc ctgcaacttt atccgcctcc atccagtcta ttaattgttg ccgggaagct   3660
agagtaagta gttcgccagt taatagtttg cgcaacgttg ttgccattgc tacaggcatc   3720
gtggtgtcac gctcgtcgtt tggtatggct tcattcagct ccggttccca acgatcaagg   3780
cgagttacat gatcccccat gttgtgcaaa aaagcggtta gctccttcgg tcctccgatc   3840
gttgtcagaa gtaagttggc cgcagtgtta tcactcatgg ttatggcagc actgcataat   3900
tctcttactg tcatgccatc cgtaagatgc ttttctgtga ctggtgagta ctcaaccaag   3960
tcattctgag aatagtgtat gcggcgaccg agttgctctt gcccggcgtc aatacgggat   4020
aataccgcgc cacatagcag aactttaaaa gtgctcatca ttggaaaacg ttcttcgggg   4080
cgaaaactct caaggatctt accgctgttg agatccagtt cgatgtaacc cactcgtgca   4140
cccaactgat cttcagcatc ttttactttc accagcgttt ctgggtgagc aaaaacagga   4200
aggcaaaatg ccgcaaaaaa gggaataagg gcgacacgga aatgttgaat actcatactc   4260
ttcctttttc aatattattg aagcatttat cagggttatt gtctcatgag cggatacata   4320
tttgaatgta tttagaaaaa taaacaaata ggggttccgc gcacatttcc ccgaaaagtg   4380
ccacctgacg tctaagaaac cattattatc atgacattaa cctataaaaa taggcgtatc   4440
acgaggccct ttcgtctcgc gcgtttcggt gatgacggtg aaaacctctg acacatgcag   4500
ctcccggaga cggtcacagc ttgtctgtaa gcggatgccg ggagcagaca agcccgtcag   4560
ggcgcgtcag cgggtgttgg cgggtgtcgg ggctggctta actatgcggc atcagagcag   4620
attgtactga gagtgcacca tatggacata ttgtcgttag aacgcggcta caattaatac   4680
ataaccttat gtatcataca catacgattt aggtgacact ata                      4723
```

```
<210> SEQ ID NO 3
<211> LENGTH: 4694
<212> TYPE: DNA
<213> ORGANISM: Artificial Sequence
<220> FEATURE:
<223> OTHER INFORMATION: Description of Artificial Sequence: Gamma4
      heavy chain plasmid
<223> OTHER INFORMATION: pG4HE

<400> SEQUENCE: 3

gaactcgagc agctgaagct ttctggggca ggccgggcct gactttggct gggggcaggg     60

agggggctaa ggtgacgcag gtggcgccag ccaggtgcac acccaatgcc catgagccca    120

gacactggac cctgcatgga ccatcgcgga tagacaagaa ccgaggggcc tctgcgccct    180

gggcccagct ctgtcccaca ccgcggtcac atggcaccac ctctcttgca gcttccacca    240

agggcccatc cgtcttcccc ctggcgccct gctccaggag cacctccgag agcacagccg    300

ccctgggctg cctggtcaag gactacttcc ccgaaccggt gacggtgtcg tggaactcag    360

gcgccctgac cagcggcgtg cacaccttcc cggctgtcct acagtcctca ggactctact    420

ccctcagcag cgtggtgacc gtgccctcca gcagcttggg cacgaagacc tacacctgca    480

acgtagatca caagcccagc aacaccaagg tggacaagag agttggtgag aggccagcac    540

agggagggag ggtgtctgct ggaagccagg ctcagccctc ctgcctggac gcaccccggc    600

tgtgcagccc cagcccaggg cagcaaggca tgccccatct gtctcctcac ccggaggcct    660

ctgaccaccc cactcatgct cagggagagg gtcttctgga tttttccacc aggctccggg    720

cagccacagg ctggatgccc ctaccccagg ccctgcgcat acaggggcag gtgctgcgct    780

cagacctgcc aagagccata tccgggagga ccctgcccct gacctaagcc caccccaaag    840

gccaaactct ccactccctc agctcagaca ccttctctcc tcccagatct gagtaactcc    900

caatcttctc tctgcagagt ccaaatatgg tcccccatgc ccatcatgcc caggtaagcc    960

aacccaggcc tcgccctcca gctcaaggcg ggacaggtgc cctagagtag cctgcatcca   1020

gggacaggcc ccagccgggt gctgacgcat ccacctccat ctcttcctca gcacctgagt   1080

tcctgggggg accatcagtc ttcctgttcc ccccaaaacc caaggacact ctcatgatct   1140

cccggacccc tgaggtcacg tgcgtggtgg tggacgtgag ccaggaagac cccgaggtcc   1200

agttcaactg gtacgtggat ggcgtggagg tgcataatgc caagacaaag ccgcgggagg   1260

agcagttcaa cagcacgtac cgtgtggtca gcgtcctcac cgtcctgcac caggactggc   1320

tgaacggcaa ggagtacaag tgcaaggtct ccaacaaagg cctcccgtcc tccatcgaga   1380

aaaccatctc caaagccaaa ggtgggaccc acggggtgcg agggccacat ggacagaggt   1440

cagctcggcc caccctctgc cctgggagtg accgctgtgc caacctctgt ccctacaggg   1500

cagccccgag agccacaggt gtacaccctg cccccatccc aggaggagat gaccaagaac   1560

caggtcagcc tgacctgcct ggtcaaaggc ttctacccca gcgacatcgc cgtggagtgg   1620

gagagcaatg ggcagccgga gaacaactac aagaccacgc ctcccgtgct ggactccgac   1680

ggctccttct tcctctacag caggctaacc gtggacaaga gcaggtggca ggaggggaat   1740

gtcttctcat gctccgtgat gcatgaggct ctgcacaacc actacacaca gaagagcctc   1800

tccctgtctc tgggtaaatg agtgccaggg ccggcaagcc cccgctcccc gggctctcgg   1860

ggtcgcgcga ggatgcttgg cacgtacccc gtctacatac ttcccaggca cccagcatgg   1920

aaataaagca cccaccactg ccctgggccc ctgtgagact gtgatggttc tttccacggg   1980

tcaggccgag tctgaggcct gagtgacatg agggaggcag agcgggtccc actgtcccca   2040
```

-continued

```
cactggccca ggctgtgcag gtgtgcctgg gccacctagg gtggggctca gccaggggct   2100
gccctcggca gggtggggga tttgccagcg tggccctccc tccagcagca gctgccctgg   2160
gctgggccac gggaagccct aggagcccct ggggacagac acacagcccc tgcctctgta   2220
ggagactgtc ctgtcctgtg agcgccctgt cctccgaccc cccatgccca ctcgggggga   2280
tccccgggta ccgagctcga attcatcgat gatatcagat ctgccggtct ccctatagtg   2340
agtcgtatta atttcgataa gccaggttaa cctgcattaa tgaatcggcc aacgcgcggg   2400
gagaggcggt ttgcgtattg ggcgctcttc cgcttcctcg ctcactgact cgctgcgctc   2460
ggtcgttcgg ctgcggcgag cggtatcagc tcactcaaag gcggtaatac ggttatccac   2520
agaatcaggg gataacgcag gaaagaacat gtgagcaaaa ggccagcaaa aggccaggaa   2580
ccgtaaaaag gccgcgttgc tggcgttttt ccataggctc cgcccccctg acgagcatca   2640
caaaaatcga cgctcaagtc agaggtggcg aaacccgaca ggactataaa gataccaggc   2700
gtttccccct ggaagctccc tcgtgcgctc tcctgttccg accctgccgc ttaccggata   2760
cctgtccgcc tttctccctt cgggaagcgt ggcgctttct caatgctcac gctgtaggta   2820
tctcagttcg gtgtaggtcg ttcgctccaa gctgggctgt gtgcacgaac cccccgttca   2880
gcccgaccgc tgcgccttat ccggtaacta tcgtcttgag tccaacccgg taagacacga   2940
cttatcgcca ctggcagcag ccactggtaa caggattagc agagcgaggt atgtaggcgg   3000
tgctacagag ttcttgaagt ggtggcctaa ctacggctac actagaagga cagtatttgg   3060
tatctgcgct ctgctgaagc cagttacctt cggaaaaaga gttggtagct cttgatccgg   3120
caaacaaacc accgctggta gcggtggttt ttttgtttgc aagcagcaga ttacgcgcag   3180
aaaaaaagga tctcaagaag atcctttgat cttttctacg gggtctgacg ctcagtggaa   3240
cgaaaactca cgttaaggga ttttggtcat gagattatca aaaaggatct tcacctagat   3300
ccttttaaat taaaaatgaa gttttaaatc aatctaaagt atatatgagt aaacttggtc   3360
tgacagttac caatgcttaa tcagtgaggc acctatctca gcgatctgtc tatttcgttc   3420
atccatagtt gcctgactcc ccgtcgtgta gataactacg atacgggagg gcttaccatc   3480
tggccccagt gctgcaatga taccgcgaga cccacgctca ccggctccag atttatcagc   3540
aataaaccag ccagccggaa gggccgagcg cagaagtggt cctgcaactt tatccgcctc   3600
catccagtct attaattgtt gccgggaagc tagagtaagt agttcgccag ttaatagttt   3660
gcgcaacgtt gttgccattg ctacaggcat cgtggtgtca cgctcgtcgt ttggtatggc   3720
ttcattcagc tccggttccc aacgatcaag gcgagttaca tgatccccca tgttgtgcaa   3780
aaaagcggtt agctccttcg gtcctccgat cgttgtcaga agtaagttgg ccgcagtgtt   3840
atcactcatg gttatggcag cactgcataa ttctcttact gtcatgccat ccgtaagatg   3900
cttttctgtg actggtgagt actcaaccaa gtcattctga gaatagtgta tgcggcgacc   3960
gagttgctct tgcccggcgt caatacggga taataccgcg ccacatagca gaactttaaa   4020
agtgctcatc attggaaaac gttcttcggg gcgaaaactc tcaaggatct taccgctgtt   4080
gagatccagt tcgatgtaac ccactcgtgc acccaactga tcttcagcat cttttacttt   4140
caccagcgtt tctgggtgag caaaaacagg aaggcaaaat gccgcaaaaa agggaataag   4200
ggcgacacgg aaatgttgaa tactcatact cttccttttt caatattatt gaagcattta   4260
tcagggttat tgtctcatga gcggatacat atttgaatgt atttagaaaa ataaacaaat   4320
aggggttccg cgcacatttc cccgaaaagt gccacctgac gtctaagaaa ccattattat   4380
catgacatta acctataaaa ataggcgtat cacgaggccc tttcgtctcg cgcgtttcgg   4440
```

```
tgatgacggt gaaaacctct gacacatgca gctcccggag acggtcacag cttgtctgta   4500

agcggatgcc gggagcagac aagcccgtca gggcgcgtca gcgggtgttg gcgggtgtcg   4560

gggctggctt aactatgcgg catcagagca gattgtactg agagtgcacc atatggacat   4620

attgtcgtta gaacgcggct acaattaata cataacctta tgtatcatac acatacgatt   4680

taggtgacac tata                                                     4694


<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Probe
      for region 5' of V kappa O1

<400> SEQUENCE: 4

ccaccccata aacactgatt c                                               21


<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Probe for region 5' of V kappa O1

<400> SEQUENCE: 5

ttgatgcatc ctacccaggg c                                               21


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Probe
      for V kappa L24  and L25 intergenic region

<400> SEQUENCE: 6

cctgccttac agtgctgtag                                                 20


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Probe
      for V kappa L24 and L25 intergenic region.

<400> SEQUENCE: 7

ggacagcaac aggacatggg                                                 20


<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: PCR
      primer neo <400> SEQUENCE: 8

ctcgtgcttt acggtatcgc c                                               21


<210> SEQ ID NO 9
<211> LENGTH: 21
<212> TYPE: DNA
<213> ORGANISM: Artificial Sequence
```

-continued

```
<220> FEATURE:
<223> OTHER INFORMATION: Description of Artificial Sequence: PCR
      primer 5'EC1

<400> SEQUENCE: 9

aaactcgacc ccccgtggat c                                           21


<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: PCR
      primer 3'EC1

<400> SEQUENCE: 10

ttgactgtgg ccttaaacgt gtag                                        24
```

TRANSGENIC TRANSCHROMOSOMAL RODENTS FOR MAKING HUMAN ANTIBODIES

CROSS-REFERENCE TO RELATED APPLICATIONS

This application claims priority to U.S. Provisional Application No. 60/250,340, filed on Nov. 30, 2000, the disclosure of which is incorporated herein in its entirety.

TECHNICAL FIELD

The invention resides in the technical fields of transgenic animals, molecular immunology and medicine.

BACKGROUND OF THE INVENTION

Antibodies represent a class of therapeutic molecules with applications in many different areas including transplantation, cardiovascular diseases, infectious diseases, cancer, and autoimmunity (Goldenberg, M., 1999, *Clin. Ther.* 21:309–318; Present, D. et al., 1999, *New Engl. J. Med.* 340:1398–1405; Targan, S. et al., 1997, *New Engl. J. Med.* 337:1029–1035; Davis, T. et al., 1999, *Blood* 94:88a; Saez-Llorens, X. et al., 1998, *Pediatr. Infect. Dis. J.* 17:787–791; Berard, J. et al., 1999, *Pharmacotherapy* 19:1127–1137; Glennie, M. et al. 2000, *Immunol. Today* 21:403–410; Miller, R., 1982, *New Engl. J. Med.* 306:517–522; Maini, R., et al., 1999, *Lancet,* 354:1932–1939). The development of hybridoma technology enabled the isolation of rodent monoclonal antibodies (also referred to as MAbs) as candidate therapeutic molecules (Kohler, G. and Milstein, C., 1975, *Nature* 256:495–497). However, early studies involving the use of non-human monoclonal antibodies for in vivo human therapy, demonstrated that human anti-mouse antibody (HAMA) responses could limit the use of such agents (Schroff, R. et al., 1985, *Cancer Res.* 45,879–885; Shawler, D. et al., 1985, *J. Immunol.* 135:1530–1535). Thus it is recognized that a reduction in the immunogenicity of therapeutic antibodies is desirable. Recombinant DNA technologies have been employed to reduce the immunogenicity of non-human antibodies (Boulianne, G. et al., 1984, *Nature* 312, 643–646; Morrison, S. et al., 1984, *Proc. Natl. Acad. Sci. U.S.A.* 81:6851–6855; Riechmann, L. et al., 1988, *Nature* 332:323–327; Jones, P. et al., 1986, *Nature* 321: 522–525; Queen, C. et al., 1989, *Proc. Natl. Acad. Sci. U.S.A.* 86:10029–10033). However, it is also recognized that fully human monoclonal antibodies are a potential source of low immunogenicity therapeutic 30 agents for treating human diseases (Little, M. et al., 2000, *Immunol. Today* 21:364–70). The use of transgenic mice carrying human immunoglobulin (Ig) loci in their germline configuration provide for the isolation of high affinity fully human monoclonal antibodies directed against a variety of targets including human self antigens for which the normal human immune system is tolerant (Lonberg, N. et al., 1994, *Nature* 368:856–9; Green, L. et al., 1994, *Nature Genet.* 7:13–21; Green, L. & Jakobovits, 1998, *Exp. Med.* 188:483–95; Lonberg, N and Huszar, D., 1995, *Int. Rev. Immunol.* 13:65–93; Bruggemann, M. et al., 1991, *Eur. J. Immunol.* 21:1323–1326; Fishwild, D. et al., 1996, *Nat. Biotechnol.* 14:845–851; Mendez, M. et al., 1997, *Nat. Genet.* 15:146–156; Green, L., 1999, *J. Immunol. Methods* 231: 11–23; Yang, X. et al., 1999, *Cancer Res.* 59:1236–1243; Brüggemann, M. and Taussig, M J., *Curr. Opin. Biotechnol.* 8:455–458, 1997). Human antibodies fall into a variety of different classes based on light chain (kappa and Lambda) and heavy chain ($IgA_1$, $IgA_2$, IgD, IgE, $IgG_1$, $IgG_2$, $IgG_3$, $IgG_4$, and IgM). These different classes potentially provide for different therapeutic uses. For example, the different heavy chain isotypes have different interactions with complement and with cell based Fc receptors. Some of the heavy chain classes (IgM and IgA) can also form multimers, thus increasing the valency of $F_c$ and V region interactions. It is therefore desirable to have a platform for generating human monoclonal antibodies of all isotypes. However, the large size of human Ig loci (1–2 Mb) had been a major obstacle for the introduction of entire loci into transgenic mice to reconstitute full diverse human antibody repertoires because the cloning of over megabase-sized DNA fragments encompassing whole human Ig loci was difficult even with the use of yeast artificial chromosomes. Recently, a novel procedure using a human chromosome itself as a vector for transgenesis facilitated the transfer of the complete IgH and IgK loci into transgenic mice without the need for cloning DNA fragments into artificial DNA vectors (Tomizuka, K. et al., 1997, *Nature Genet.* 16:133–143; Tomizuka, K. et al., 2000, *Proc. Natl. Acad. Sci.* 97:722–727). Tomizuka et al. (Tomizuka, K. et al., 2000, *Proc. Natl. Acad. Sci. U.S.A.* 97:722–727) demonstrated the introduction of two transmittable human chromosome fragments (hCFs), one containing the immunoglobulin (Ig) heavy chain locus (IgH, ~1.5 Mb) and the other the K light chain locus (IgH, ~2 Mb), into a transgenic mouse strain whose endogenous IgH and IgK loci were inactivated. In the resultant double-transchromosomic (Tc)/double-knockout (KO) mice, a substantial proportion of the somatic cells retained both hCFs, and the rescue in the defect of Ig production was showed by high level expression of human Ig heavy and kappa light chains in the absence of mouse heavy and kappa light chains. In addition, serum expression profiles of four human Ig γ subclasses resembled those seen in humans. The transgenic mice developed an antigen-specific human antibody response upon immunization with human serum albumin (HSA), and HSA-specific human monoclonal antibodies with various isotypes were obtained from them. The study of Tomizuka et al. (ibid.) also demonstrated the instability of hChr.2-derived hCF containing the Igk locus (hCF(2-W23)) in mice. The observed instability of the κ transchromosome could be a impediment to optimal human kappa light chain expression and production of human kappa-positive hybridomas. Indeed, two-thirds of anti-HSA hybridomas obtained from a double-Tc/KO mouse were mouse lambda-positive ($m\lambda^+$) and a majority (83%) of IgG/mX hybridomas was found to have lost the hCF(2-W23). Therefore, there is a need for transgenic animals that retain characteristics conferred by the transchromosomes described by Tomizuka et al. (ibid.), particularly animals that express substantially the full repertoire of human heavy chain isotypes, and also exhibit improved stability of introduced human sequences, allowing for increased efficiency of obtaining fully human antibodies.

BRIEF SUMMARY OF THE INVENTION

The invention provides a transgenic nonhuman mammal comprising two human immunoglobulin loci, wherein one of two said human immunoglobulin loci is a human heavy chain locus and the other locus is a human light chain locus; and wherein only one of said loci is of a transchromosome. In some transgenic nonhuman mammals, the transchromosome is autonomous. In some transgenic nonhuman mammals, the transchromosome comprises a fragment of human chromosome 14. In some transgenic nonhuman mammals, the human light chain locus is associated with an endogenous mammalian chromosome. In some transgenic nonhuman mammals, the human heavy chain locus is of a transchromosome and the human light chain locus is associated with an endogenous mammalian chromosome. In some such transgenic nonhuman mammals, at least a part of the human light chain locus is cloned into a YAC vector. In some transgenic nonhuman mammals, the human heavy chain locus is comprised in hCF(SC20) and the human light chain locus is comprised in the human kappa light chain locus transgene KCo5. In some transgenic nonhuman mammals, the human light chain locus is of a transchromosome and the human heavy chain locus is associated with an endogenous mammalian chromosome. In some transgenic nonhuman mammals, the transgenic nonhuman mammal is a mouse. In transgenic nonhuman mammals, the endogenous mammalian heavy chain locus and at least one mammalian light chain locus are inactivated. In some such transgenic nonhuman mammals, the endogenous mammalian heavy chain locus and kappa light chain locus are inactivated.

In another aspect, the transgenic nonhuman mammal further comprises a mutation of a gene, wherein the mutation increases the immune response to autoantigen. In some transgenic nonhuman mammals, the mutation is the inactivation of the Fc-gamma IIB gene.

The invention further provides methods for generating a plurality of B cells expressing human antibody sequences, the method comprising: providing the transgenic nonhuman mammal comprising two human immunoglobulin loci, wherein one of two said human immunoglobulin loci is a human heavy chain locus and the other locus is a human light chain locus; and wherein only one of said loci is of a transchromosome, and immunizing the transgenic nonhuman mammal to generate a plurality of B cells expressing human antibody sequences. In some such methods, the transchromosome is a fragment of human chromosome 14. In some such methods, the human transchromosome is human chromosome fragment SC20 (hCF(SC20)). Some such methods further comprise collecting the plurality of B cells expressing sequences expressing human antibodies. Some such methods further comprise fusing the plurality of B cells with immortalized cells to form hybridomas. Other such methods further comprise collecting the human antibody sequences from the hybridomas. In some such methods, the human antibody sequences are purified. Some such methods further comprise collecting the sequences encoding human antibodies. In some such methods the sequences encoding human antibodies are full length. In some methods, the sequences encoding human antibodies are expressed in transfected cells. In some such methods, the human light chain locus comprises unrearranged sequences from the natural human kappa light chain locus. In some such methods, the human kappa light chain locus is the inserted KCo5 transgene. In some such methods, the plurality of B cells comprises at least a first B cell encoding an antibody with a first isotype selected from the group consisting of IgA, IgD, IgE, IgG and IgM. In some methods the IgA isotype is $IgA_1$ or $IgA_2$. In some methods the IgG isotype is $IgG_1$, $IgG_2$, $IgG_3$ or $IgG_4$. In some such methods, the plurality of B cells further comprises at least a second B cell encoding an antibody with a second isotype different from the first isotype selected from the group consisting of IgA, IgD, IgE, IgG and IgM. In some methods, the plurality of B cells comprise at least five B cells each encoding an antibody having a different isotype wherein the isotypes of the antibodies are IgA, IgD, IgE, IgG and IgM respectively. In another aspect, the transgenic nonhuman mammal further comprises a mutation of a gene, wherein the mutation increases the immune response to autoantigen. In some such methods, the mutation is the inactivation of the Fc-gamma IIB gene.

The invention further provides a method for generating a human sequence antibody that binds to a predetermined antigen, the method comprising the following steps: immunizing a transgenic nonhuman mammal with a predetermined antigen, wherein the transgenic nonhuman mammal comprises two human immunoglobulin loci, wherein one of two said human immunoglobulin loci is a human heavy chain locus and the other locus is a human light chain locus; and wherein only one of said loci is of a transchromosome; and collecting the human sequence antibody from the immunized nonhuman mammal. In another aspect, the transgenic nonhuman mammal further comprises a mutation of a gene, wherein the mutation increases the immune response to autoantigen. In some such methods, the mutation is the inactivation of the Fc-gamma IIB gene.

The human sequence antibodies of the invention can encompass various antibody isotypes, or mixtures thereof, such as $IgG_1$, $IgG_2$, $IgG_3$, $IgG_4$, IgM, $IgA_1$, $IgA_2$, IgD, and IgE. The human sequence antibodies can be full-length (e.g., an $IgG_1$, $IgG_4$, $IgA_1$ or an $IgA_2$ antibody) or can include only an antigen-binding portion (e.g., a Fab, F(ab')2, Fv or Fd fragment). Some human sequence antibodies are recombinant human sequence antibodies. Human sequence antibodies of the invention can typically bind to predetermined antigens with equilibrium association constants ($K_a$) of at least $10^8$ $M^{-1}$, $10^9$ $M^{-1}$, $10^{10}$ $M^{-1}$, $10^{11}M^{-1}$, and $10^{12}$ $M^{-1}$. Some human sequence antibodies of the invention are monoclonal. Some human sequence antibodies of the invention are antigen-specific.

The invention further provides a method for generating antigen-specific hybridomas secreting human sequence antibody, the method comprising: immunizing the transgenic nonhuman mammal with a predetermined antigen, wherein the transgenic nonhuman mammal comprises two human immunoglobulin loci, wherein one of two said human immunoglobulin loci is a human heavy chain locus and the other locus is a human light chain locus; and wherein only one of said loci is of a transchromosome; fusing lymphocytes from the transgenic nonhuman mammal with immortalized cells to form hybridoma cells; and determining the binding of the antibody produced by the hybridoma cells to the predetermined antigen. In some such methods greater than 50% of the antigen-specific hybridoma clones secrete antibody having human heavy chain and human light chain. In another aspect, the transgenic nonhuman mammal further comprises a mutation of a gene, wherein the mutation increases the immune response to autoantigen. In some such methods, the mutation is the inactivation of the Fc-gamma IIB gene.

The invention further provides a method for generating a human sequence antibody that binds to a predetermined antigen, the method comprising the following steps: immunizing a transgenic nonhuman mammal with a predetermined antigen; wherein the transgenic nonhuman mammal comprises two human immunoglobulin loci, wherein one of two said human immunoglobulin loci is a human heavy chain locus and the other locus is a human light chain locus wherein only one locus is of a transchromosome; and screening hybridoma cells formed for the presence of antigen reactive antibodies. In some such methods, the hybridoma cells are subcloned at an efficiency of greater than 20%. In some such methods, the antigen reactive antibodies are secreted from the hybridoma in culture. In some such methods, the antigen reactive antibodies are substantially pure. In some methods, the substantially pure antibodies are formulated for therapeutic use. In another aspect, the transgenic nonhuman mammal further comprises a mutation of a gene, wherein the mutation increases the immune response to autoantigen. In some such methods, the mutation is the inactivation of the Fc-gamma IIB gene.

The invention further provides a method for producing rearranged immunoglobulin sequences comprising: providing a transgenic nonhuman mammal, wherein the transgenic nonhuman mammal comprises two human immunoglobulin loci, wherein one of two said human immunoglobulin loci is a human heavy chain locus and the other locus is a human light chain locus wherein only one locus is of a transchromosome; and obtaining the rearranged human immunoglobulin sequences from the transgenic nonhuman mammal. In some methods, the obtaining step comprises collecting B cell lymphocytes containing the rearranged human immunoglobulin sequences from the transgenic nonhuman mammal. In such methods, the obtaining step comprises isolating and amplifying mRNA from B cell lymphocytes to generate cDNA. Some such methods further comprise isolating and amplifying heavy and light chain variable region sequences from the cDNA. The invention further provides isolated nucleic acids encoding these amplified heavy variable region sequences from the cDNA. The invention also provides isolated nucleic acids encoding the amplified light chain variable region sequences from the cDNA. In another aspect, the transgenic nonhuman mammal further comprises a mutation of a gene, wherein the mutation increases the immune response to autoantigen. In some such methods, the mutation is the inactivation of the Fc-gamma IIB gene.

In another aspect, the invention provides nucleic acid molecules encoding the human sequence antibodies, or antigen-binding portions, of the invention. Accordingly, recombinant expression vectors that include the antibody-encoding nucleic acids of the invention, and host cells (or progeny of these host cells) transfected with such vectors, are also encompassed by the invention, as are methods of making the antibodies of the invention by culturing these host cells. Some such methods comprise culturing the host cells under conditions such that the nucleic acid is expressed; and recovering the nucleic acid from the cultured host cell or its cultured medium. Some host cells are eukaryotes. Some such expression vectors comprise a nucleic acid encoding the heavy and light chain variable region sequences of the invention in which the heavy and light chain variable region sequences are operatively linked with a regulatory sequence that controls expression of the nucleic acid in a host cell.

The invention further provides a method of producing a human antibody display library, the method comprising: introducing an immunogen into the nonhuman transgenic mammal, wherein the transgenic nonhuman mammal comprises two human immunoglobulin loci, wherein one of two said human immunoglobulin loci is a human heavy chain locus and the other locus is a human light chain locus wherein only one locus is of a transchromosome; isolating a population of nucleic acids encoding human antibody chains from lymphatic cells of the nonhuman transgenic animal; and forming a library of display packages displaying the antibody chains, wherein a library member comprises a nucleic acid encoding an antibody chain, and the antibody chain is displayed from the package. In some such methods, the nonhuman transgenic mammal lacks a detectable titer to the immunogen when the isolating step is performed. In some such methods, the immunogen is a nucleic acid. In some such methods, the nucleic acid encodes a membrane bound receptor. In another aspect, the transgenic nonhuman mammal further comprises a mutation of a gene, wherein the mutation increases the immune response to autoantigen. In some such methods, the mutation is the inactivation of the Fc-gamma IIB gene.

The invention further provides a method for generating a human sequence antibody, or fragment thereof, that binds to a predetermined antigen, the method comprising the following steps: immunizing a transgenic nonhuman mammal with a predetermined antigen, wherein the transgenic nonhuman mammal comprises two human immunoglobulin loci, wherein one of two said human immunoglobulin loci is a human heavy chain locus and the other locus is a human light chain locus wherein only one locus is of a transchromosome; collecting antibody V region sequences from the immunized transgenic nonhuman mammal; cloning the collected V regions into a DNA vector generating an expression library; expressing the library to identify V region sequences that encode an antibody, or fragment thereof, that binds to the predetermined antigen. In another aspect, the transgenic nonhuman mammal further comprises a mutation of a gene, wherein the mutation increases the immune response to autoantigen. In some such methods, the mutation is the inactivation of the Fc-gamma IIB gene.

The invention further provides a method for generating a human sequence antibody or fragment thereof, that binds to a predetermined antigen, the method comprising the following steps: immunizing a transgenic nonhuman mammal with a predetermined antigen, wherein the transgenic nonhuman mammal comprises at least two human immunoglobulin loci, wherein one of said human immunoglobulin loci is a human heavy chain locus and the other locus is a human light chain locus; and wherein at least one locus is of a transchromosome; isolating CDNA coding at least one human antibody V region from B cells of the immunized transgenic nonhuman mammal or from hybridomas generated by fusion of said B cell and an immortalized cell; cloning said CDNA into an expression vector; introducing said vector into a host cell; culturing said host cell; and collecting said human sequence antibody or fragment thereof from said host cell or culture medium thereof. In some such methods, the isolating step is performed by PCR. In some such methods, the isolating step is performed by cDNA library screening using at least one DNA probe. In some such methods the isolating step is performed by phage display library screening. In some such methods, the CDNA encodes full length human antibody sequences. In some methods, the collected human sequence antibody isotype is different from the isotype of antibody producing cells of said immunized transgenic nonhuman mammal. In another aspect, the transgenic nonhuman mammal further comprises a mutation of a gene, wherein the mutation increases the immune response to autoantigen. In some such methods, the mutation is the inactivation of the Fc-gamma IIB gene.

The invention further provides a method of improving the stability of a transchromosomic mouse hybridoma cell expressing a human antibody reactive with a predetermined antigen, the method comprising: breeding a first mouse, the first mouse comprising a first human immunoglobulin locus on a transchromosome, together with a second mouse, the second mouse comprising a second human immunoglobulin locus inserted within an endogenous mouse chromosome; obtaining a third mouse from the breeding, the third mouse comprising both the first and the second human immunoglobulin loci; immunizing the third mouse, or its progeny, with the predetermined antigen; collecting B cells from the immunized mouse; and fusing the B cells with immortalized cells to obtain hybridoma cells expressing the human antibody reactive with the predetermined antigen. Some such methods further comprise: culturing the hybridoma cells in media; testing the media to identify the presence of hybridoma cells that express human antibodies reactive with the predetermined antigen; diluting the hybridoma cells; and culturing the diluted hybridoma cells to obtain clonal cell lines expressing a monoclonal human antibody reactive with the predetermined antigen. In some such methods, the clonal cell lines are obtained from at least 50% of the identified hybridoma cells.

In another aspect, the invention provides a mouse hybridoma cell secreting a human sequence antibody having an IgA isotype that binds to a specified antigen with an equilibrium association constant (Ka) of at least $10^{10}$ $M^{-1}$.

In another aspect, the invention provides a human sequence antibody having an IgA isotype that binds to a specified antigen with an equilibrium association constant ($K_a$) of at least $10^{10}$ $M^{-1}$.

DETAILED DESCRIPTION OF THE INVENTION

Figure 1:
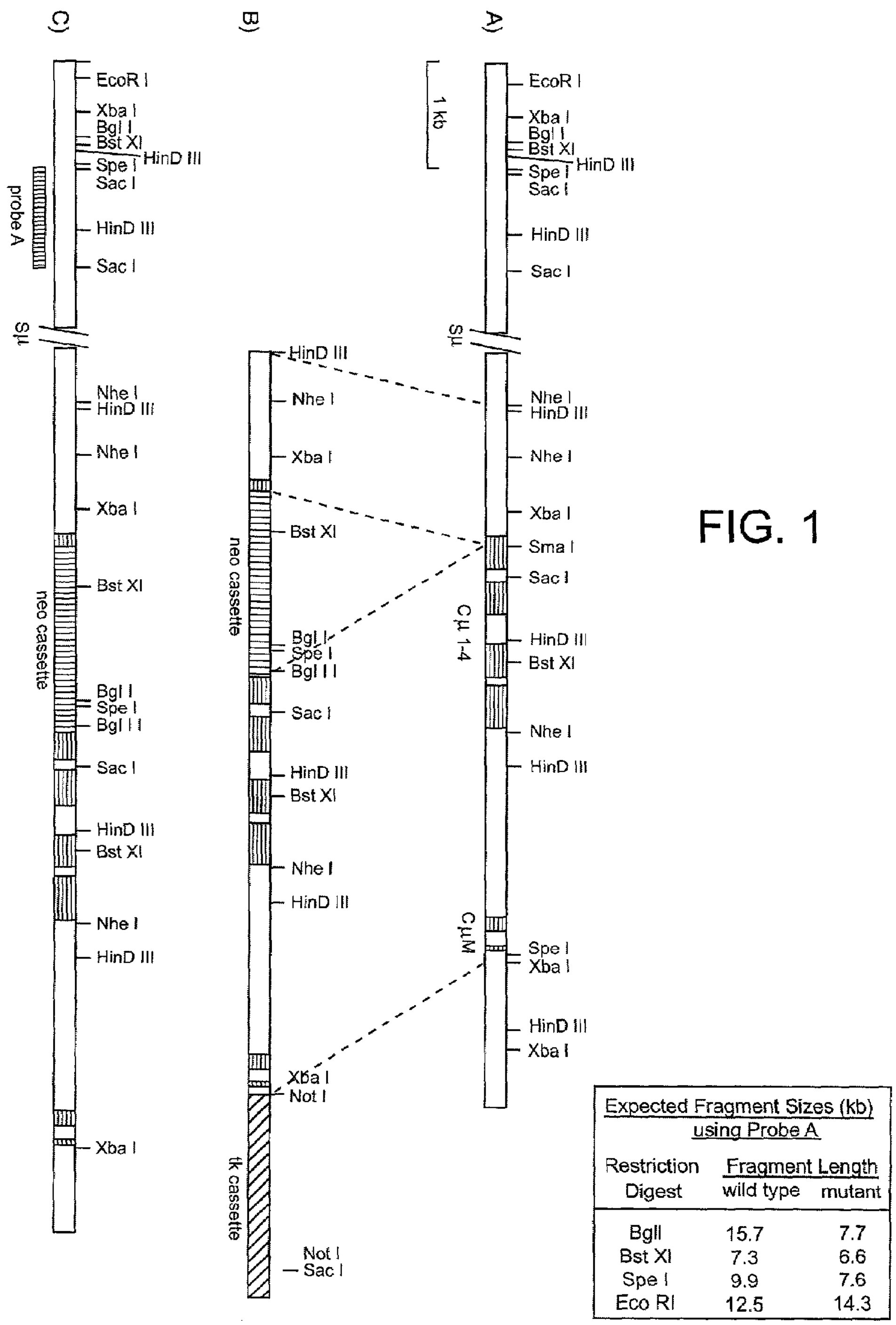
FIG. 1. Design for a Cmu targeting vector. A) Mouse genomic DNA for the Cmu region. B) a Cmu targeting vector. C) The mouse genomic DNA homologous-recombined by the Cmu targeting vector.

The term "transchromosome" refers to a chromosome or fragment thereof that can be transferred into a cell of a nonhuman mammal. An exemplary cell into which the transchromosome are introduced is an ES cell. A transchromosome can comprise selectable marker and can be derived from different species from the nonhuman mammal. A transchromosome can comprise a portion of a human chromosome. The term "transchromosomic or "transchromosome" means "retaining a transchromosome" or "be of a transchromosome".

The human sequence antibodies of the invention can be produced in a non-human transgenic mammal, e.g., a transgenic mouse, capable of producing multiple isotypes of human (e.g., monoclonal or polyclonal) antibodies (e.g., IgM, IgD, IgG, IgA and/or IgE) to a variety of antigens by undergoing V-D-J recombination and, for non IgM/non IgD antibodies, isotype switching. Accordingly, various aspects of the invention include antibodies and antibody fragments, and pharmaceutical compositions thereof, as well as non-human transgenic mammals, and B-cells and hybridomas for making such monoclonal antibodies.

Except when noted, the terms "patient" or "subject" are used interchangeably and refer to mammals such as human patients and non-human primates, as well as experimental animals such as rabbits, rats, and mice, and other animals.

The term "treating" includes the administration of the compounds or agents of the present invention to prevent or delay the onset of the symptoms, complications, or biochemical indicia of a disease, alleviating the symptoms or arresting or inhibiting further development of the disease, condition, or disorder (e.g., autoimmune disease). Treatment may be prophylactic (to prevent or delay the onset of the disease, or to prevent the manifestation of clinical or subclinical symptoms thereof) or therapeutic suppression or alleviation of symptoms after the manifestation of the disease.

In general, the phrase "well tolerated" refers to the absence of adverse changes in health status that occur as a result of the treatment and would affect treatment decisions.

The term "lymphocyte" as used herein has the normal meaning in the art, and refers to any of the mononuclear, nonphagocytic leukocytes, found in the blood, lymph, and lymphoid tissues, i.e., B and T lymphocytes.

The phrase "subpopulations of T lymphocytes" or "T cell subset(s)" refers to T lymphocytes or T cells characterized by the expression of particular cell surface markers (see Barclay, A. N. et al. (eds.), 1997, THE LEUKOCYTE ANTIGEN FACTS BOOK, 2ND. EDITION, Academic Press, London, United Kingdom; this reference is herein incorporated by reference for all purposes).

The terms "cytotoxic T lymphocyte-associated antigen-4," "CTLA-4," "CTLA4," "CTLA-4 antigen" and "CD152" (see, e.g., Murata, 1999, *Am. J. Pathol.* 155:453–460) are used interchangeably, and include variants, isoforms, species homologs of human CTLA-4, and analogs having at least one common epitope with CTLA-4 (see, e.g., Balzano, 1992, *Int. J. Cancer Suppl.* 7:28–32).

The complete cDNA sequence of human CTLA-4 has the Genbank accession number L15006. The region of amino acids 1–37 is the leader peptide; 38–161 is the extracellular V-like domain; 162–187 is the transmembrane domain; and 188–223 is the cytoplasmic domain. Variants of the nucleotide sequence have been reported, including a G to A transition at position 49, a C to T transition at position 272, and an A to G transition at position 439. The complete DNA sequence of mouse CTLA-4 has the EMBL accession number X05719 (Brunet et al., 1987, *Nature* 328:267–270). The region of amino acids 1–35 is the leader peptide.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

An intact "antibody" comprises at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxyl-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) through cellular receptors such as Fc receptors (e.g., FcγRI, FcγRIIa, FcγRIIb, FcγRIII, and FcRη) and the first component (Clq) of the classical complement system. The term antibody includes antigen-binding portions of an intact antibody that retain capacity to bind the antigen. Examples of antigen binding portions include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CHI domains; (iv) a Fv fragment consisting of the VL and VH domains of a single arm of an antibody, (v) a dAb fragment (Ward et al., 1989 *Nature* 341:544–546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); See, e.g., Bird et al., 1988, *Science* 242:423–426; and Huston et al., 1988, *Proc. Natl. Acad. Sci. U.S.A.* 85:5879–5883). Such single chain antibodies are included by reference to the term "antibody" Fragments can be prepared by recombinant techniques or enzymatic or chemical cleavage of intact antibodies.

The term "human sequence antibody" includes antibodies having variable and constant regions (if present) derived from human immunoglobulin sequences. The human sequence antibodies of the invention may include amino acid residues not encoded by human germline immunoglobulin sequences (e.g., mutations introduced by random or site-specific mutagenesis in vitro or by somatic mutation in vivo). However, the term "human sequence antibody", as used herein, is not intended to include antibodies in which entire CDR sequences sufficient to confer antigen specificity and derived from the germline of another mammalian species, such as a mouse, have been grafted onto human framework sequences (i.e., humanized antibodies).

The terms "monoclonal antibody" or "monoclonal antibody composition" refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions (if present) derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "diclonal antibody" refers to a preparation of at least two antibodies to an antigen. Typically, the different antibodies bind different epitopes.

The term "oligoclonal antibody" refers to a preparation of 3 to 100 different antibodies to an antigen. Typically, the antibodies in such a preparation bind to a range of different epitopes.

The term "polyclonal antibody" refers to a preparation of more than 1 (two or more) different antibodies to an antigen. Such a preparation includes antibodies binding to a range of different epitopes.

The invention provides human sequence antibodies to a variety of antigens, including human antibodies to human CTLA-4, human G-CSF, human HSA, human CD4 and human EGFR. The human antibodies of this invention include antibodies which block or antagonize signals transduced by cell surface receptors such as the human CTLA-4 receptor and the human CD4 coreceptor. Some of these antibodies can bind to an epitope on human CTLA-4 so as to inhibit CTLA-4 from interacting with a human B7 counterreceptor. Similarly, some of the antibodies can bind to an epitope on human CD4 so as to inhibit CD4 from interacting with human class II MHC. Because interaction of human CTLA-4 with human B7 transduces a signal leading to inactivation of T-cells bearing the human CTLA-4 receptor, antagonism of the interaction effectively induces, augments or prolongs the activation of T cells bearing the human CTLA-4 receptor, thereby prolonging or augmenting an immune response. A "blocking antibody" refers to an antibody that reduces the binding of soluble human CTLA-4 to cell-expressed human B7 ligand by at least 10%, 20%, 30%, 40%, 50%, 60%, 70%, 80%, 90%, 99% or 99.9% under conditions in which the ratio of antibody combining site to human CTLA-4 ligand binding site is greater than 1:1 and the concentration of antibody is greater than $10^{-8}$ M.

The invention further provides human sequence IgA antibodies to a variety of human antigens. Exemplary IgA antibodies include CD4, G-CSF, CTLA-4 and EGFR. Because IgA antibodies can form dimers, such IgA antibodies can have improved cross-linking properties.

Other antibody preparations, sometimes referred to as multivalent preparations, bind to cell surface receptors such as human CTLA-4 in such a manner as to crosslink multiple human CTLA-4 receptors on the same cell.

Cross-linking can also be accomplished by combining soluble divalent antibodies having different epitope specificities. These polyclonal antibody preparations comprise at least two pairs of heavy and light chains binding to different epitopes on the antigen such that a signal can be transduced as a result of antibody-mediated crosslinking.

The term "recombinant human antibody" includes all human sequence antibodies of the invention that are prepared, expressed, created or isolated by recombinant means, such as antibodies isolated from an animal (e.g., a mouse) that is transgenic for human immunoglobulin genes (described further below); antibodies expressed using a recombinant expression vector transfected into a host cell, antibodies isolated from a recombinant, combinatorial human antibody library, or antibodies prepared, expressed, created or isolated by any other means that involves splicing of human immunoglobulin gene sequences to other DNA sequences. Such recombinant human antibodies have variable and constant regions (if present) derived from human germline immunoglobulin sequences. Such antibodies can, however, be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

A "heterohybrid antibody" refers to an antibody having a light and heavy chains of different organismal origins. For example, an antibody having a human heavy chain associated with a murine light chain is a heterohybrid antibody.

The term "substantially pure" or "isolated" means an object species (e.g. an antibody of the invention) has been identified and separated and/or recovered from a component of its natural environment such that the object species is the predominant species present (i.e., on a molar basis it is more abundant than any other individual species in the composition); a "substantially pure" or "isolated" composition also means where the object species comprises at least about 50 percent (on a molar basis) of all macromolecular species present. A substantially pure or isolated composition can also comprise more than about 80 to 90 percent by weight of all macromolecular species present in the composition. An isolated object species (e.g., antibodies of the invention) can also be purified to essential homogeneity (contaminant species cannot be detected in the composition by conventional detection methods) wherein the composition consists essentially of derivatives of a single macromolecular species. For example, an isolated antibody to human CTLA-4 can be substantially free of other antibodies that lack binding to human CTLA-4 and bind to a different antigen. Further, an isolated antibody that specifically binds to an epitope, isoform or variant of human CTLA-4 may, however, have cross-reactivity to other related antigens, e.g., from other species (e.g., CTLA-4 species homologs). Moreover, an isolated antibody of the invention be substantially free of other cellular material (e.g., non-immunoglobulin associated proteins) and/or chemicals.

"Specific binding" refers to preferential binding of an antibody to a specified antigen relative to other non-specified antigens. The phrase "specifically (or selectively) binds" to an antibody refers to a binding reaction that is determinative of the presence of the protein in a heterogeneous population of proteins and other biologics. Typically, the antibody binds with an association constant ($K_a$) of at least about $1\times10^6$ $M^{-1}$ or $10^7$ $M^{-1}$, or about $10^8$ $M^{-1}$ to $10^9$ $M^{-1}$, or about $10^{10}$ $M^{-1}$ to $10^{11}$ $M^{-1}$ or higher, and binds to the specified antigen with an affinity that is at least two-fold greater than its affinity for binding to a non-specific antigen (e.g., BSA, casein) other than the specified antigen or a closely-related antigen. The phrases "an antibody recognizing an antigen" and "an antibody specific for an antigen" are used interchangeably herein with the term "an antibody which binds specifically to an antigen". A predetermined antigen is an antigen that is chosen prior to the selection of an antibody that binds to that antigen.

The phrase "specifically bind(s)" or "bind(s) specifically" when referring to a peptide refers to a peptide molecule which has intermediate or high binding affinity, exclusively or predominately, to a target molecule. The phrases "specifically binds to" refers to a binding reaction which is determinative of the presence of a target protein in the presence of a heterogeneous population of proteins and other biologics. Thus, under designated assay conditions, the specified binding moieties bind preferentially to a particular target protein and do not bind in a significant amount to other components present in a test sample. Specific binding to a target protein under such conditions may require a binding moiety that is selected for its specificity for a particular target antigen. A variety of assay formats may be used to select ligands that are specifically reactive with a particular protein. For example, solid-phase ELISA immunoassays, immunoprecipitation, Biacore and Western blot are used to identify peptides that specifically react with the antigen. Typically a specific or selective reaction will be at least twice background signal or noise and more typically more than 10 times background.

The term "high affinity" for an antibody refers to an equilibrium association constant ($K_a$) of at least about $10^7M^{-1}$, at least about $10^8M^{-1}$, at least about $10^9M^{-1}$, at least about $10^{10}M^{-1}$, at least about $10^{11}M^{-1}$, or at least about $10^{12}M^{-1}$ or greater, e.g., up to $10^{13}M^{-1}$ or $10^{14}M^{-1}$ or greater. However, "high affinity" binding can vary for other antibody isotypes.

The term "$K_a$", as used herein, is intended to refer to the equilibrium association constant of a particular antibody-antigen interaction. This constant has units of 1/M.

The term "$K_d$", as used herein, is intended to refer to the equilibrium dissociation constant of a particular antibody-antigen interaction. This constant has units of M.

The term "$k_a$", as used herein, is intended to refer to the kinetic association constant of a particular antibody-antigen interaction. This constant has units of 1/Ms The term "$k_d$", as used herein, is intended to refer to the kinetic dissociation constant of a particular antibody-antigen interaction. This constant has units of 1/s.

"Particular antibody-antigen interactions" refers to the experimental conditions under which the equilibrium and kinetic constants are measured.

"Isotype" refers to the antibody class that is encoded by heavy chain constant region genes. Heavy chains are classified as gamma, mu, alpha, delta, or epsilon, and define the antibody's isotype as IgG, IgM, IgA, IgD and IgE, respectively. Additional structural variations characterize distinct subtypes of IgG (e.g., $IgG_1$, $IgG_2$, $IgG_3$ and $IgG_4$) and IgA (e.g., $IgA_1$ and $IgA_2$)

"Isotype switching" refers to the phenomenon by which the class, or isotype, of an antibody changes from one Ig class to one of the other Ig classes.

"Nonswitched isotype" refers to the isotypic class of heavy chain that is produced when no isotype switching has taken place; the CH gene encoding the nonswitched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human $\sigma_\mu$ and human $\Sigma_\mu$ ($\delta$-associated deletion). Alternative non-classical switching mechanisms, such as intertransgene and/or interchromosomal recombination, among others, may occur and effectuate isotype switching.

The term "switch sequence" refers to those DNA sequences responsible for switch recombination. A "switch donor" sequence, typically a μ switch region, are 5' (i.e., upstream) of the construct region to be deleted during the switch recombination. The "switch acceptor" region are between the construct region to be deleted and the replacement constant region (e.g., γ, ϵ, and alike). As there is no specific site where recombination always occurs, the final gene sequence is not typically predictable from the construct.

"Glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the non-human transgenic animal, when one of ordinary skill in the art would recognize the glycosylation pattern of the heterologous antibody as being more similar to said pattern of glycosylation in the species of the non-human transgenic animal than to the species from which the CH genes of the transgene were derived.

The term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "immunoglobulin locus" refers to a genetic element or set of linked genetic elements that comprise information that can be used by a B cell or B cell precursor to express an immunoglobulin peptide. This peptide can be a heavy chain peptide, a light chain peptide, or the fusion of a heavy and a light chain peptide. In the case of an unrearranged locus, the genetic elements are assembled by a B cell precursor to form the gene encoding an immunoglobulin peptide. In the case of a rearranged locus, a gene encoding an immunoglobulin peptide is contained within the locus.

The term "rearranged" refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus has at least one recombined heptamer/nonamer homology element.

The term "unrearranged" or "germline configuration" in reference to a V segment refers to the configuration wherein the V segment is not recombined so as to be immediately adjacent to a D or J segment.

The terms "nucleic acid" or "nucleic acid molecule" refer to a deoxyribonucleotide or ribonucleotide polymer in either single- or double-stranded form, and unless otherwise limited, can encompass known analogs of natural nucleotides that can function in a similar manner as naturally occurring nucleotides.

The term "isolated nucleic acid" in reference to nucleic acids encoding antibodies or antibody portions (e.g., VH, VL, CDR3) that bind to the antigen, is intended to refer to a nucleic acid in which the nucleotide sequences encoding the antibody or antibody portion are free of other nucleotide sequences encoding antibodies or antibody portions that bind antigens other than, for example, CTLA-4, which other sequences may naturally flank the nucleic acid in human genomic DNA.

The term "substantially identical," in the context of two nucleic acids or polypeptides refers to two or more sequences or subsequences that have at least about 80%, about 90%, about 95% or higher nucleotide or amino acid residue identity, when compared and aligned for maximum correspondence, as measured using the following sequence comparison method and/or by visual inspection. Such "substantially identical" sequences are typically considered to be homologous. The "substantial identity" can exist over a region of sequence that is at least about 50 residues in length, over a region of at least about 100 residues, or over a region at least about 150 residues, or over the fill length of the two sequences to be compared. As described below, any two antibody sequences can only be aligned in one way, by using the numbering scheme in Kabat. Therefore, for antibodies, percent identity has a unique and well-defined meaning.

Amino acids from the variable regions of the mature heavy and light chains of immunoglobulins are designated Hx and Lx respectively, where x is a number designating the position of an amino acid according to the scheme of Kabat, Sequences of Proteins of Immunological Interest (National Institutes of Health, Bethesda, Md., 1987 and 1991). Kabat lists many amino acid sequences for antibodies for each subgroup, and lists the most commonly occurring amino acid for each residue position in that subgroup to generate a consensus sequence. Kabat uses a method for assigning a residue number to each amino acid in a listed sequence, and this method for assigning residue numbers has become standard in the field. Kabat's scheme is extendible to other antibodies not included in his compendium by aligning the antibody in question with one of the consensus sequences in Kabat by reference to conserved amino acids. The use of the Kabat numbering system readily identifies amino acids at equivalent positions in different antibodies. For example, an amino acid at the L50 position of a human antibody occupies the equivalent position to an amino acid position L50 of a mouse antibody. Likewise, nucleic acids encoding antibody chains are aligned when the amino acid sequences encoded by the respective nucleic acids are aligned according to the Kabat numbering convention. An alternative structural definition has been proposed by Chothia, et al., 1987 *J. Mol. Biol.* 196:901–917; Chothia, et al., 1989, *Nature* 342:878–883; and Chothia, et al., *J. Mol. Biol.* 186:651–663 (1989) which is herein incorporated by reference for all purposes.

The phrase "selectively (or specifically) hybridizes to" refers to the binding, duplexing, or hybridizing of a molecule to a particular nucleotide sequence under stringent hybridization conditions when that sequence is present in a complex mixture (e.g., total cellular or library DNA or RNA), wherein the particular nucleotide sequence is detected at least at about 10 times background. In one embodiment, a nucleic acid can be determined to be within the scope of the invention by its ability to hybridize under stringent conditions to a nucleic acid otherwise determined to be within the scope of the invention (such as the exemplary sequences described herein).

The phrase "stringent hybridization conditions" refers to conditions under which a probe will hybridize to its target subsequence, typically in a complex mixture of nucleic acid, but not to other sequences in significant amounts (a positive signal (e.g., identification of a nucleic acid of the invention) is about 10 times background hybridization). Stringent conditions are sequence-dependent and will be different in different circumstances. Longer sequences hybridize specifically at higher temperatures. An extensive guide to the hybridization of nucleic acids is found in e.g., Sambrook, ed., MOLECULAR CLONING: A LABORATORY MANUAL (2ND ED.), Vols. 1–3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, PART I. Theory and Nucleic Acid Preparation, Tijssen, ed. Elsevier, N.Y. (1993).

Generally, stringent conditions are selected to be about 5–10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide as described in Sambrook (cited below). For high stringency hybridization, a positive signal is at least two times background, preferably 10 times background hybridization. Exemplary high stringency or stringent hybridization conditions include: 50% formamide, 5×SSC and 1% SDS incubated at 42° C. or 5× SSC and 1% SDS incubated at 65° C., with a wash in 0.2×SSC and 0.1% SDS at 65° C. For selective or specific hybridization, a positive signal (e.g., identification of a nucleic acid of the invention) is about 10 times background hybridization. Stringent hybridization conditions that are used to identify nucleic acids within the scope of the invention include, e.g., hybridization in a buffer comprising 50% formamide, 5×SSC, and 1% SDS at 42° C., or hybridization in a buffer comprising 5×SSC and 1% SDS at 65° C., both with a wash of 0.2×SSC and 0.1% SDS at 65° C. In the present invention, genomic DNA or cDNA comprising nucleic acids of the invention can be identified in standard Southern blots under stringent conditions using the nucleic acid sequences disclosed here. Additional stringent conditions for such hybridizations (to identify nucleic acids within the scope of the invention) are those which include a hybridization in a buffer of 40% formamide, 1 M NaCl, 1% SDS at 37° C.

However, the selection of a hybridization format is not critical—it is the stringency of the wash conditions that set forth the conditions which determine whether a nucleic acid is within the scope of the invention. Wash conditions used to identify nucleic acids within the scope of the invention include, e.g., a salt concentration of about 0.02 molar at pH 7 and a temperature of at least about 50° C. or about 55° C. to about 60° C.; or, a salt concentration of about 0.15 M NaCl at 72° C. for about 15 minutes; or, a salt concentration of about 0.2×SSC at a temperature of at least about 50° C. or about 55° C. to about 60° C. for about 15 to about 20 minutes; or, the hybridization complex is washed twice with a solution with a salt concentration of about 2×SSC containing 0.1% SDS at room temperature for 15 minutes and then washed twice by 0.1×SSC containing 0.1% SDS at 68° C. for 15 minutes; or, equivalent conditions. See Sambrook, Tijssen and Ausubel for a description of SSC buffer and equivalent conditions.

The term "sequence identity" refers to a measure of similarity between amino acid or nucleotide sequences, and can be measured using methods known in the art, such as those described below:

The terms "identical" or percent "identity," in the context of two or more nucleic acids or polypeptide sequences, refer to two or more sequences or subsequences that are the same or have a specified percentage of amino acid residues or nucleotides that are the same (i.e., 60% identity, preferably 65%, 70%, 75%, 80%, 85%, 90%, or 95% identity over a specified region, when compared and aligned for maximum correspondence over a comparison window, or designated region as measured using one of the following sequence comparison algorithms or by manual alignment and visual inspection.

The phrase "substantially identical," in the context of two nucleic acids or polypeptides, refers to two or more sequences or subsequences that have at least of at least 60%, often at least 70%, preferably at least 80%, most preferably at least 90% or at least 95% nucleotide or amino acid residue identity, when compared and aligned for maximum correspondence, as measured using one of the following sequence comparison algorithms or by visual inspection. Preferably, the substantial identity exists over a region of the sequences that is at least about 50 bases or residues in length, more preferably over a region of at least about 100 bases or residues, and most preferably the sequences are substantially identical over at least about 150 bases or residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of nucleic acids and proteins, the BLAST and BLAST 2.0 algorithms and the default parameters discussed below can be used.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, 1981, *Adv. Appl. Math.* 2: 482), by the homology alignment algorithm of Needleman & Wunsch, 1970, *J. Mol. Biol.* 48: 443, by the search for similarity method of Pearson & Lipman, 1988, *Proc. Natl. Acad. Sci. U.S.A.* 85: 2444, by computerized implementations of these algorithms (FASTDB (Intelligenetics), BLAST (National Center for Biomedical Information), GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., 1987 (1999 Suppl.), *Current Protocols in Molecular Biology,* Greene Publishing Associates and Wiley Interscience, N.Y.)

A preferred example of an algorithm that is suitable for determining percent sequence identity and sequence similarity is the FASTA algorithm, which is described in Pearson, W. R. & Lipman, D. J., 1988, *Proc. Natl. Acad Sci. U.S.A.* 85: 2444. See also W. R. Pearson, 1996, *Methods Enzymol.* 266: 227–258. Preferred parameters used in a FASTA alignment of DNA sequences to calculate percent identity are optimized, BL50 Matrix 15:−5, k-tuple=2; joining penalty=40, optimization=28; gap penalty−12, gap length penalty=−2; and width=16.

Another preferred example of algorithm that is suitable for determining percent sequence identity and sequence similarity are the BLAST and BLAST 2.0 algorithms, which are described in Altschul et al., 1977, *Nuc. Acids Res.* 25: 3389–3402 and Altschul et al., 1990, *J. Mol. Biol.* 215: 403–410, respectively. BLAST and BLAST 2.0 are used, with the parameters described herein, to determine percent sequence identity for the nucleic acids and proteins of the invention. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, *Proc. Natl. Acad. Sci. USA.* 89:10915) alignments (B) of 50, expectation (E) of 10, M=5, N=−4, and a comparison of both strands.

The BLAST algorithm also performs a statistical analysis of the similarity between two sequences (see, e.g., Karlin & Altschul, 1993, *Proc. Natl. Acad. Sci. U.S.A.* 90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, 1987, *J. Mol. Evol.* 35: 351–360. The method used is similar to the method described by Higgins & Sharp, 1989, *CABIOS* 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984, Nuc. Acids Res. 12: 387–395.

Another preferred example of an algorithm that is suitable for multiple DNA and amino acid sequence alignments is the CLUSTALW program (Thompson, J. D. et al., 1994, *Nucl. Acids. Res.* 22: 4673–4680). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, 1992, *Proc. Natl. Acad. Sci. U.S.A.* 89: 10915–10919).

The nucleic acids of the invention be present in whole cells, in a cell lysate, or in a partially purified or substantially pure form. A nucleic acid is “isolated” or “rendered substantially pure” when purified away from other cellular components or other contaminants, e.g., other cellular nucleic acids or proteins, by standard techniques, including alkaline/SDS treatment, CsCl banding, column chromatography, agarose gel electrophoresis and others well known in the art (See, e.g., Sambrook, Tijssen and Ausubel discussed herein and incorporated by reference for all purposes). The nucleic acid sequences of the invention and other nucleic acids used to practice this invention, whether RNA, cDNA, genomic DNA, or hybrids thereof, may be isolated from a variety of sources, genetically engineered, amplified, and/or expressed recombinantly. Any recombinant expression system can be used, including, in addition to bacterial, e.g., yeast, insect or mammalian systems. Alternatively, these nucleic acids can be chemically synthesized in vitro. Techniques for the manipulation of nucleic acids, such as, e.g., subcloning into expression vectors, labeling probes, sequencing, and hybridization are well described in the scientific and patent literature, see, e.g., Sambrook, Tijssen and Ausubel. Nucleic acids can be analyzed and quantified by any of a number of general means well known to those of skill in the art. These include, e.g., analytical biochemical methods such as NMR, spectrophotometry, radiography, electrophoresis, capillary electrophoresis, high performance liquid chromatography (HPLC), thin layer chromatography (TLC), and hyperdiffusion chromatography, various immunological methods, such as fluid or gel precipitin reactions, immunodiffusion (single or double), immunoelectrophoresis, radioimmunoassays (RIAs), enzyme-linked immunosorbent assays (ELISAs), immuno-fluorescent assays, Southern analysis, Northern analysis, dot-blot analysis, gel electrophoresis (e.g., SDS-PAGE), RT-PCR, quantitative PCR, other nucleic acid or target or signal amplification methods, radiolabeling, scintillation counting, and affinity chromatography.

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

A "label" is a composition detectable by spectroscopic, photochemical, biochemical, immunochemical, or chemical means. For example, useful labels include $^{32}P$, fluorescent dyes, electron-dense reagents, enzymes (e.g., as commonly used in an ELISA), biotin, digoxigenin, or haptens and proteins for which antisera or monoclonal antibodies are available (e.g., the polypeptides of the invention can be made detectable, e.g., by incorporating a radiolabel into the peptide, and used to detect antibodies specifically reactive with the peptide).

The term "sorting" in the context of cells as used herein to refers to both physical sorting of the cells, as can be accomplished using, e.g., a fluorescence activated cell sorter, as well as to analysis of cells based on expression of cell surface markers, e.g., FACS analysis in the absence of sorting.

The phrase "immune cell response" refers to the response of immune system cells to external or internal stimuli (e.g., antigen, cytokines, chemokines, and other cells) producing biochemical changes in the immune cells that result in immune cell migration, killing of target cells, phagocytosis, production of antibodies, other soluble effectors of the immune response, and the like.

The terms "T lymphocyte response" and "T lymphocyte activity" are used here interchangeably to refer to the component of immune response dependent on T lymphocytes (i.e., the proliferation and/or differentiation of T lymphocytes into helper, cytotoxic killer, or suppressor T lymphocytes, the provision of signals by helper T lymphocytes to B lymphocytes that cause or prevent antibody production, the killing of specific target cells by cytotoxic T lymphocytes, and the release of soluble factors such as cytokines that modulate the function of other immune cells).

The term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

Components of an immune response may be detected in vitro by various methods that are well known to those of ordinary skill in the art. For example, (1) cytotoxic T lymphocytes can be incubated with radioactively labeled target cells and the lysis of these target cells detected by the release of radioactivity, (2) helper T lymphocytes can be incubated with antigens and antigen presenting cells and the synthesis and secretion of cytokines measured by standard methods (Windhagen, A. et al., 1995, *Immunity* 2:373–80), (3) antigen presenting cells can be incubated with whole protein antigen and the presentation of that antigen on MHC detected by either T lymphocyte activation assays or biophysical methods (Harding et al., 1989, *Proc. Natl. Acad. Sci. USA.,* 86:4230–4), (4) mast cells can be incubated with reagents that cross-link their Fc-epsilon receptors and histamine release measured by enzyme immunoassay (Siraganian, et al., 1983, *TIPS* 4:432–437).

Similarly, products of an immune response in either a model organism (e.g., mouse) or a human patient can also be detected by various methods that are well known to those of ordinary skill in the art. For example, (1) the production of antibodies in response to vaccination can be readily detected by standard methods currently used in clinical laboratories, e.g., an ELISA; (2) the migration of immune cells to sites of inflammation can be detected by scratching the surface of skin and placing a sterile container to capture the migrating cells over scratch site (Peters et al., 1988, *Blood* 72:1310–5); (3) the proliferation of peripheral blood mononuclear cells in response to mitogens or mixed lymphocyte reaction can be measured using 3H-thymidine; (4) the phagocytic capacity of granulocytes, macrophages, and other phagocytes in PBMCs can be measured by placing PMBCs in wells together with labeled particles (Peters et al., 1988); and (5) the differentiation of immune system cells can be measured by labeling PBMCs with antibodies to CD molecules such as CD4 and CD8 and measuring the fraction of the PBMCs expressing these markers.

As used herein, the phrase “signal transduction pathway” or “signal transduction event” refers to at least one biochemical reaction, but more commonly a series of biochemical reactions, which result from interaction of a cell with a stimulatory compound or agent. Thus, the interaction of a stimulatory compound with a cell generates a “signal” that is transmitted through the signal transduction pathway, ultimately resulting in a cellular response, e.g., an immune response described above.

A signal transduction pathway refers to the biochemical relationship between a variety of signal transduction molecules that play a role in the transmission of a signal from one portion of a cell to another portion of a cell. As used herein, the phrase “cell surface receptor” includes molecules and complexes of molecules capable of receiving a signal and the transmission of such a signal across the plasma membrane of a cell. An example of a “cell surface receptor” of the present invention is the T cell receptor (TCR) or the B7 ligands of CTLA-4.

A signal transduction pathway in a cell can be initiated by interaction of a cell with a stimulator that is inside or outside of the cell. If an exterior (i.e., outside of the cell) stimulator (e.g., an MHC-antigen complex on an antigen presenting cell) interacts with a cell surface receptor (e.g., a T cell receptor), a signal transduction pathway can transmit a signal across the cell’s membrane, through the cytoplasm of the cell, and in some instances into the nucleus. If an interior (e.g., inside the cell) stimulator interacts with an intracellular signal transduction molecule, a signal transduction pathway can result in transmission of a signal through the cell’s cytoplasm, and in some instances into the cell’s nucleus.

Signal transduction can occur through, e.g., the phosphorylation of a molecule; non-covalent allosteric interactions; complexing of molecules; the conformational change of a molecule; calcium release; inositol phosphate production; proteolytic cleavage; cyclic nucleotide production and diacylglyceride production. Typically, signal transduction occurs through phosphorylating a signal transduction molecule.

The term “nonspecific T cell activation” refers to the stimulation of T cells independent of their antigenic specificity.

General

To achieve improved stability of the human kappa light chain locus, the trans-chromosome technology was combined with earlier pronuclear microinjection technology for generating trangenic animals. The human kappa light chain locus transgene KCo5 (Fishwild, D. et al., 1996, *Nat. Biotechnol.* 14:845–851; U.S. Pat. No. 5,770,429) includes a substantial portion of the human kappa locus, and is stably maintained in the mouse germline and in B cells and hybridoma cells expressing human kappa chains derived from the transgene. This transgene was combined with the stable hCF(SC20) transchromosome, together with functional inactivation mutations of the endogenous mouse heavy and kappa light chain loci, to generate animals expressing a broad human antibody repertoire including multiple human heavy chain isotypes. Thus, improved stability of the light chain transgene, relative to the double-TC/KO mice (Tomizuka, K. et al., 2000, *Proc. Natl. Acad. Sci. U.S.A.* 97:722–727) provides for the recovery of a larger number of hybridomas from each fusion.

The invention provides for the isolation of fully human antibodies of any desired heavy chain isotype, including $IgA_1$, $IgA_2$, IgD, IgE, $IgG_1$, IgG2, $IgG_3$, $IgG_4$, and IgM. In particular, several different antibodies having high affinity to predeterninned antigens can be isolated from a single transgenic nonhuman mammal.

A transgenic non-human mammal of the present invention, preferably a mouse or other rodent, can also be generated using deposited material. Chicken DT40 cells retaining hCF(SC20) have been deposited under the Budapest treaty on May 9, 2001 in the International Patent Organism Depository, National Institute of Advanced Industrial Science and Technology, Tsukuba Central 6, 1-1,Higashi 1-Chome Tsukuba-shi, Ibaraki-ken, 305-8566 Japan. The depository number is FERM BP-7583. The cell line name was assigned as SC20.

Chicken DT40 cells retaining hCF(SC20) have also been deposited in the Food Industry Research and Development Institute (FIRDI) in Taiwan, on Aug. 18, 1999. The depository number is CCRC 960099. The cell line name was assigned as SC20(D), on Taiwan deposition. The hCF (SC20) retained in chicken DT-40 cells can be transferred into mouse ES cells as described in WO 00/10383 (EP 1106061). Briefly, microcells are generated from chicken DT-40 cells and fused with CHO cells. Then CHO cells retaining the hCF(SC20) can be selected based on G418 resistance. Retention of the hCF(SC20) can be confirmed by PCR or FISH analysis using commercially available human COT1 DNA or human chromosome 14-specific probe. Thereafter, microcells are generated from the CHO cells retaining the hCF(SC20) and fused with mouse ES cells. ES cells retaining the hCF(SC20) can be selected in the same way of CHO cells.

Cells retaining the KCo5 transgene DNA have been deposited with the American Type Culture Collection (ATCC), 10801 University Boulevard, Manassas, Va. 20110-2209 under the Budapest Treaty and given the Accession Nos. indicated on Nov. 8, 2001: 17E1 in yeast (YAC y17, Medarex KCo5) assigned ATCC No. PTA-3842 (the genetic material is a Yeast Artificial Chromosome containing an insert of the human immunoglobulin kappa variable region gene locus); pKV4 in *E. coli* (Medarex KCo5), assigned ATCC No. PTA-3843 (plasmid containing human immunoglobulin variable region genes); pKCIB in *E. coli* (Medarex KCo5) assigned ATCC No. PTA-3844 (plasmid containing human immunoglobulin J kappa and kappa constant region genes).

Cells retaining the DNAs that KCo5 transgene have also been deposited in the Food Industry Research and Development Institute (FIRDI) in Taiwan, on Nov. 22, 2001. The depository numbers for pKV4, YACy17 and pKCIB are: CCRC 940383, CCRC 940385, and CCRC 940386, respectively.

Transgene KCo5 can be transferred into mouse cells as described previously (Fishwild, D. ibid, see also Example 38 in U.S. Pat. No. 5,770,429; see also Example 2 below).

General Characteristics of Immunoglobulins

The basic antibody structural unit is known to comprise a tetramer of subunits. Each tetramer is composed of two identical pairs of polypeptide chains, each pair having one "light" (about 25 kDa) and one "heavy" chain (about 50–70 kDa). The amino-terminal portion of each chain includes a variable region of about 100 to 110 or more amino acids primarily responsible for antigen recognition. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 1–10 more amino acids. (See generally, *Fundamental Immunology* (Paul, W., ed., 2nd ed. Raven Press, N.Y., 1989), Ch. 7 (incorporated by reference in its entirety for all purposes).

The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901–917 (1987); Chothia et al., *Nature* 342:878–883 (1989).

The Natural Human Immunoglobulin Loci

Human immunoglobulins are naturally encoded by three distinct loci: heavy chain, kappa light chain and lambda light chain. These natural loci are located on chromosomes 14, 2, and 22 respectively. The natural human heavy chain locus, located at 14q32.3, near the telomere of the long arm of human chromosome 14, extends over approximately 1.3 megabases and encodes approximately 45 expressed V gene segments, 27 D gene segments, 6 J gene segments and 9 constant (C) region gene segments. The natural human kappa light chain locus, located at 2p11.12 on chromosome 2, extends over approximately 1.8 megabases, and comprises approximately 34 expressed V gene segments, 5 J gene segments, and a single C region gene segment. The natural human lambda locus, located 22q11.2, extends over approximately 0.9 megabases and encodes approximately 30 V gene segments, and 4 functional J-C pairs, each comprising a single J gene segment and a single C gene segment. Each of these natural loci can also comprise deletions, insertions, and single nucleotide polymorphisms.

Production of Monoclonal Antibodies by Hybridoma Fusion

The production of monoclonal antibodies can be accomplished by, for example, immunizing the animal with an antigen (e.g., a human protein antigen such as CD4, G-CSF, HSA, EGFR, or CTLA-4, a pathogen encoded antigen, a toxin, or other antigen). A longer polypeptide comprising the antigen or an immunogenic fragment of the antigen or anti-idiotypic antibodies to an antibody to the antigen can also be used. See Harlow & Lane, *Antibodies, A Laboratory Manual* (CSHP New York, N.Y., 1988) and Mishell and Shiigi, *Selected Methods in Cellular Immunology,* (W.H. Freeman and Co. New York, N.Y. 1980) (both references are incorporated by reference for all purposes). Such an immunogen can be obtained from a natural source, by peptide synthesis or by recombinant expression. Optionally, the immunogen can be administered attached or otherwise complexed with a carrier protein, as described below. Optionally, the immunogen can be administered with an adjuvant. Several types of adjuvant can be used as described below. Complete Freund's adjuvant followed by incomplete adjuvant is preferred for immunization of laboratory animals. Rabbits or guinea pigs are typically used for making polyclonal antibodies. Rodents (e.g., mice, rats, and hamsters) are typically used for making monoclonal antibodies. These mice can be transgenic, and can comprise human immunoglobulin gene sequences, as described below. After immunization, the immunized animals will develop a serum response to the introduced immunogen. This serum response can be measured by titration of collected serum using a variety of different assays. An example of a commonly used assay is an ELISA. The magnitude of the serum response is commonly referred to as the titer. For example, a titer of 1,000 indicates that the presence of reactive antibodies can be detected by assay of a 1,000 fold dilution of the serum. Typically, immunization will result in a serum response several orders of magnitude greater than that found in unimmunized animals. Serum responses of only one or two orders of magnitude are considered weak, and typically indicate the presence of few B cells expressing antigen reactive antibodies. Monoclonal antibodies are routinely obtained by fusing lymphocytes with immortalized cells (e.g., myeloma cells) to form hybrid cells, referred to as hybridoma cells. The newly formed hybridoma cells derive antibody expression properties from the parental lymphocytes, and growth properties from the parental immortalized cells. Newly formed hybridoma cells are grown in culture dishes (e.g., 96 well plates) comprising culture medium. The culture supernatant is tested (typically between one and two weeks after fusion) for the presence of antigen reactive antibodies of the desired heavy and light chain isotype. The cells in this primary culture are then diluted and replated to isolate individual clones of hybridoma cells secreting a single species of monoclonal antibody. This secondary culture can be further subcloned to obtain tertiary cultures, and so forth. The fraction of antigen reactive primary cultures that can be used to obtain hybridoma clones by this process of subcloning provides a measure of the subcloning efficiency. If all of the antigen positive primary hybridoma cultures can be used to derive cloned cell lines, then the subcloning efficiency is 100%. If the immunoglobulin loci that encode the expressed antibodies are unstable, e.g., easily lost during cell division—either through loss of a chromosome, chromosome fragment, or transchromosome, or through deletional recombination of an inserted array, or through some other mechanism—then the subcloning efficiency will be reduced (i.e., less than 100%). It is particularly useful to have a platform for deriving monoclonal antibodies where the subcloning efficiency is high (e.g., greater than 20%, preferably greater than 50%, more preferably greater than 80%, most preferably greater than 90% or 95%). Antibodies are screened for specific binding to the antigen. Optionally, antibodies are further screened for binding to a specific region of the antigen. For protein antigens, the latter screening can be accomplished by determining binding of an antibody to a collection of deletion mutants of a the antigen peptide and determining which deletion mutants bind to the antibody. Binding can be assessed, for example, by Western blot or ELISA. The smallest fragment to show specific binding to the antibody defines the epitope of the antibody. However, some epitopes comprise non-contiguous structural elements that can be lost by deletion of elements outside of the actual epitope. Alternatively, epitope specificity can be determined by a competition assay is which a test and reference antibody compete for binding to the antigen. If the test and reference antibodies compete, then they bind to the same epitope or epitopes sufficiently proximal that binding of one antibody interferes with binding of the other.

Cloning Nucleic Acids Encoding Antibodies From B Cells Hybridomas

Nucleic acids encoding at least the variable regions of heavy and light chains can be cloned from either immunized or naive transgenic animals. Nucleic acids can be cloned as genomic or cDNA from lymphatic cells of such animals. No immortalization of such cells is required prior to cloning of immunoglobulin sequences. Usually, mRNA is isolated and amplified by reverse transcription with oligo-dT primers. The cDNA is then amplified using primers to conserved regions of human immunoglobulins. The libraries can be easily enriched for non-mu isotypes using a 3' primer specific for non-mu sequences (e.g., IgG or IgA) Typically, the amplified population of light chains comprises at least 100, 1000, 10,000, 100,000 or 1,000,000 different light chains. Likewise, the amplified population of heavy chains comprises at least 100, 1000, 10,000, 100,000 or 1,000,000 different heavy chains. For example, using IgG primers, typically at least 90, 95 or 99% of amplified heavy chains are of IgG isotype. Nucleic acids encoding at least the variable regions of heavy and light chains can also be cloned from hybridomas mentioned above, by various well-known methods such as PCR or screening cDNA library by DNA probe specific for conserved regions of human antibodies. Nucleic acids encoding antibody chains to be subcloned can be excised by restriction digestion of flanking sequences or can be amplified by PCR using primers to sites flanking the coding sequences. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila, et al., 1991, *Nucleic Acids Res.* 19:967; Eckert, et al., 1991, *PCR Methods and Applications* 1: 17; PCR (eds. McPherson et al., IRL Press, Oxford). These references and references cited therein are herein incorporated by reference for all purposes.

Recombinant Expression of Antibodies

Nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

*E. coli* is one procaryotic host particularly for expressing antibodies of the present invention. Other microbial hosts suitable for use include bacilli, such as *Bacillus subtilus*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

Mammalian tissue cell culture can also be used to express and produce the antibodies of the present invention (See Winnacker, *From Genes to Clones* (VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CVI line transformed by SV40 (COS-7, ATCC CRL 1651); human embryonic kidney line (293) (Graham et al., 1977, *J. Gen. Virol.* 36:59); baby hamster kidney cells (BHK, ATCC CCL 10); Chinese hamster ovary-cells-DHFR (CHO, Urlaub and Chasin, 1980, *Proc. Natl. Acad. Sci. USA.* 77:4216); mouse sertoli cells (TM4, Mather, 1980, *Biol. Reprod.* 23:243–251); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,HB 8065); mouse mammary tumor (MMT 060562, ATCC CCL51); and, TRI cells (Mather et al., 1982, *Annals N.Y. Acad. Sci.* 383:44–46); baculovirus cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts. (See generally Sambrook et al., *Molecular Cloning: A Laboratory Manual* (Cold Spring Harbor Press, 2nd ed., 1989) (incorporated by reference in its entirety for all purposes). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (See generally Scopes, *Protein Purification* (Springer-Verlag, N.Y., 1982). Substantially pure inmunoglobulins of at least about 90 to 95% homogeneity are preferred, and 98 to 99% or more homogeneity most preferred.

Chimeric and Humanized Antibodies

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $IgG_1$ and $IgG_4$. Human isotype $IgG_1$ is preferred. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody (referred to as the donor immunoglobulin). See, Queen et al., 1989, *Proc. Natl. Acad. Sci. U.S.A.* 86:10029–10033 and WO 90/07861, U.S. Pat. Nos. 5,693,762, 5,693,761, 5,585,089, 5,530,101 and Winter, U.S. Pat. No. 5,225,539 (incorporated by reference in their entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid:

(1) noncovalently binds antigen directly, (2) is adjacent to a CDR region, (3) otherwise interacts with a CDR region (e.g. is within about 6 A of a CDR region), or (4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Human Antibodies

Human antibodies directed against specific antigens are provided by a variety of techniques described below. Some human antibodies are selected by competitive binding experiments, or otherwise, to have the same epitope specificity as a particular mouse antibody, such as one of the mouse monoclonals described in the Examples. Human antibodies can also be screened for a particular epitope specificity by using only a fragment of the antigen as the immunogen, and/or, in the case of protein antigens, by screening antibodies against a collection of deletion mutants of the antigen.

Trioma Methodology

The basic approach and an exemplary cell fusion partner, SPAZ-4, for use in this approach have been described by Oestberg et al., 1983, *Hybridoma* 2:361–367; Oestberg, U.S. Pat. No. 4,634,664; and Engleman et al., U.S. Pat. No. 4,634,666 (each of which is incorporated by reference in its entirety for all purposes). The antibody-producing cell lines obtained by this method are called triomas, because they are descended from three cells—two human and one mouse. Initially, a mouse myeloma line is fused with a human B-lymphocyte to obtain a non-antibody-producing xenogeneic hybrid cell, such as the SPAZ-4 cell line described by Oestberg, supra. The xenogeneic cell is then fused with an immunized human B-lymphocyte to obtain an antibody-producing trioma cell line. Triomas have been found to produce antibody more stably than ordinary hybridomas made from human cells.

Although triomas are genetically stable they do not produce antibodies at very high levels. Expression levels can be increased by cloning antibody genes from the trioma into one or more expression vectors, and transforming the vector into standard mammalian, bacterial or yeast cell lines.

Transgenic Non-human Mammals

Human antibodies against a variety of antigens can also be produced from non-human transgenic mammals comprising human immunoglobulin loci. Typically these immunoglobulin loci can encode substantially human sequence antibodies, preferably 95% or more identical to human sequences, more preferably 98–99% or more identical, and most preferably 100% identical. The immunoglobulin loci can be rearranged or unrearranged, and can comprise deletions or insertions relative to the natural human immunoglobulin loci. The loci can include genetic elements (e.g., non-coding elements such as enhancers, promoters, and switch sequences, or coding elements such as mu constant region gene segments) from other species, and from non-immunoglobulin loci, that do not contribute substantially to the coding portion of secondary repertoire (non IgM) antibodies. Preferred human immunoglobulin loci undergo DNA sequence alterations including V(D)J joining, heavy chain class switching, and somatic mutation in lymphoid cell and/or lymphoid cell precursors in the non-human transgenic mammal to produce high affinity human antibodies to predetermined antigens. The human immunoglobulin loci contained in these transgenic mammals preferably include unrearranged sequences of natural human heavy and human light chain loci. Usually, the endogenous immunoglobulin locus of such transgenic mammals is functionally inactivated (U.S. Pat. No. 5,589,369; Takeda, S. et al., 1993, *EMBO J.* 12:2329–2366; Jakobovits, A., et al., 1993, *Proc.*

*Natl. Acad. Sci. U.S.A.* 90:2551–2555; Kitamura, D. and Rajewsky, K., 1992, *Nature* 356: 154–156; Gu, H. et al., 1991, *Cell* 65:47–54; Chen, J. et al., *EMBO J.* 12:821–830; Sun, W. et al., 1994, *J. Immunol* 152:695–704; Chen, J. et al., 1993, *Intl. Immunology* 5:647–656; Zou, X. et al., 1995, *Eur. J. Immunol* 25:2154–2162; Chen, J. et al., 1993 *Intl. Immunology* 5:647–656; Boudinot, P., et al, 1995, *Eur. J. Immunol.* 25:2499–2505; Chen, J. et al., 1993, *Proc. Natl. Acad. Sci.* 90:4528–4532; Roes, J. and Rajewsky, K., 1991, *Intl. Immunology* 3:1367–1371; Gu, H. et al., 1993, *Cell* 73:1155–1164; Taki, S. et al., 1993, *Science* 262: 1268–71; Kitamura, D. et al., 1991, *Nature* 350:423–6; Lutz, C. et al., 1998, *Nature* 393:797–801; Zou, Y. et al, 1994, *Current Biology* 4: 1099–1103; Chen, J. et al., 1993, *EMBO J.* 12:4635–4645; Serwe, M. and Sablitzky, F., 1993, *EMBO J.* 12:2321–2327; Sanchez, P. et al., 1994, *Intl. Immunology* 6:711–719; Zou, Y. et al., 1993, *EMBO J.* 12:811–820). Inactivation of endogenous immunoglobulin genes preferably can be achieved, e.g., by targeted homologous recombination. The exogenous human immunoglobulin loci can be associated the endogenous mouse chromosomes or can be of (e.g., part of, inserted within or attached to) an introduced transchromosome. Transchromosomes are introduced into a cell as a nonendogenous chromosome or chromosome fragment having a centromere and two telomeres. These transchromosomes commonly comprise telomere and centromere sequences and can comprise deletions relative to the parental intact chromosome. Transchromosomes can also comprise additional inserted sequences. For example, two human immunoglobulin loci can be combined onto a single transchromosome by inserting sequences of a first immunoglobulin locus (e.g. from a YAC clone, a transchromosome, or an intact chromosome) into a transchromosome comprising a second immunoglobulin locus. This process can also be repeated to combine all three human immunoglobulin loci onto a single transchromosome. A single transchromosome comprising two or three different immunoglobulin loci provides for genetic linkage of these loci which increases the fraction of transgenic offspring that are useful for making human antibodies. Preferred forms of transchromosomes are those described in detail in Tomizuka, K. et al., 2000, *Proc. Natl. Acad. Sci. U.S.A.* 97:722–727, Tomizuka, K. et al., 1997, *Nature Genetics* 16:133–143, and WO 97/07671, WO 98/37757 and WO 00/10383, each of which is incorporated by reference in its entirety for all purposes. Transchromosomes can also include integrated selectable markers (e.g. neomycin resistance genes) and other sequences not found in the parent intact chromosome. In the event of recombination between a transchromosome and an endogenous mouse chromosome, sequences from the transchromosome are inserted or added to the endogenous mouse chromosome. Transchromosomes can be modified by deletion, translocation, substitution and the like, as described in WO 98/37757, EP 0972445 and WO 00/10383, which are incorporated herein by reference for all purposes. For example, transchromosomes can be fragmented spontaneously in the course of introduction into mouse embryonic stem (ES) cells, fragmented by telomere-directed truncation and/or translocated by Cre/loxP site-specific recombination or similar methods. Such recombination or translocation events can be promoted by specifically inserting recombination sites (e.g., loxP sequences and others; see, e.g., Abuin, A. and Bradley, A., 1996, *Mol. Cell Biol.* 16: 1851–1856; Mitani, K. et al., 1995, *Somat. Cell. Mol. Genet.* 21:221–231; Li, Z. W. et al., 1996, *Proc. Natl. Acad. Sci. U.S.A.* 93:6158–6162; Smith, A J. et al., 1995, *Nat. Genet.* 9:376–385; Trinh, K R. and Morrison, S. L., 2000, *J. Immunol. Methods* 244:185–193; Sunaga, S. et al., 1997, *Mol. Reprod Dev.* 46: 109–113; Dymecki, S. M., 1996, *Proc. Natl. Acad Sci. U.S.A.* 93:6191–6196; Zou, Y R. et al., 1994, *Curr. Biol.* 4: 1099–1103; Rudolph, U. et al., 1993, *Transgenic Res.* 2:345–355; Rickert, R. C. et al., 1997, *Nucleic Acids Res.* 25:1317–1318). In the case of introduced loxP sites, expression of a transgene encoding the cre recombinase will promote recombination between the two loxP sites. Transchromosomes can also be a fusion chromosome consisting of different chromosome fragments as a result of the translocation described above. Transchromosomes can be autonomous. Autonomous transchromosomes are distinct from, are noncontiguous with, and are not inserted into the endogenous mouse chromosomes. These autonomous transchromosomes comprise telomere and centromere sequences that enable autonomous replication. Alternatively, transchromosome sequences can be translocated to mouse chromosomes after introduction into mouse cell nuclei. The endogenous mouse chromosomes include 19 autosomal chromosome pairs and the X and Y chromosomes.

Introduction of exogenous human immunoglobulin loci can be achieved by a variety of methods including, for example, microinjection of half-day embryo pronuclei, transfection of embryonic stem cells, or fusion of embryonic stem cells with yeast spheroplasts or micronuclei comprising transchromosomes. The transgenic mammals resulting from the processes described above are capable of functionally rearranging the introduced exogenous immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO 93/12227 (1993); U.S. Pat. Nos. 5,877,397, 5,874,299, 5,814,318, 5,789,650, 5,770,429, 5,661,016, 5,633,425, 5,625,126, 5,569,825, 5,545,806, *Nature* 48:1547–1553 (1994), *Nature Biotechnology* 14, 826 (1996), Kucherlapati, WO 91/10741 (1991), WO 94/02602 (1993), WO 96/34096 (1995), WO 96/33735 (1996), WO 98/24893 (1997), U.S. Pat. Nos. 5,939,598, 6,075,181, 6,114,598, Tomizuka, K. et al., 2000, *Proc. Natl. Acad. Sci. U.S.A.* 97:722–727, Tomizuka, K. et al., 1997, *Nature Genetics* 16:133–143, and Tomizuka, K., WO 97/07671, WO 98/37757, WO 00/10383, and JP 2000-42074 (each of which is incorporated by reference in its entirety for all purposes). Transgenic nonhuman mammals such as rodents are particularly suitable. Monoclonal antibodies can be prepared, e.g., by fusing B-cells from such mammals to suitable immortal cell lines using conventional Kohler-Milstein technology. Monoclonal antibodies can also be accessed directly from individual B cells, isolated from the medium, using PCR amplification of V regions (Schrader et al., 1997, U.S. Pat. No. 5,627,052). Alternatively, FACs sorted, or otherwise enriched B cell preparations can be used as a source of RNA or DNA for PCR amplification of V region sequences. Phage display methods (described below) can also be used to obtain human antibody sequences from immunized transgenic mice comprising human immunoglobulin loci. The human antibody V region sequences obtained by these methods can then be used to generate intact antibodies that retain the binding characteristics of the original parent antibodies. This process is described below.

Phage Display Methods

A further approach for obtaining human antibodies is to screen a cDNA library from B cells according to the general protocol outlined by Huse et al., 1989, *Science* 246:1275–1281. Such B cells can be obtained from a human immunized with the desired antigen, fragments, longer polypeptides containing the antigen or fragments or anti-idiotypic antibodies. Optionally, such B cells are obtained from an individual who has not been exposed to the antigen. B cell can also be obtained from transgenic non-human animals expressing human immunoglobulin sequences. The transgenic non-human animals can be immunized with an antigen or collection of antigens. The animals can also be unimmunized. B cell mRNA sequences encoding human antibodies are used to generate cDNA using reverse transcriptase. The V region encoding segments of the cDNA sequences are then cloned into a DNA vector that directs expression of the antibody V regions. Typically the V region sequences are specifically amplified by PCR prior to cloning. Also typically, the V region sequences are cloned into a site within the DNA vector that is constructed so that the V region is expressed as a fusion protein. Examples of such fusion proteins include ml 3 coliphage gene 3 and gene 8 fusion proteins. The collection of cloned V region sequences is then used to generate an expression library of antibody V regions. To generate an expression library, the DNA vector comprising the cloned V region sequences is used to transform eukaryotic or prokaryotic host cells. In addition to V regions, the vector can optionally encode all or part of a viral genome, and can comprise viral packaging sequences. In some cases the vector does not comprise an entire virus genome, and the vector is then used together with a helper virus or helper virus DNA sequences. The expressed antibody V regions are found in, or on the surface of, transformed cells or virus particles from the transformed cells. This expression library, comprising the cells or virus particles, is then used to identify V region sequences that encode antibodies, or antibody fragments reactive with predetermined antigens. To identify these V region sequences, the expression library is screened or selected for reactivity of the expressed V regions with the predetermined antigens. The cells or virus particles comprising the cloned V region sequences, and having the expressed V regions, are screened or selected by a method that identifies or enriches for cells or virus particles that have V regions reactive (e.g., binding association or catalytic activity) with a predetermined antigen. For example, radioactive or fluorescent labeled antigen that then binds to expressed V regions can be detected and used to identify or sort cells or virus particles. Antigen bound to a solid matrix or bead can also be used to select cells or virus particles having reactive V regions on the surface. The V region sequences thus identified from the expression library can then be used to direct expression, in a transformed host cell, of an antibody or fragment thereof, having reactivity with the predetermined antigen. The protocol described by Huse is rendered more efficient in combination with phage-display technology. See, e.g., Dower et al., WO 91/17271 and McCafferty et al., WO 92/01047, U.S. Pat. Nos. 5,871,907, 5,858,657, 5,837,242, 5,733,743 and 5,565,332 (each of which is incorporated by reference in its entirety for all purposes). In these methods, libraries of phage are produced in which members (display packages) display different antibodies on their outer surfaces. Antibodies are usually displayed as Fv or Fab fragments. Phage displaying antibodies with a desired specificity can be selected by affinity enrichment to the antigen or fragment thereof. Phage display combined with immunized transgenic non-human animals expressing human immunoglobulin genes can be used to obtain antigen specific antibodies even when the immune response to the antigen is weak.

In a variation of the phage-display method, human antibodies having the binding specificity of a selected murine antibody can be produced. See, for example, Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for CTLA-4 (e.g., at least $10^8$ and preferably at least $10^9$ $M^{-1}$) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for the selected are selected. Artificial antibodies that are similar to human antibodies can be obtained from phage display libraries that incorporate random or synthetic sequences, for example, in CDR regions.

Selection of Constant Region

The heavy and light chain variable regions of chimeric, humanized, or human antibodies can be linked to at least a portion of a human constant region by various well-known methods (see, e.g., Queen et al., 1989, *Proc. Natl. Acad. Sci. U.S.A.* 86:10029–10033 and WO 90/07861; these references and references cited therein are herein incorporated by reference for all purposes). The choice of constant region depends, in part, whether antibody-dependent complement and/or cellular mediated toxicity is desired. For example, isotypes $IgG_1$ and $IgG_3$ usually have greater complement binding activity than isotypes $IgG_2$ or $IgG_4$. Choice of isotype can also affect passage of antibody into the brain. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

For some applications, non IgG antibodies can be useful. For example, where multivalent antibody complexes are desired, IgM and IgA antibodies can be used.

Use of Partial Antibody Sequences to Express Intact Antibodies

Antibodies interact with target antigens predominantly through amino acid residues that are located in the six heavy and light chain complimentarity determining regions (CDR's). For this reason, the amino acid sequences within CDR's are more diverse between individual antibodies than sequences outside of CDR's. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1988, *Nature*

332:323–327; Jones, P. et al., 1986, *Nature* 321:522–525; and Queen, C. et al., 1989, *Proc. Natl. Acad. Sci. U.S.A.* 86:10029–10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequence of a high affinity secondary repertoire antibody at individual nucleotides because of somatic mutations. However, somatic mutations are not distributed evenly across the variable region. For example, somatic mutations are relatively infrequent in the amino-terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by reference for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable region. Heavy and light chain leader sequences are cleaved during protein maturation and do not contribute to the properties of the final antibody. For this reason it is not necessary to use the corresponding germline leader sequence for expression constructs. To add missing sequences, cloned cDNA sequences can be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion of particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa light chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, *J. Biol. Chem.* 266:19867–19870); and, HindIII sites are engineered upstream of the translation initiation sites.

For both the heavy and light chain variable regions, the optimized coding, and corresponding non-coding, strand sequences are broken down into 30–50 nucleotide segments such that the breaks between nucleotides for the coding strand sequence occur at approximately the midpoint of the corresponding non-coding oligonucleotide. Thus, for each chain, the oligonucleotides can be assemble into overlapping double stranded sets that completely span the desired sequence. These oligonucleotides are combined into pools that span segments of 150–400 nucleotides. The pools are then used as templates to produce PCR amplification products of 150–400 nucleotides. Typically, a single variable region oligonucleotide set will be broken down into two pools which are separately amplified to generate two overlapping PCR products. These overlapping products are then combined by PCR amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgGκ are described below. The plasmids were constructed so that PCR amplified V heavy and V kappa light chain cDNA sequences could be used to reconstruct complete heavy and light chain minigenes. These plasmids can be used to express completely human, or chimeric $IgG_1κ$ or $IgG_4κ$ antibodies. Similar plasmids can be constructed for expression of other heavy chain isotypes, or for expression of antibodies comprising lambda light chains.

The kappa light chain plasmid, pCK7-96 (SEQ ID NO:1) shown below, includes the kappa constant region and polyadenylation site, such that kappa sequences amplified with 5' primers that include HindIII sites upstream of the initiator methionine can be digested with HindIII and BbsI, and cloned into pCK7-96 digested with HindIII and BbsI to reconstruct a complete light chain coding sequence together with a polyadenylation site. This cassette can be isolated as a HindIII/NotI fragment and ligated to transcription promoter sequences to create a functional minigene for transfection into cells.

The gamma1 heavy chain plasmid, pCG7-96 (SEQ ID NO:2), includes the human gamma1 constant region and polyadenylation site, such that gamma sequences amplified with 5' primers that include HindIII sites upstream of the initiator methionine can be digested with HindIII and AgeI, and cloned into pCG7-96 digested with HindIII and AgeI to reconstruct a complete gamma1 heavy chain coding sequence together with a polyadenylation site. This cassette can be isolated as a HindIII/SalI fragment and ligated to transcription promoter sequences to create a functional minigene for transfection into cells.

The gamma4 heavy chain plasmid, pG4HE (SEQ ID NO:3), includes the human gamma4 constant region and polyadenylation site, such that gamma sequences amplified with 5' primers that include HindIII sites upstream of the initiator methionine can be digested with HindIII and AgeI, and cloned into pG4HE digested with HindIII and AgeI to reconstruct a complete gamma4 heavy chain coding sequence together with a polyadenylation site. This cassette can be isolated as a HindIII/EcoRI fragment and ligated to transcription promoter sequences to create a functional minigene for transfection into cells.

A number of different promoters (including but not limited to CMV, ubiquitin, SRalpha, and beta-actin) can be used to express the reconstructed heavy and light chain genes. For example the vector pCDNA3.1+(Invitrogen, Carlsbad, Calif.), can be cleaved with HindIII and either NotI, XhoI, or EcoRI, for ligation with either the kappa, gamma1, or gamma4 cassettes described above, to form expression vectors that can be directly transfected into mammalian cells.

pCK7-96
TCTTCCGCTTCCTCGCTCACTGACTCGCTGCGCTCGGTCGTTCGGCTGCGGCGAGCGGTATC (SEQ ID NO:1)

AGCTCACTCAAAGGCGGTAATACGGTTATCCACAGAATCAGGGGATAACGCAGGAAAGAACA

TGTGAGCAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTGGCGAAA

CCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTT

TCTCATAGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGT

CCAACCCGGTAAGACACGACTTATCGCCACTGGCAGCAGCCACTGGTAACAGGATTAGCAGA

GCGAGGTATGTAGGCGGTGCTACAGAGTTCTTGAAGTGGTGGCCTAACTACGGCTACACTAG

AAGGACAGTATTTGGTATCTGCGCTCTGCTGAAGCCAGTTACCTTCGGAAAAAGAGTTGGTA

GCTCTTGATCCGGCAAACAAACCACCGCTGGTAGCGGTGGTTTTTTTGTTTGCAAGCAGCAG

ATTACGCGCAGAAAAAAAGGATCTCAAGAAGATCCTTTGATCTTTTCTACGGGGTCTGACGC

TCAGTGGAACGAAAACTCACGTTAAGGGATTTTGGTCATGAGATTATCAAAAAGGATCTTCA

CCTAGATCCTTTTAAATTAAAAATGAAGTTTTAAATCAATCTAAAGTATATATGAGTAAACT

TGGTCTGACAGTTACCAATGCTTAATCAGTGAGGCACCTATCTCAGCGATCTGTCTATTTCG

TTCATCCATAGTTGCCTGACTCCCCGTCGTGTAGATAACTACGATACGGGAGGGCTTACCAT

CTGGCCCCAGTGCTGCAATGATACCGCGAGACCCACGCTCACCGGCTCCAGATTTATCAGCA

ATAAACCAGCCAGCCGGAAGGGCCGAGCGCAGAAGTGGTCCTGCAACTTTATCCGCCTCCAT

CCAGTCTATTAATTGTTGCCGGGAAGCTAGAGTAAGTAGTTCGCCAGTTAATAGTTTGCGCA

ACGTTGTTGCCATTGCTACAGGCATCGTGGTGTCACGCTCGTCGTTTGGTATGGCTTCATTC

AGCTCCGGTTCCCAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACT

GGTGAGTACTCAACCAAGTCATTCTGAGAATAGTGTATGCGGCGACCGAGTTGCTCTTGCCC

GGCGTCAATACGGGATAATACCGCGCCACATAGCAGAACTTTAAAAGTGCTCATCATTGGAA

AACGTTCTTCGGGGCGAAAACTCTCAAGGATCTTACCGCTGTTGAGATCCAGTTCGATGTAA

CCCACTCGTGCACCCAACTGATCTTCAGCATCTTTTACTTTCACCAGCGTTTCTGGGTGAGC

AAAAACAGGAAGGCAAAATGCCGCAAAAAAGGGAATAAGGGCGACACGGAAATGTTGAATAC

TCATACTCTTCCTTTTTCAATATTATTGAAGCATTTATCAGGGTTATTGTCTCATGAGCGGA

TACATATTTGAATGTATTTAGAAAAATAAACAAATAGGGGTTCCGCGCACATTTCCCCGAAA

AGTGCCACCTGACGTCTAAGAAACCATTATTATCATGACATTAACCTATAAAAATAGGCGTA

TCACGAGGCCCTTTCGTCTCGCGCGTTTCGGTGATGACGGTGAAAACCTCTGACACATGCAG

CTCCCGGAGACGGTCACAGCTTGTCTGTAAGCGGATGCCGGGAGCAGACAAGCCCGTCAGGG

CGCGTCAGCGGGTGTTGGCGGGTGTCGGGGCTGGCTTAACTATGCGGCATCAGAGCAGATTG

TACTCAGAGTGCACCATATGCGGTGTGAAATACCGCACAGATGCGTAAGGAGAAAATACCGC

ATCAGGCGCCATTCGCCATTCAGGCTGCGCAACTGTTGGGAAGGGCGATCGGTGCGGGCCTC

TTCGCTATTACGCCAGCTGGCGAAAGGGGGATGTGCTGCAAGGCGATTAAGTTGGGTAACGC

CAGGGTTTTCCCAGTCACGACGTTGTAAAACGACGGCCAGTGCCAAGCTAGCGGCCGCGGTC

CAACCACCAATCTCAAAGCTTGGTACCCGGGAGCCTGTTATCCCAGCACAGTCCTGGAAGAG

-continued

GCACAGGGGAAATAAAAGCGGACGGAGGCTTTCCTTGACTCAGCCGCTGCCTGGTCTTCTTC

AGACCTGTTCTGAATTCTAAACTCTGAGGGGGTCGGATGACGTGGCCATTCTTTGCCTAAAG

CATTGAGTTTACTGCAAGGTCAGAAAAGCATGCAAAGCCCTCAGAATGGCTGCAAAGAGCTC

CAACAAAACAATTTAGAACTTTATTAAGGAATAGGGGGAAGCTAGGAAGAAACTCAAAACAT

CAAGATTTTAAATACGCTTCTTGGTCTCCTTGCTATAATTATCTGGGATAAGCATGCTGTTT

TCTGTCTGTCCCTAACATGCCCTGTGATTATCCGCAAACAACACACCCAAGGGCAGAACTTT

GTTACTTAAACACCATCCTGTTTGCTTCTTTCCTCAGGAACTGTGGCTGCACCATCTGTCTT

CATCTTCCCGCCATCTGATGAGCAGTTGAAATCTGGAACTGCCTCTGTTGTGTGCCTGCTGA

ATAACTTCTATCCCAGAGAGGCCAAAGTACAGTGGAAGGTGGATAACGCCCTCCAATCGGGT

AACTCCCAGGAGAGTGTCACAGAGCAGGACAGCAAGGACAGCACCTACAGCCTCAGCAGCAC

CCTGACGCTGAGCAAAGCAGACTACGAGAAACACAAAGTCTACGCCTGCGAAGTCACCCATC

AGGGCCTGAGCTCGCCCGTCACAAAGAGCTTCAACAGGGGAGAGTGTTAGAGGGAGAAGTGC

CCCCACCTGCTCCTCAGTTCCAGCCTGACCCCCTCCCATCCTTTGGCCTCTGACCCTTTTTC

CACAGGGGACCTACCCCTATTGCGGTCCTCCAGCTCATCTTTCACCTCACCCCCCTCCTCCT

CCTTGGCTTTAATTATGCTAATGTTGGAGGAGAATGAATAAATAAAGTGAATCTTTGCACCT

GTGGTTTCTCTCTTTCCTCAATTTAATAATTATTATCTGTTGTTTACCAACTACTCAATTTC

TCTTATAAGGGACTAAATATGTAGTCATCCTAAGGCGCATAACCATTTATAAAAATCATCCT

TCATTCTATTTTACCCTATCATCCTCTGCAAGACAGTCCTCCCTCAAACCCACAAGCCTTCT

GTCCTCACAGTCCCCTGGGCCATGGATCCTCACATCCCAATCCGCGGCCGCAATTCGTAATC

ATGGTCATAGCTGTTTCCTGTGTGAAATTGTTATCCGCTCACAATTCCACACAACATACGAG

CCGGAAGCATAAAGTGTAAAGCCTGGGGTGCCTAATGAGTGAGCTAACTCACATTAATTGCG

TTGCGCTCACTGCCCGCTTTCCAGTCGGGAAACCTGTCGTGCCAGCTGCATTAATGAATCGG

CCAACGCGCGGGGAGAGGCGGTTTGCGTATTGGGCGC pCG7-96

GAACTCGAGCAGCTGAAGCTTTCTGGGGCAGGCCAGGCCTGACCTTGGCTTTGGGGCAGGGA (SEQ ID NO:2)

GGGGGCTAAGGTGAGGCAGGTGGCGCCAGCCAGGTGCACACCCAATGCCCATGAGCCCAGAC

ACTGGACGCTGAACCTCGCGGACAGTTAAGAACCCAGGGGCCTCTGCGCCCTGGGCCCAGCT

CTGTCCCACACCGCGGTCACATGGCACCACCTCTCTTGCAGCCTCCACCAAGGGCCCATCGG

TCTTCCCCCTGGCACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGCCCTGACCAGCGG

CGTGCACACCTTCCCGGCTGTCCTACAGTCCTCAGGACTCTACTCCCTCAGCAGCGTGGTGA

CCGTGCCCTCCAGCAGCTTGGGCACCCAGACCTACATCTGCAACGTGAATCACAAGCCCAGC

AACACCAAGGTGGACAAGAAAGTTGGTGAGAGGCCAGCACAGGGAGGGAGGGTGTCTGCTGG

AAGCCAGGCTCAGCGCTCCTGCCTGGACGCATCCCGGCTATGCAGCCCCAGTCCAGGGCAGC

AAGGCAGGCCCCGTCTGCCTCTTCACCCGGAGGCCTCTGCCCGCCCCACTCATGCTCAGGGA

GAGGGTCTTCTGGCTTTTTCCCCAGGCTCTGGGCAGGCACAGGCTAGGTGCCCCTAACCCAG

GCCCTGCACACAAAGGGGCAGGTGCTGGGCTCAGACCTGCCAAGAGCCATATCCGGGAGGAC

CCTGCCCCTGACCTAAGCCCACCCCAAAGGCCAAACTCTCCACTCCCTCAGCTCGGACACCT

TCTCTCCTCCCAGATTCCAGTAACTCCCAATCTTCTCTCTGCAGAGCCCAAATCTTGTGACA

AAACTCACACATGCCCACCGTGCCCAGGTAAGCCAGCCCAGGCCTCGCCCTCCAGCTCAAGG

-continued

CGGGACAGGTGCCCTAGAGTAGCCTGCATCCAGGGACAGGCCCCAGCCGGGTGCTGACACGT

CCACCTCCATCTCTTCCTCAGCACCTGAACTCCTGGGGGGACCGTCAGTCTTCCTCTTCCCC

CCAAAACCCAAGGACACCCTCATGATCTCCCGGACCCCTGAGGTCACATGCGTGGTGGTGGA

CGTGAGCCACGAAGACCCTGAGGTCAAGTTCAACTGGTACGTGGACGGCGTGGAGGTGCATA

ATGCCAAGACAAAGCCGCGGGAGGAGCAGTACAACAGCACGTACCGTGTGGTCAGCGTCCTC

ACCGTCCTGCACCAGGACTGGCTGAATGGCAAGGAGTACAAGTGCAAGGTCTCCAACAAAGC

CCTCCCAGCCCCCATCGAGAAAACCATCTCCAAAGCCAAAGGTGGGACCCGTGGGGTGCGAG

GGCCACATGGACAGAGGCCGGCTCGGCCCACCCTCTGCCCTGAGAGTGACCGCTGTACCAAC

CTCTGTCCCTACAGGGCAGCCCCGAGAACCACAGGTGTACACCCTGCCCCCATCCCGGGATG

AGCTGACCAAGAACCAGGTCAGCCTGACCTGCCTGGTCAAAGGCTTCTATCCCAGCGACATC

GCCGTGGAGTGGGAGAGCAATGGGCAGCCGGAGAACAACTACAAGACCACGCCTCCCGTGCT

GGACTCCGACGGCTCCTTCTTCCTCTACAGCAAGCTCACCGTGGACAAGAGCAGGTGGCAGC

AGGGGAACGTCTTCTCATGCTCCGTGATGCATGAGGCTCTGCACAACCACTACACGCAGAAG

AGCCTCTCCCTGTCTCCGGGTAAATGAGTGCGACGGCCGGCAAGCCCCCGCTCCCCGGGCTC

TCGCGGTCGCACGAGGATGCTTGGCACGTACCCCCTGTACATACTTCCCGGGCGCCCAGCAT

GGAAATAAAGCACCCAGCGCTGCCCTGGGCCCCTGCGAGACTGTGATGGTTCTTTCCACGGG

TCAGGCCGAGTCTGAGGCCTGAGTGGCATGAGGGAGGCAGAGCGGGTCCCACTGTCCCCACA

CTGGCCCAGGCTGTGCAGGTGTGCCTGGGCCCCCTAGGGTGGGGCTCAGCCAGGGGCTGCCC

TCGGCAGGGTGGGGGATTTGCCAGCGTGGCCCTCCCTCCAGCAGCACCTGCCCTGGGCTGGG

CCACGGGAAGCCCTAGGAGCCCCTGGGGACAGACACACAGCCCCTGCCTCTGTAGGAGACTG

TCCTGTTCTGTGAGCGCCCCTGTCCTCCCGACCTCCATGCCCACTCGGGGGCATGCCTGCAG

GTCGACTCTAGAGGATCCCCGGGTACCGAGCTCGAATTCATCGATGATATCAGATCTGCCGG

TCTCCCTATAGTGAGTCGTATTAATTTCGATAAGCCAGGTTAACCTGCATTAATGAATCGGC

CAACGCGCGGGGAGAGGCGGTTTGCGTATTGGGCGCTCTTCCGCTTCCTCGCTCACTGACTC

GCTGCGCTCGGTCGTTCGGCTGCGGCGAGCGGTATCAGCTCACTCAAAGGCGGTAATACGGT

TATCCACAGAATCAGGGGATAACGCAGGAAAGAACATGTGAGCAAAAGGCCAGCAAAAGGCC

AGGAACCGTAAAAAGGCCGCGTTGCTGGCGTTTTTCCATAGGCTCCGCCCCCCTGACGAGCA

TCACAAAAATCGACGCTCAAGTCAGAGGTGGCGAAACCCGACAGGACTATAAAGATACCAGG

CGTTTCCCCCTGGAAGCTCCCTCGTGCGCTCTCCTGTTCCGACCCTGCCGCTTACCGGATAC

CTGTCCGCCTTTCTCCCTTCGGGAAGCGTGGCGCTTTCTCAATGCTCACGCTGTAGGTATCT

CAGTTCGGTGTAGGTCGTTCGCTCCAAGCTGGGCTGTGTGCACGAACCCCCCGTTCAGCCCG

ACCGCTGCGCCTTATCCGGTAACTATCGTCTTGAGTCCAACCCGGTAAGACACGACTTATCG

CCACTGGCAGCAGCCACTGGTAACAGGATTAGCAGAGCGAGGTATGTAGGCGGTGCTACAGA

GTTCTTGAAGTGGTGGCCTAACTACGGCTACACTAGAAGGACAGTATTTGGTATCTGCGCTC

TGCTGAAGCCAGTTACCTTCGGAAAAAGAGTTGGTAGCTCTTGATCCGGCAAACAAACCACC

GCTGGTAGCGGTGGTTTTTTTGTTTGCAAGCAGCAGATTACGCGCAGAAAAAAAGGATCTCA

AGAAGATCCTTTGATCTTTTCTACGGGGTCTGACGCTCAGTGGAACGAAAACTCACGTTAAG

GGATTTTGGTCATGAGATTATCAAAAAGGATCTTCACCTAGATCCTTTTAAATTAAAAATGA

AGTTTTAAATCAATCTAAAGTATATATGAGTAAACTTGGTCTGACAGTTACCAATGCTTAAT

CAGTGAGGCACCTATCTCAGCGATCTGTCTATTTCGTTCATCCATAGTTGCCTGACTCCCCG

-continued

TCGTGTAGATAACTACGATACGGGAGGGCTTACCATCTGGCCCCAGTGCTGCAATGATACCG

CGACACCCACGCTCACCGGCTCCAGATTTATCAGCAATAAACCAGCCAGCCGGAAGGGCCGA

GCGCAGAAGTGGTCCTGCAACTTTATCCGCCTCCATCCAGTCTATTAATTGTTGCCGGGAAG

CTAGAGTAAGTAGTTCGCCAGTTAATAGTTTGCGCAACGTTGTTGCCATTGCTACAGGCATC

GTGGTGTCACGCTCGTCGTTTGGTATGGCTTCATTCAGCTCCGGTTCCCAACGATCAAGGCG

AGTTACATGATCCCCCATGTTGTGCAAAAAAGCGGTTAGCTCCTTCGGTCCTCCGATCGTTG

TCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTG

AGAATAGTGTATGCGGCGACCGAGTTGCTCTTGCCCGGCGTCAATACGGGATAATACCGCGC

CACATAGCAGAACTTTAAAAGTGCTCATCATTGGAAAACGTTCTTCGGGGCGAAAACTCTCA

AGGATCTTACCGCTGTTGAGATCCAGTTCGATGTAACCCACTCGTGCACCCAACTGATCTTC

AGCATCTTTTACTTTCACCAGCGTTTCTGGGTGAGCAAAAACAGGAAGGCAAAATGCCGCAA

AAAAGGGAATAAGGGCGACACGGAAATGTTGAATACTCATACTCTTCCTTTTTCAATATTAT

TGAAGCATTTATCAGGGTTATTGTCTCATGAGCGGATACATATTTGAATGTATTTAGAAAAA

TAAACAAATAGGGGTTCCGCGCACATTTCCCCGAAAAGTGCCACCTGACGTCTAAGAAACCA

TTATTATCATGACATTAACCTATAAAAATAGGCGTATCACGAGGCCCTTTCGTCTCGCGCGT

TTCGGTGATGACGGTGAAAACCTCTGACACATGCAGCTCCCGGAGACGGTCACAGCTTGTCT

GTAAGCGGATGCCGGGAGCAGACAAGCCCGTCAGGGCGCGTCAGCGGGTGTTGGCGGGTGTC

GGGGCTGGCTTAACTATGCGGCATCAGAGCAGATTGTACTGAGAGTGCACCATATGGACATA

TTGTCGTTAGAACGCGGCTACAATTAATACATAACCTTATGTATCATACACATACGATTTAG

GTGACACTATA pG4HE

GAACTCGAGCAGCTGAAGCTTTCTGGGGCAGGCCGGGCCTGACTTTGGCTGGGGGCAGGGAG (SEQ ID NO:3)

GGGGCTAAGGTGACGCAGGTGGCGCCAGCCAGGTGCACACCCAATGCCCATGAGCCCAGACA

CTGGACCCTGCATGGACCATCGCGGATAGACAAGAACCGAGGGGCCTCTGCGCCCTGGGCCC

AGCTCTGTCCCACACCGCGGTCACATGGCACCACCTCTCTTGCAGCTTCCACCAAGGGCCCA

TCCGTCTTCCCCCTGGCGCCCTGCTCCAGGAGCACCTCCGAGAGCACAGCCGCCCTGGGCTG

CCTGGTCAAGGACTACTTCCCCGAACCGGTGACGGTGTCGTGGAACTCAGGCGCCCTGACCA

GCGGCGTGCACACCTTCCCGGCTGTCCTACAGTCCTCAGGACTCTACTCCCTCAGCAGCGTG

GTGACCGTGCCCTCCAGCAGCTTGGGCACGAAGACCTACACCTGCAACGTAGATCACAAGCC

CAGCAACACCAAGGTGGACAAGAGAGTTGGTGAGAGGCCAGCACAGGGAGGGAGGGTGTCTG

CTGGAAGCCAGGCTCAGCCCTCCTGCCTGGACGCACCCCGGCTGTGCAGCCCCAGCCCAGGG

CAGCAAGGCATGCCCCATCTGTCTCCTCACCCGGAGGCCTCTGACCACCCCACTCATGCTCA

GGGAGAGGGTCTTCTGGATTTTTCCACCAGGCTCCGGGCAGCCACAGGCTGGATGCCCCTAC

CCCAGGCCCTGCGCATACAGGGGCAGGTGCTGCGCTCAGACCTGCCAAGAGCCATATCCGGG

AGGACCCTGCCCCTGACCTAAGCCCACCCCAAAGGCCAAACTCTCCACTCCCTCAGCTCAGA

CACCTTCTCTCCTCCCAGATCTGAGTAACTCCCAATCTTCTCTCTGCAGAGTCCAAATATGG

TCCCCCATGCCCATCATGCCCAGGTAAGCCAACCCAGGCCTCGCCCTCCAGCTCAAGGCGGG

ACAGGTGCCCTAGAGTAGCCTGCATCCAGGGACAGGCCCCAGCCGGGTGCTGACGCATCCAC

CTCCATCTCTTCCTCAGCACCTGAGTTCCTGGGGGGACCATCAGTCTTCCTGTTCCCCCCAA

AACCCAAGGACACTCTCATGATCTCCCGGACCCCTGAGGTCACGTGCGTGGTGGTGGACGTG

-continued

AGCCAGGAAGACCCCGAGGTCCAGTTCAACTGGTACGTGGATGGCGTGGAGGTGCATAATGC

CAAGACAAAGCCGCGGGAGGAGCAGTTCAACAGCACGTACCGTGTGGTCAGCGTCCTCACCG

TCCTGCACCAGGACTGGCTGAACGGCAAGGAGTACAAGTGCAAGGTCTCCAACAAAGGCCTC

CCGTCCTCCATCGAGAAAACCATCTCCAAAGCCAAAGGTGGGACCCACGGGGTGCGAGGGCC

ACATGGACAGAGGTCAGCTCGGCCCACCCTCTGCCCTGGGAGTGACCGCTGTGCCAACCTCT

GTCCCTACAGGGCAGCCCCGAGAGCCACAGGTGTACACCCTGCCCCCATCCCAGGAGGAGAT

GACCAAGAACCAGGTCAGCCTGACCTGCCTGGTCAAAGGCTTCTACCCCAGCGACATCGCCG

TGGAGTGGGAGAGCAATGGGCAGCCGGAGAACAACTACAAGACCACGCCTCCCGTGCTGGAC

TCCGACGGCTCCTTCTTCCTCTACAGCAGGCTAACCGTGGACAAGAGCAGGTGGCAGGAGGG

GAATGTCTTCTCATGCTCCGTGATGCATGAGGCTCTGCACAACCACTACACACAGAAGAGCC

TCTCCCTGTCTCTGGGTAAATGAGTGCCAGGGCCGGCAAGCCCCCGCTCCCCGGGCTCTCGG

GGTCGCGCGAGGATGCTTGGCACGTACCCCGTCTACATACTTCCCAGGCACCCAGCATGGAA

ATAAAGCACCCACCACTGCCCTGGGCCCCTGTGAGACTGTGATGGTTCTTTCCACGGGTCAG

GCCGAGTCTGAGGCCTGAGTGACATGAGGGAGGCAGAGCGGGTCCCACTGTCCCCACACTGG

CCCAGGCTGTGCAGGTGTGCCTGGGCCACCTAGGGTGGGGCTCAGCCAGGGGCTGCCCTCGG

CAGGGTGGGGGATTTGCCAGCGTGGCCCTCCCTCCAGCAGCAGCTGCCCTGGGCTGGGCCAC

GGGAAGCCCTAGGAGCCCCTGGGGACAGACACACAGCCCCTGCCTCTGTAGGAGACTGTCCT

GTCCTGTGAGCGCCCTGTCCTCCGACCCCCCATGCCCACTCGGGGGGATCCCCGGGTACCGA

GCTCGAATTCATCGATGATATCAGATCTGCCGGTCTCCCTATAGTGAGTCGTATTAATTTCG

ATAAGCCAGGTTAACCTGCATTAATGAATCGGCCAACGCGCGGGGAGAGGCGGTTTGCGTAT

TGGGCGCTCTTCCGCTTCCTCGCTCACTGACTCGCTGCGCTCGGTCGTTCGGCTGCGGCGAG

CGGTATCAGCTCACTCAAAGGCGGTAATACGGTTATCCACAGAATCAGGGGATAACGCAGGA

AAGAACATGTGAGCAAAAGGCCAGCAAAAGGCCAGGAACCGTAAAAAGGCCGCGTTGCTGGC

GTTTTTCCATAGGCTCCGCCCCCCTGACGAGCATCACAAAAATCGACGCTCAAGTCAGAGGT

GGCGAAACCCGACAGGACTATAAAGATACCAGGCGTTTCCCCCTGGAAGCTCCCTCGTGCGC

TCTCCTGTTCCGACCCTGCCGCTTACCGGATACCTGTCCGCCTTTCTCCCTTCGGGAAGCGT

GGCGCTTTCTCAATGCTCACGCTGTAGGTATCTCAGTTCGGTGTAGGTCGTTCGCTCCAAGC

TGGGCTGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAACAGGAT

TAGCAGAGCGAGGTATGTAGGCGGTGCTACAGAGTTCTTGAAGTGGTGGCCTAACTACGGCT

ACACTAGAAGGACAGTATTTGGTATCTGCGCTCTGCTGAAGCCAGTTACCTTCGGAAAAAGA

GTTGGTAGCTCTTGATCCGGCAAACAAACCACCGCTGGTAGCGGTGGTTTTTTTGTTTGCAA

GCAGCAGATTACGCGCAGAAAAAAAGGATCTCAAGAAGATCCTTTGATCTTTTCTACGGGGT

CTGACGCTCAGTGGAACGAAAACTCACGTTAAGGGATTTTGGTCATGAGATTATCAAAAAGG

ATCTTCACCTAGATCCTTTTAAATTAAAAATGAAGTTTTAAATCAATCTAAAGTATATATGA

GTAAACTTGGTCTGACAGTTACCAATGCTTAATCAGTGAGGCACCTATCTCAGCGATCTGTC

TATTTCGTTCATCCATAGTTGCCTGACTCCCCGTCGTGTAGATAACTACGATACGGGAGGGC

TTACCATCTGGCCCCAGTGCTGCAATGATACCGCGAGACCCACGCTCACCGGCTCCAGATTT

ATCAGCAATAAACCAGCCAGCCGGAAGGGCCGAGCGCAGAAGTGGTCCTGCAACTTTATCCG

CCTCCATCCAGTCTATTAATTGTTGCCGGGAAGCTAGAGTAAGTAGTTCGCCAGTTAATAGT

-continued

```
TTGCGCAACGTTGTTGCCATTGCTACAGGCATCGTGGTGTCACGCTCGTCGTTTGGTATGGC

TTCATTCAGCTCCGGTTCCCAACGATCAAGGCGAGTTACATGATCCCCCATGTTGTGCAAAA

AAGCGGTTAGCTCCTTCGGTCCTCCGATCGTTGTCAGAAGTAAGTTGGCCGCAGTGTTATCA

CTCATGGTTATGGCAGCACTGCATAATTCTCTTACTGTCATGCCATCCGTAAGATGCTTTTC

TGTGACTGGTGAGTACTCAACCAAGTCATTCTGAGAATAGTGTATGCGGCGACCGAGTTGCT

CTTGCCCGGCGTCAATACGGGATAATACCGCGCCACATAGCAGAACTTTAAAAGTGCTCATC

ATTGGAAAACGTTCTTCGGGGCGAAAACTCTCAAGGATCTTACCGCTGTTGAGATCCAGTTC

GATGTAACCCACTCGTGCACCCAACTGATCTTCAGCATCTTTTACTTTCACCAGCGTTTCTG

GGTGAGCAAAAACAGGAAGGCAAAATGCCGCAAAAAAGGGAATAAGGGCGACACGGAAATGT

TGAATACTCATACTCTTCCTTTTTCAATATTATTGAAGCATTTATCAGGGTTATTGTCTCAT

GAGCGGATACATATTTGAATGTATTTAGAAAAATAAACAAATAGGGGTTCCGCGCACATTTC

CCCGAAAAGTGCCACCTGACGTCTAAGAAACCATTATTATCATGACATTAACCTATAAAAAT

AGGCGTATCACGAGGCCCTTTCGTCTCGCGCGTTTCGGTGATGACGGTGAAAACCTCTGACA

CATGCAGCTCCCGGAGACGGTCACAGCTTGTCTGTAAGCGGATGCCGGGAGCAGACAAGCCC

GTCAGGGCGCGTCAGCGGGTGTTGGCGGGTGTCGGGGCTGGCTTAACTATGCGGCATCAGAG

CAGATTGTACTGAGAGTGCACCATATGGACATATTGTCGTTAGAACGCCGCTACAATTAATA

CATAACCTTATGTATCATACACATACGATTTAGGTGACACTATA
```

Expression of Recombinant Antibodies

Chimeric, humanized and human antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

These expression vectors are typically replicable in the host organisms either as episomes or as an integral part of the host chromosomal DNA. Commonly, expression vectors contain selection markers, e.g., ampicillin-resistance or hygromycin-resistance, to permit detection of those cells transformed with the desired DNA sequences.

*E. coli* is one prokaryotic host particularly useful for cloning the DNA sequences of the present invention. Microbes, such as yeast are also useful for expression. Saccharomyces is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilization.

Mammalian cells are a preferred host for expressing nucleotide segments encoding immunoglobulins or fragments thereof. See Winnacker, FROM GENES TO CLONES, (VCH Publishers, NY, 1987). A number of suitable host cell lines capable of secreting intact heterologous proteins have been developed in the art, and include CHO cell lines, various COS cell lines, HeLa cells, L cells and myeloma cell lines. Preferably, the cells are nonhuman. Expression vectors for these cells can include expression control sequences, such as an origin of replication, a promoter, an enhancer (Queen et al., 1986, *Immunol. Rev.* 89:49), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., 1992, *J. Immunol.* 148:1149.

Alternatively, antibody coding sequences can be incorporated in transgenes for introduction into the genome of a transgenic animal and subsequent expression in the milk of the transgenic animal (see, e.g., U.S. Pat. Nos. 5,741,957, 5,304,489, and 5,849,992). Suitable transgenes include coding sequences for light and/or heavy chains in operable linkage with a promoter and enhancer from a mammary gland specific gene, such as casein or beta lactoglobulin.

The vectors containing the DNA segments of interest can be transferred into the host cell by well-known methods, depending on the type of cellular host. For example, calcium chloride transfection is commonly utilized for prokaryotic cells, whereas calcium phosphate treatment, electroporation, lipofection, biolistics or viral-based transfection can be used for other cellular hosts. Other methods used to transform mammalian cells include the use of polybrene, protoplast fusion, liposomes, electroporation, and microinjection (see generally, Sambrook et al., supra). For production of transgenic animals, transgenes can be microinjected into fertilized oocytes, or can be incorporated into the genome of embryonic stem cells, and the nuclei of such cells transferred into enucleated oocytes.

Once expressed, antibodies can be purified according to standard procedures of the art, including HPLC purification, column chromatography, gel electrophoresis and the like (see generally, Scopes, *Protein Purification* (Springer-Verlag, NY, 1982)).

Modified Antibodies

Also included in the invention are modified antibodies. The term "modified antibody" includes antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody.

The antibody conjugates of the invention can be used to modify a given biological response or create a biological response (e.g., to recruit effector cells). The drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-alpha; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy:A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982).

Treatment Regimes

The invention provides pharmaceutical compositions comprising one or a combination of monoclonal antibodies (intact or binding fragments thereof) formulated together with a pharmaceutically acceptable carrier. Some compositions include a combination of multiple (e.g., two or more) monoclonal antibodies or antigen-binding portions thereof of the invention. In some compositions, each of the antibodies or antigen-binding portions thereof of the composition is a monoclonal antibody or a human sequence antibody that binds to a distinct, pre-selected epitope of an antigen.

In prophylactic applications, pharmaceutical compositions or medicaments are administered to a patient susceptible to, or otherwise at risk of a disease or condition (i.e., an immune disease) in an amount sufficient to eliminate or reduce the risk, lessen the severity, or delay the outset of the disease, including biochemical, histologic and/or behavioral symptoms of the disease, its complications and intermediate pathological phenotypes presenting during development of the disease. In therapeutic applications, compositions or medicants are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective Dosages

Effective doses of the compositions of the present invention, for the treatment of immune-related conditions and diseases described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy.

For administration with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1–10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody in the patient. In some methods, dosage is adjusted to achieve a plasma antibody concentration of 1–1000 μg/ml and in some methods 25–300 μg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 μg to 10 mg, or 30–300 μg DNA per patient. Doses for infectious viral vectors vary from 10–100, or more, virions per dose.

Route of Administration

Agents for inducing an immune response can be administered by parenteral, topical, intravenous, oral, subcutaneous, intraarterial, intracranial, intraperitoneal, intranasal or intramuscular means for prophylactic and/or therapeutic treatment. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. Intramuscular injection on intravenous infusion are preferred for administration of antibody. In some methods, particular therapeutic antibodies are injected directly into the cranium. In some methods, antibodies are administered as a sustained release composition or device, such as a Medipad™ device.

Agents of the invention can optionally be administered in combination with other agents that are at least partly effective in treating various diseases including various immune-related diseases. In the case of Alzheimer's and Down's syndrome, in which amyloid deposits occur in the brain, agents of the invention can also be administered in conjunction with other agents that increase passage of the agents of the invention across the blood-brain barrier (BBB).

Formulation

Agents of the invention are often administered as pharmaceutical compositions comprising an active therapeutic agent, i.e., and a variety of other pharmaceutically acceptable components. See *Remington's Pharmaceutical Science* (15th ed., Mack Publishing Company, Easton, Pa., 1980). The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules such as proteins, polysaccharides such as chitosan, polylactic acids, polyglycolic acids and copolymers (such as latex functionalized sepharose™, agarose, cellulose, and the like), polymeric amino acids, amino acid copolymers, and lipid aggregates (such as oil droplets or liposomes). Additionally, these carriers can function as immunostimulating agents (i.e., adjuvants).

For parenteral administration, agents of the invention can be administered as injectable dosages of a solution or suspension of the substance in a physiologically acceptable diluent with a pharmaceutical carrier that can be a sterile liquid such as water oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above (see Langer, 1990, *Science* 249:1527 and Hanes, 1997, *Advanced Drug Delivery Reviews* 28:97–119). The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%–2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%–95% of active ingredient, preferably 25%–70%.

Topical application can result in transdermal or intradermal delivery. Topical administration can be facilitated by co-administration of the agent with cholera toxin or detoxified derivatives or subunits thereof or other similar bacterial toxins (See Glenn et al., 1998, *Nature* 391:851). Co-administration can be achieved by using the components as a mixture or as linked molecules obtained by chemical crosslinking or expression as a fusion protein.

Alternatively, transdertnal delivery can be achieved using a skin patch or using transferosomes (Paul et al., 1995, *Eur. J. Immunol.* 25, 3521–24; Cevc et al., 1998, *Biochem. Biophys. Acta* 1368, 201–15).

The pharmaceutical compositions are generally formulated as sterile, substantially isotonic and in full compliance with all Good Manufacturing Practice (GMP) regulations of the U.S. Food and Drug Administration.

Toxicity

Preferably, a therapeutically effective dose of the proteins described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1, p.1).

Kits

Also within the scope of the invention are kits comprising the compositions (e.g., monoclonal antibodies, human sequence antibodies, human antibodies, multispecific and bispecific molecules) of the invention and instructions for use. The kit can further contain a least one additional reagent, or one or more additional human antibodies of the invention (e.g., a human antibody having a complementary activity which binds to an epitope in the antigen distinct from the first human antibody). Kits typically include a label indicating the intended use of the contents of the kit. The term label includes any writing, or recorded material supplied on or with the kit, or which otherwise accompanies the kit.

EXAMPLES

Example 1

Generation of Cmu Targeted Mice

Construction of a CMD targeting vector. The plasmid pICEmu contains an EcoRI/XhoI fragment of the murine Ig heavy chain locus, spanning the mu gene, that was obtained from a Balb/C genomic lambda phage library (Marcu et al., 1980, *Cell* 22:187). This genomic fragment was subeloned into the XhoI/EcoRI sites of the plasmid pICEMI9H (Marsh et al., 1984, *Gene* 32: 481–485). The heavy chain sequences included in pICEmu extend downstream of the EcoRI site located just 3' of the mu intronic enhancer, to the XhoI site located approximately 1 kb downstream of the last transmembrane exon of the mu gene; however, much of the mu switch repeat region has been deleted by passage in *E. coli.*

The targeting vector was constructed as follows (see FIG. 1). A 1.3 kb HindIII/SmaI fragment was excised from pICEmu and subcloned into HindIII/SmaI digested pBluescript (Stratagene, La Jolla, Calif.). This pICEmu fragment extends from the HindIII site located approximately 1 kb 5' of Cmu1 to the SmaI site located within Cmu1. The resulting plasmid was digested with SmaI/SpeI and the approximately 4 kb SmaI/XbaI fragment from pICEmu, extending from the Sma I site in Cmu1 3' to the XbaI site located just downstream of the last Cmu exon, was inserted. The resulting plasmid, pTAR1, was linearized at the SmaI site, and a neo expression cassette inserted. This cassette consists of the neo gene under the transcriptional control of the mouse phosphoglycerate kinase (pgk) promoter (XbaI/TaqI fragment; Adra et al., 1987, *Gene* 60:65–74) and containing the pgk polyadenylation site (PvuII/HindIII fragment; Boer et al., 1990, *Biochemical Genetics* 28:299–308). This cassette was obtained from the plasmid pKJ1 (described by Tybulewicz et al., 1991, *Cell* 65:1153–1163) from which the neo cassette was excised as an EcoRI/HindIII fragment and subcloned into EcoRI/HindIII digested pGEM-7Zf (+) to generate pGEM-7 (KJ1). The neo cassette was excised from pGEM-7 (KJ1) by EcoRI/SalI digestion, blunt ended and subcloned into the SmaI site of the plasmid pTAR1, in the opposite orientation of the genomic Cmu sequences. The resulting plasmid was linearized with Not I, and a herpes simplex virus thymidine kinase (tk) cassette was inserted to allow for enrichment of ES clones bearing homologous recombinants, as described by Mansour et al., 1988, *Nature* 336:348–352. This cassette consists of the coding sequences of the tk gene bracketed by the mouse pgk promoter and polyadenylation site, as described by Tybulewicz et al., 1991, *Cell* 65:1153–1163. The resulting CMD targeting vector contains a total of approximately 5.3 kb of homology to the heavy chain locus and is designed to generate a mutant mu gene into which has been inserted a neo expression cassette in the unique SmaI site of the first Cmu exon. The targeting vector was linearized with PvuI, which cuts within plasmid sequences, prior to electroporation into ES cells.

Generation and analysis of targeted ES cells. AB-1 ES cells (McMahon, A. P. and Bradley, A., 1990, *Cell* 62:1073–1085) were grown on mitotically inactive SNL76/7 cell feeder layers (ibid.) essentially as described (Robertson, E. J. (1987) in Teratocarcinomas and Embryonic Stem Cells: A Practical Approach (E. J. Robertson, ed.) Oxford, IRL Press, p. 71– 112). The linearized CMD targeting vector was electroporated into AB-1 cells by the methods described Hasty et al. (Hasty, P. R. et al., 1991, *Nature* 350:243–246). Electroporated cells were plated into 100 mm dishes at a density of 1–2×$10^6$ cells/dish. After 24 hours, G418 (200 micrograms/ml of active component) and FIAU (5×$10^{-7}$ M) were added to the medium, and drug-resistant clones were allowed to develop over 8–9 days. Clones were picked, trypsinized, divided into two portions, and further expanded. Half of the cells derived from each clone were then frozen and the other half analyzed for homologous recombination between vector and target sequences.

DNA analysis was carried out by Southern blot hybridization. DNA was isolated from the clones as described Laird et al. (Laird, P. W. et al., 1991, *Nucleic Acids Res.* 19 :4293). Isolated genomic DNA was digested with SpeI and probed with a 915 bp SacI fragment, probe A (FIG. 1), which hybridizes to a sequence between the mu intronic enhancer and the mu switch region. Probe A detects a 9.9 kb SpeI fragment from the wild type locus, and a diagnostic 7.6 kb band from a mu locus which has homologously recombined with the CMD targeting vector (the neo expression cassette contains a SpeI site). Of 1132 G418 and FIAU resistant clones screened by Southern blot analysis, 3 displayed the 7.6 kb Spe I band indicative of homologous recombination at the mu locus. These 3 clones were further digested with the enzymes BglI, BstXI, and EcoRI to verify that the vector integrated homologously into the mu gene. When hybridized with probe A, Southern blots of wild type DNA digested with BglI, BstXI, or EcoRI produce fragments of 15.7, 7.3, and 12.5 kb, respectively, whereas the presence of a targeted mu allele is indicated by fragments of 7.7, 6.6, and 14.3 kb, respectively. All 3 positive clones detected by the SpeI digest showed the expected BglI, BstXI, and EcoRI restriction fragments diagnostic of insertion of the neo cassette into the Cmul exon.

Generation of mice bearing the mutated mu gene. The three targeted ES clones, designated number 264, 272, and 408, were thawed and injected into C57BL/6J blastocysts as described by Bradley (Bradley, A., 1987, in Teratocarcinomas and Embryonic Stem Cells:a Practical Approach. (E. J. Robertson, ed.) Oxford:IRL Press, p. 113–151). Injected blastocysts were transferred into the uteri of pseudopregnant females to generate chimeric mice representing a mixture of cells derived from the input ES cells and the host blastocyst.

The extent of ES cell contribution to the chimera can be visually estimated by the amount of agouti coat coloration, derived from the ES cell line, on the black C57BL/6J background. Clones 272 and 408 produced only low percentage chimeras (i e., low percentage of agouti pigmentation) but clone 264 produced high percentage male chimeras. These chimeras were bred with C57BL/6J females and agouti offspring were generated, indicative of germline transmission of the ES cell genome. Screening for the targeted mu gene was carried out by Southern blot analysis of BglI digested DNA from tail biopsies (as described above for analysis of ES cell DNA). Approximately 50% of the agouti offspring showed a hybridizing BglI band of 7.7 kb in addition to the wild type band of 15.7 kb, demonstrating a germline transmission of the targeted mu gene.

Analysis of transgenic mice for functional inactivation of mu gene. To determine whether the insertion of the neo cassette into Cmu1 has inactivated the Ig heavy chain gene, a clone 264 chimera was bred with a mouse homozygous for the JHD mutation, which inactivates heavy chain expression as a result of deletion of the JH gene segments (Chen et al., 1993, *Immunol.* 5:647–656). Four agouti offspring were generated. Serum was obtained from these animals at the age of 1 month and assayed by ELISA for the presence of murine IgM. Two of the four offspring were completely lacking IgM (Table 1). Genotyping of the four animals by Southern blot analysis of DNA from tail biopsies by BglI digestion and hybridization with probe A (FIG. 1), and by StuI digestion and hybridization with a 475 bp EcoRI/StuI fragment (ibid.) demonstrated that the animals which fail to express serum IgM are those in which one allele of the heavy chain locus carries the JHD mutation, the other allele the Cmul mutation. Mice heterozygous for the JHD mutation display wild type levels of serum Ig. These data demonstrate that the Cmu1 mutation inactivates expression of the mu gene.

TABLE 1

| Mouse | Serum IgM (microgram s/ml) | Ig H chain genotype |
|---|---|---|
| 42 | <0.002 | CMD/JHD |
| 43 | 196 | +/JHD |
| 44 | <0.002 | CMD/JHD |
| 45 | 174 | +/JHD |
| 129 × BL6 F1 | 153 | +/+ |
| JHD | <0.002 | JHD/JHD |

Table 1 shows the levels of serum IgM, detected by ELISA, for mice carrying both the CMD and JHD mutations (CMD/JHD), for mice heterozygous for the JHD mutation (+/JHD), for wild type (129Sv×C57BL/6J)F1 mice (+/+), and for B cell deficient mice homozygous for the JHD mutation (JHD/JHD).

Example 2

The Human Kappa Light Chain Transgene KCoS

The generation of the human kappa light chain transgenic mouse line KCo5-9272 has been previously described KCo5 (Fishwild, D. et al., 1996, *Nat. Biotechnol.* 14, 845–851; Example 38 in U.S. Pat. No. 5,770,429). This line was generated by co-injection of an artificial human κ light chain locus and a YAC clone comprising multiple human V kappa. segments. The YAC clone DNA was isolated from a yeast strain containing a 450 kb yeast artificial chromosome (YAC) comprising a portion of the human V kappa locus (ICRF YAC library designation 4×17E1). DNA sequence analysis of V gene segments amplified from the YAC DNA demonstrated that this clone comprised a substantial portion of the human distal V kappa region, including approximately 32 different V kappa segments. Analysis of a different isolate of this clone (Brensing-Kuppers, J., et al., 1997, *Gene* 191:173–181) confirmed that result, and also demonstrated that this clone represents an example of the human kappa locus C haplotype, in which the 5' portion of the distal V cluster resembles the homologous region of the proximal V cluster. Thus, the 5' O family V gene segments, are close in sequence to the homologous proximal Op family V segments.

To obtain purified YAC DNA for microinjection into embryo pronuclei, total genomic DNA was size fractionated on agarose gels. The yeast cells containing YAC 4×17E1 were imbedded in agarose prior to lysis, and YAC DNA was separated from yeast chromosomal DNA by pulse field gel electrophoresis, isolated and microinjected into half day embryo pronuclei.

A Southern blot analysis of genomic DNA demonstrated that the human VkA10 gene (Cox, J. et al., 1994, *Eur. J. Immunol.* 24:827–836; Schable, K. & Zachau, H., 1993, *Biol. Chem. Hoppe-Seyler* 374:1001–1022) is incorporated into the genome of KCo5-9272 mice. PCR analysis using probes (Brensing-Kuppers, J., et al., 1997, *Gene* 191:173–181) specific for the region 5' of V kappa O1 (m217-1, Genbank X76071; AB129, ccaccccataaacactgattc (SEQ ID NO:4); AB 130, ttgatgcatcctacccagggc (SEQ ID NO:5)) and the intergenic region between V kappa L24 and L25 (m138-13, Genbank X72824; AB127, cctgccttacagtgctgtag (SEQ ID NO:6); AB128, ggacagcaacaggacatggg (SEQ ID NO:7)), revealed that the 5' and 3' regions of the V kappa cluster from the YAC clone 4×17E1 are included in the KCo5-9272 transgene integration. Line KCo5-9272 mice were then bred with human heavy chain transgenic, endogenous immunoglobulin locus mutant, mice to obtain mice homozygous for disruptions of the endogenous heavy and kappa light chain loci, and hemi- or homozygous for the human heavy chain transgenes HC2 or HCo7 (U.S. Pat. No. 5,770,429), and the human kappa light chain transgene KCo5. Animals that are homozygous for disruptions of the endogenous heavy and kappa light chain loci, and hemi- or homozygous for human heavy and κ light chain transgenes are designated double transgenic/double deletion mice.

DNA sequence analysis of CDNA clones derived directly from the KCo5 double transgenic/double deletion mice, or from hybridomas generated from these animals, revealed expression of the following V kappa genes: L6, A27, O12, O4/014, A10, L15, L18, L19, and L24.

Example 3

Cross Breeding

The human heavy chain locus containing chromosome 14 fragment hCF(SC20) and the human kappa light chain transgene were combined into a single strain by cross breeding. The hCF(SC20) transgenic mouse strain was homozygous for inactivation mutations of the endogenous heavy chain locus (CM2D) and the endogenous kappa light chain (CKD). This strain was also homozygous for λl (low) mutation (Tomizuka, K. et al., 2000, *Proc. Natl. Acad. Sci. U.S.A.* 97:722–727). The CM2D mutation comprises a deletion of a 3.7 kb BamHI-XhoI segment covering part of Cmu2, Cmu3-Cmu4, and Mmu1 and Mmu2. The CKD mutation comprises a deletion of a 2 kb SacII-BglII segment covering the Ckappa exon. Both mutations have been previously reported (Tomizuka, K. et al., 2000, *Proc. Natl. Acad. Sci. U.S.A.* 97:722–727). These mice were bred with mice homozygous for the KCo5-9272 human kappa transgene insertion, and homozygous for the CMD and JKD disruptions of the endogenous heavy chain and kappa chain loci respectively. The CMD mutation is described in Example 1 above. The JKD mutation is described in U.S. Pat. No. 5,770,429, and in Chen et al., 1993, *EMBO J.* 12:821–830). Offspring from these matings that are positive for the hCF(SC20) transchromosome (SC20/KCo5 mice, or cross-bred mice) are hemizygous for 6 different genetic modifications: SC20, KCo5, CMD, CHD, JKD, and CKD2.However, because both the CMD and CM2D mutations of the endogenous heavy chain locus prevent expression of the mouse mu gene, and both the JKD and CKD mutations of the endogenous kappa locus prevent expression of mouse kappa, these SC20/KCo5 mice are homozygous for disruptions of each of these two loci. Therefore, the mice are dependent on the SC20 and KCo5 transgenes for expression of kappa light chain containing antibodies. They can also form hybrid human/mouse antibodies because the endogenous mouse lambda light chain locus remains functional. The mice may also express chimeric human/mouse antibodies that comprise human heavy chain V region and mouse non-mu heavy chain isotype constant region sequences. These chimeric antibodies could be formed by chromosomal translocations of the human SC20 IgH locus into the mouse IgH locus mediated by class switching. Such “trans-switching” events were previously found to occur in mice containing mini-locus heavy chain transgenes (Taylor, L. et al., 1994, *Int. Immunol.* 6:579–591). Cross-breeding between 40 male Kco5/CMD/JKD mice and 98 female hCF(SC20)/CM2D/CKD mice resulted in 305 pups. ELISA analysis (Tomizuka, K. et al., 2000, *Proc. Natl. Acad. Sci. U.S.A.* 97:722–727) of serum samples prepared from these pups revealed that 125 of 305 (41%) pups were positive for human Ig μ chain expression. Further analysis detecting the human Ig κ chain showed that all the hμ-positive individuals were also hκ-positive, indicating the retention of KCo5 transgene (see Example 2). The PCR analysis of tail DNAs using D14S1419 and D14S1420 primer pairs (Tomizuka, K. et al., 2000, *Proc. Natl. Acad. Sci. U.S.A.* 97, 722–727) for detection of the hCF(SC20) showed that all the hμ-positive individuals retained the hCF(SC20) and all the hμ-negative individuals were negative for the hCF(SC20). The transmission efficiency of the hCF(SC20) from the female hCF (SC20)/CM2D/CKD (41%) was consistent with the data previously reported (Tomizuka, K. et al., 2000, *Proc. Natl. Acad. Sci. U.S.A.* 97:722–727).

Example 4

Expression of Human Ig in the Sera of Cross-bred Mice

Figure 2:
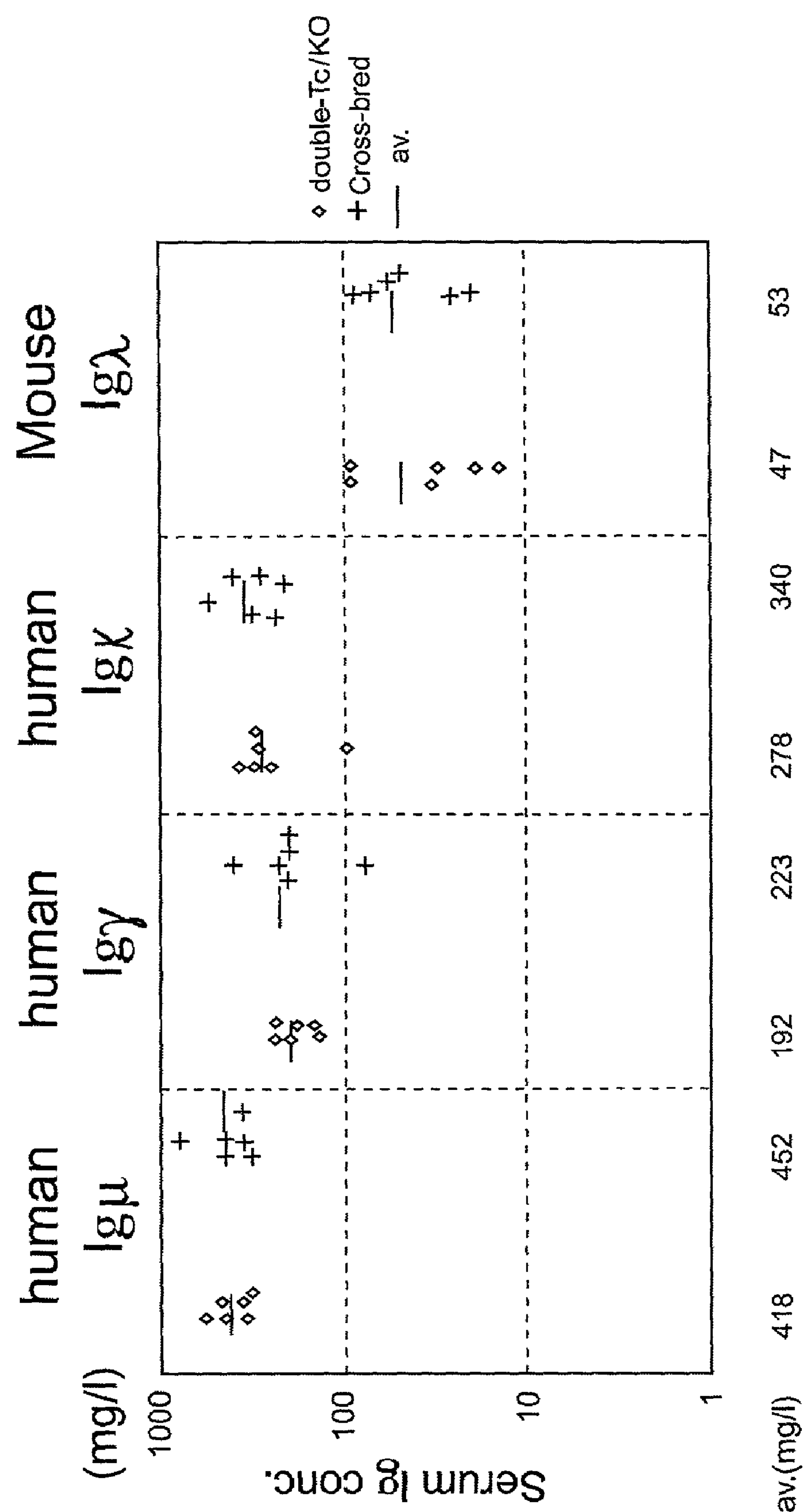
FIG. 2. Serum concentrations of human Ig μ, γ, κ and mouse lambda chains in the double TC/KO and cross-bred mice.
Figure 3:
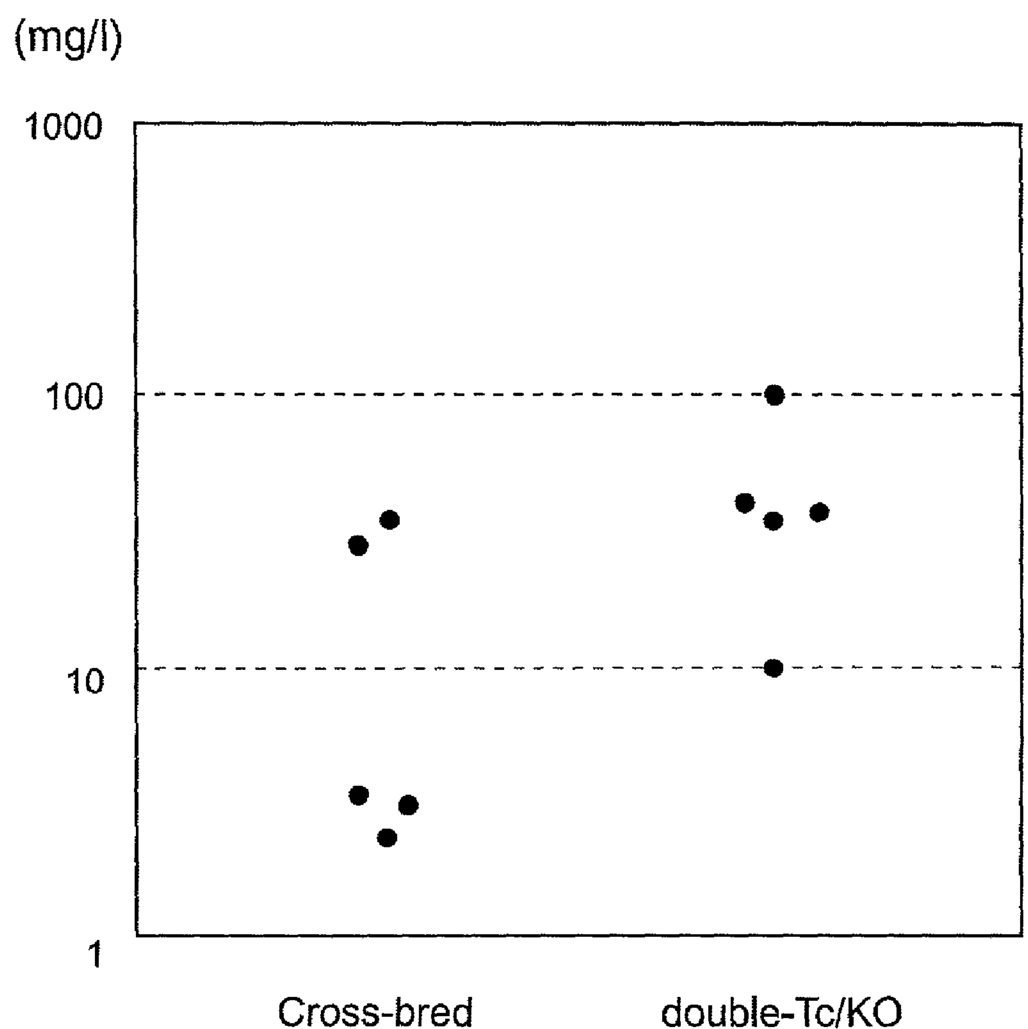
FIG. 3. Serum concentrations of anti-CD4 human Ig γ in the immunized double TC/KO and cross-bred mice on Day 34.
Figure 4:
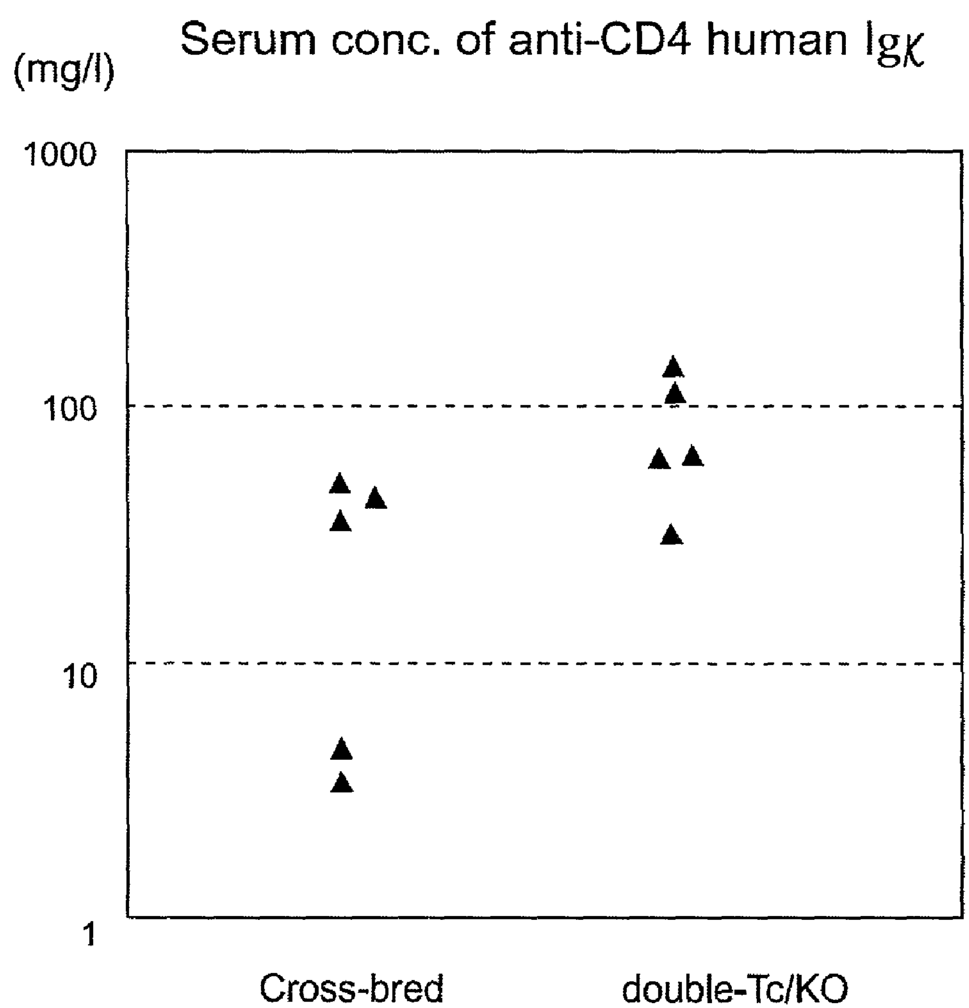
FIG. 4. Serum concentrations of anti-CD4 human Ig κ in the immunized double TC/KO and cross-bred mice on Day 34.
Figure 5:
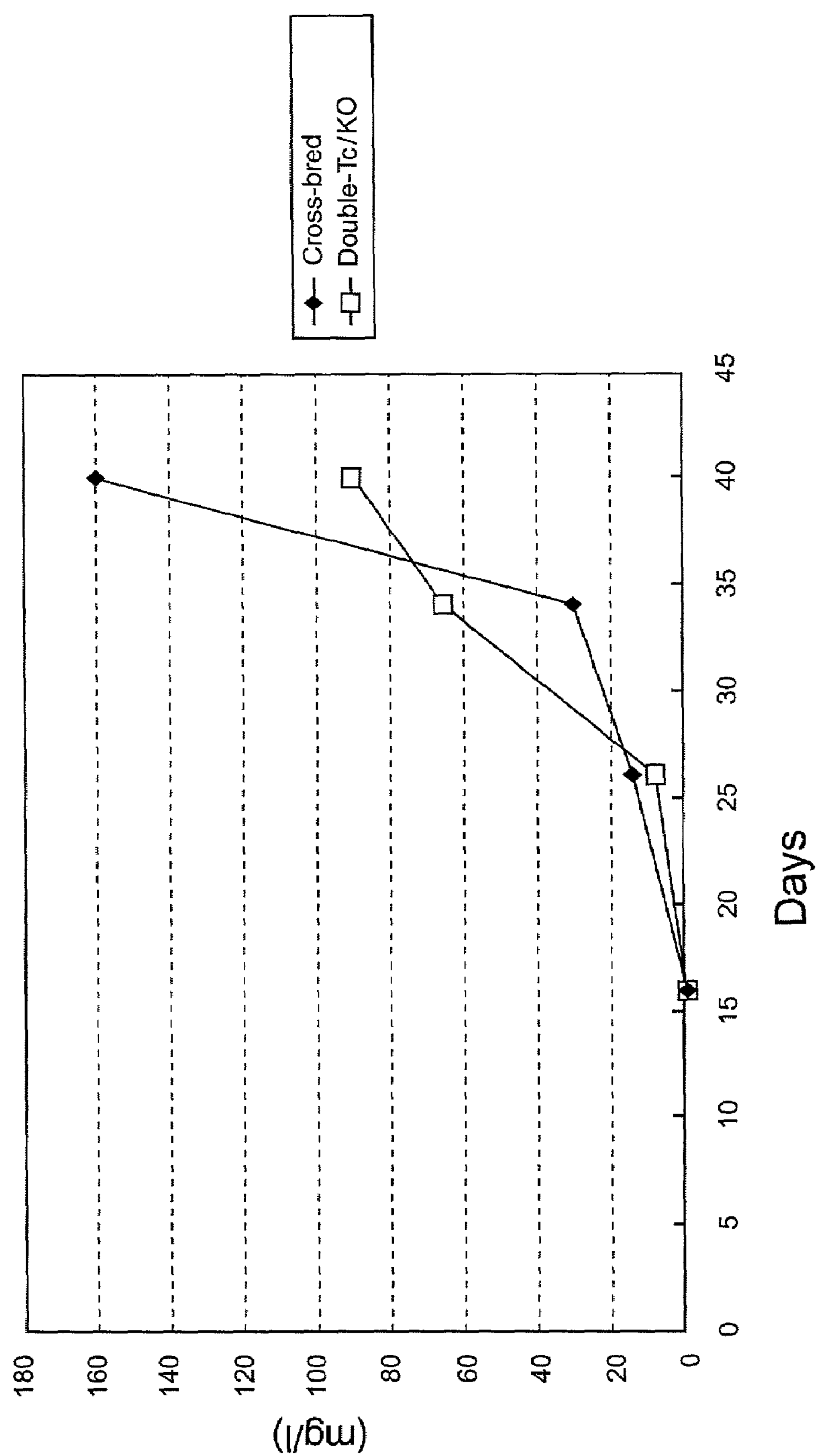
FIG. 5. Time course of anti-CD4 human Ig γ response in the double TC/KO and cross-bred mice that showed the highest serum titer among each group (N=5) on Day 34.
Figure 6:
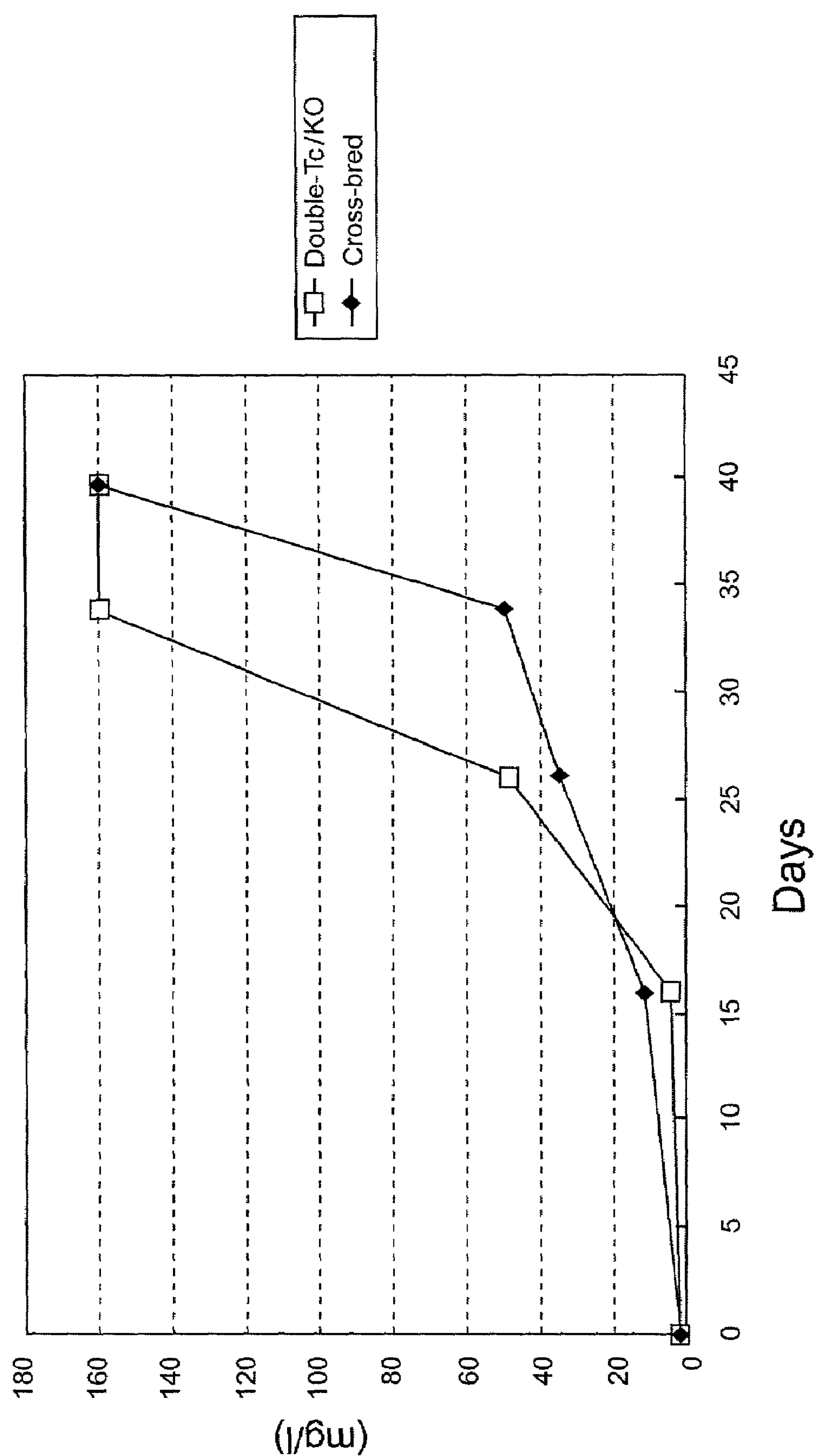
FIG. 6. Time course of anti-CD4 human Ig κ response in the double TC/KO and cross-bred mice that showed the highest serum titer among each group (N=5) on Day 34.

Serum samples prepared from 6–12 week old cross-bred mice were examined by ELISAs to determine concentrations of human Ig, μ, γ, κ and mouse λ chains (FIG. 2). Compared with the mice hemizygous for endogenous Cμ deletion, kept under similar conditions, the average levels of human Ig μ and Ig γ were higher than mouse μ, chain level (273 mg/l) and one third of the mouse γ chain level (590 mg/l), respectively. These heavy chain expression levels are similar to those of double-Tc/double-KO mice (hCF(SC20)/hCF(2-W23)/CM2D/CKD Tomizuka, K. et al., 2000, *Proc. Natl. Acad Sci U.S.A.* 97:722–727). One fourth of F2 offspring produced by mating between male and female cross-bred mice were expected to be homozygous for the mλC1 (λlow) mutation because the first generation of cross-bred mice were heterozygous for this mutation. Serum concentrations of human Ig κ and mouse Ig λ light chains were determined by ELISA in twenty one F2 cross-bred mice as described in the previous report (Tomizuka, K. et al., 2000, *Proc. Natl. Acad. Sci. U.S.A.* 97:722–727). Of 21 mice examined, six mice exhibited low (<0.1) mouse λ/human κ ratio, which is characteristics of mice homozygous for the λ low mutation (Tomizuka, K. et al., 2000, *Proc. Natl. Acad. Sci. U.S.A.* 97:722–727). Thus, these six cross-bred mice may be homozygous for the λ(low) mutation, which can be useful for efficient production of hybridomas that secrete antibodies comprising human Ig heavy and κ light chains.

Example 5

Production of Anti-human CD4 Human Monoclonal Antibodies

Immunization of antigen. Cross-bred mice and double-Tc/KO mice (n=5) were immunized by subcutaneous injections with 100 μg of soluble human CD4 (sCD4) in complete Freund’s adjuvant (Sigma) on day 0, followed by immunizations in incomplete Freund’s adjuvant (Sigma) on day 9, 19, and 27. A final intravenous injection of 40 μg of sCD4 in PBS was given on day 37.

Humoral responses in mice. Serum was collected on days 0, 16, 26, 34 and 40. Antigen-specific human Igγ and Igκ were measured by enzyme-linked immunosorbent assay (ELISA) for production of monoclonal antibodies (MAbs) to sCD4. Detailed protocol for ELISA is described Example 4. Antigen-specific plates were coated with antigen at 1 μg/ml in bicarbonate buffer (Sigma) overnight. Antigen-specific Igγ and Igκ were quantified using one of human monoclonal IgG specific for antigen as a standard. The results are shown in FIGS. 3, 4, 5 and 6. Human gamma and kappa responses were observed 34 days after initiation of immunizations in cross-bred mice and double-Tc/double-KO mice.

Generation of hybridomas. Splenocytes from immunized mice were fused to Sp2/0-Ag14 cells on day 40. The cell suspension were inoculated into 384-well plates at 20 thousands of splenocytes per well. Resulting hybridomas were screened for production of monoclonal antibodies (MAbs) to sCD4. The results are shown below in Table 1.

TABLE 1

Production of CD4 monoclonal antibodies

| | Cross-bred | Double-Tc/KO |
|---|---|---|
| Number of wells with colonies | 1265 | 720 |
| Number of antigen specific hγ/hκ positive wells | 18 | 4 |
| Number of antigen specific hγ/mλ positive wells | 0 | 0 |
| Number of subcloned parental wells | 14 | 1 |
| Efficiency of subcloning (%) | 88 | 21 |

The parental hybridomas from cross-bred mouse were subcloned by two rounds of limiting dilution with high efficiency. All of hybridomas from cross-bred mouse secreted human γ/human κ anti-CD4 MAbs and none of hybridomas secreted human γ/murine κ anti-CD4 MAbs. These data indicated that cross-bred mouse is superior to the double TC/KO strain for generation of antigen-specific human monoclonal antibodies. The isotype of the MAbs secreted by these subcloned hybridomas was further examined by a number of ELISAs. Seven wells were hγ1$^+$ and 7 wells were hγ4$^+$.

Figure 7:
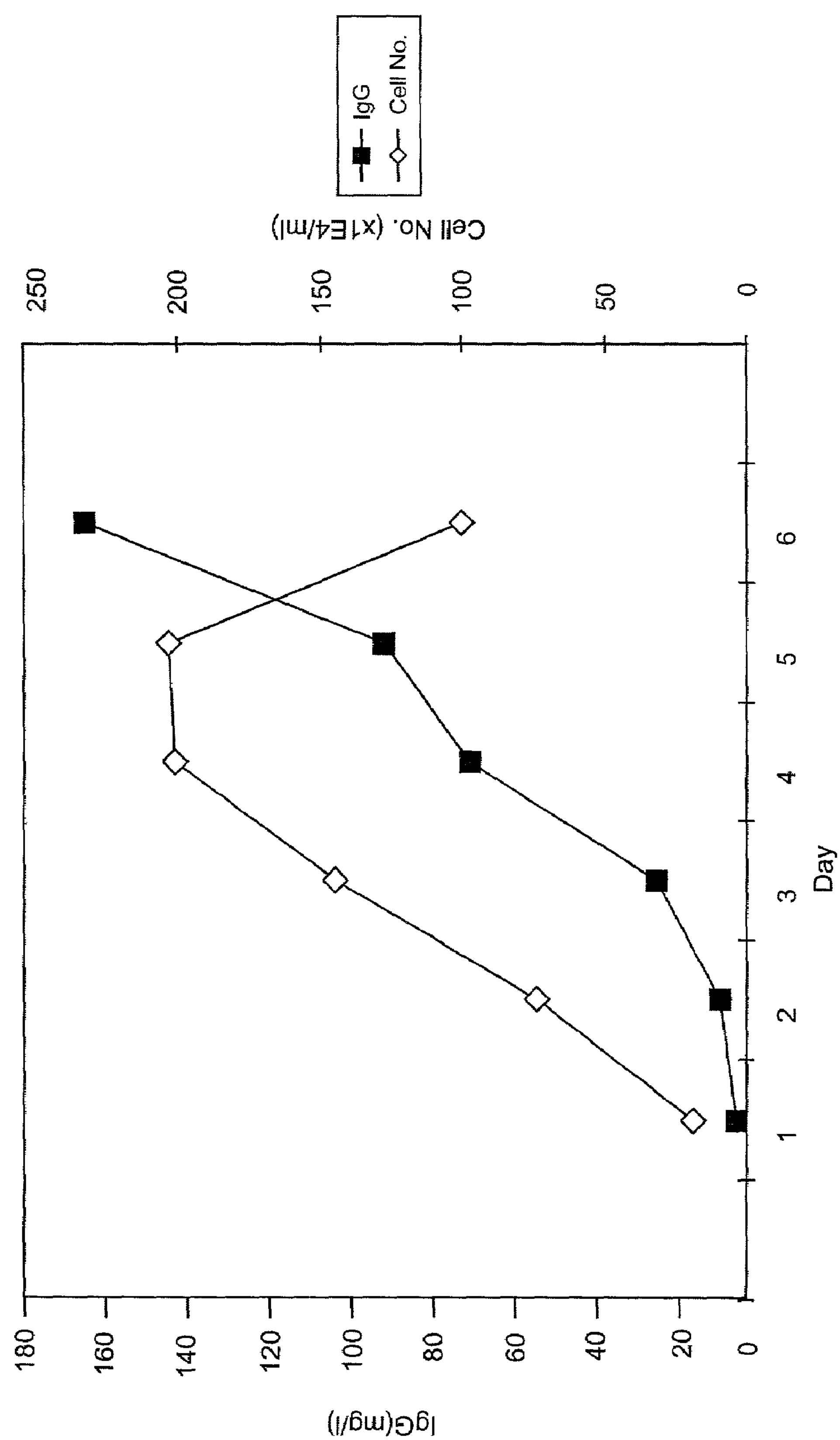
FIG. 7. Growth curve and anti-CD4 human monoclonal antibody production of the KM2-3 hybridoma cells.
Figure 8:
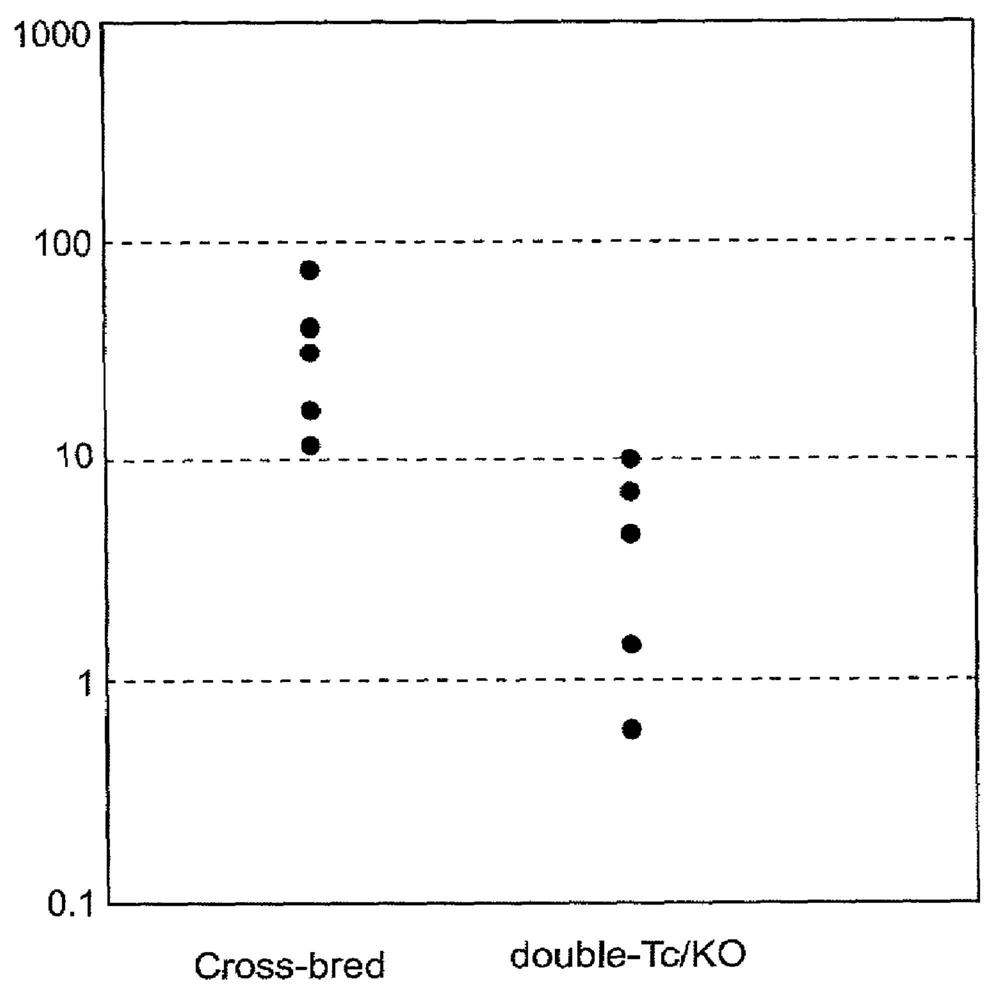
FIG. 8. Serum concentrations of anti-GCSF human Ig γ in the immunized double TCIKO and cross-bred mice on Day 34.
Figure 9:
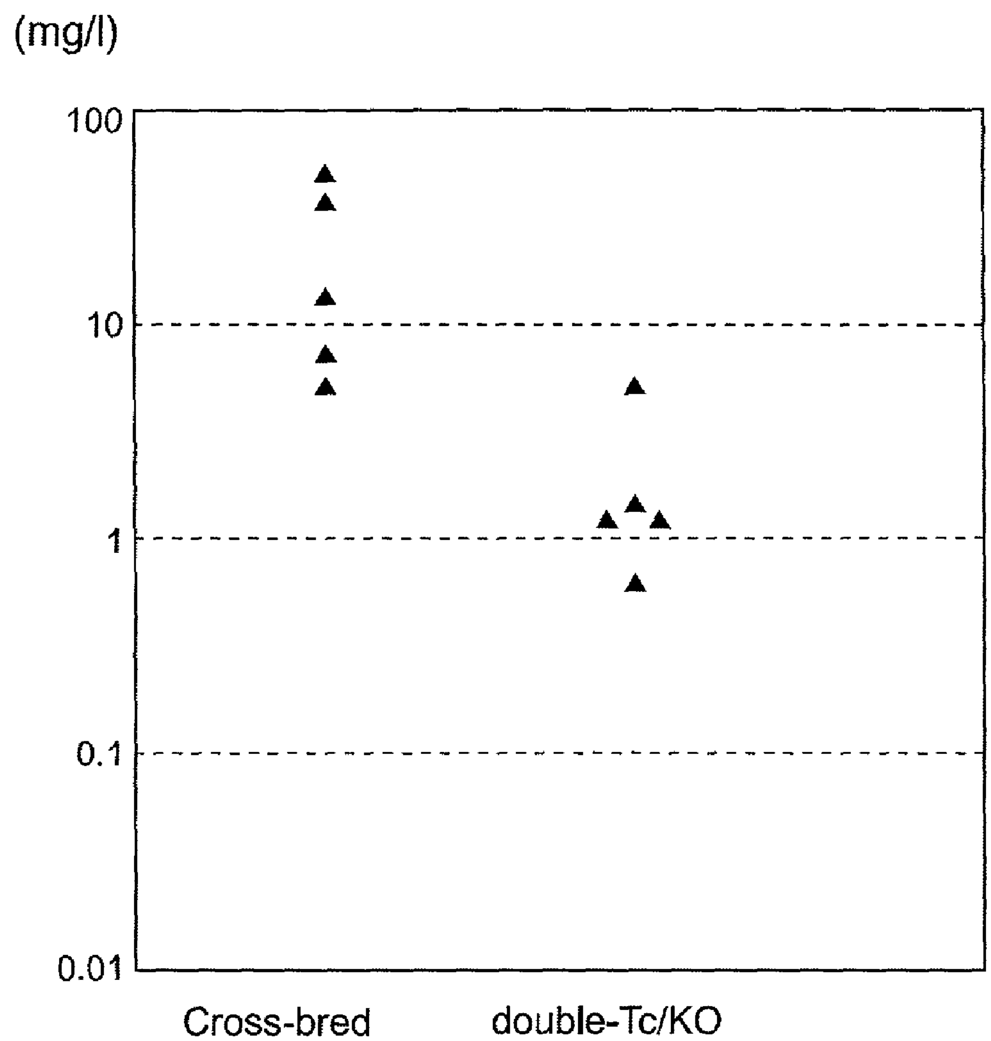
FIG. 9. Serum concentrations of anti-GCSF human Ig κ in the immunized double TC/KO and cross-bred mice on Day 34.
Figure 10:
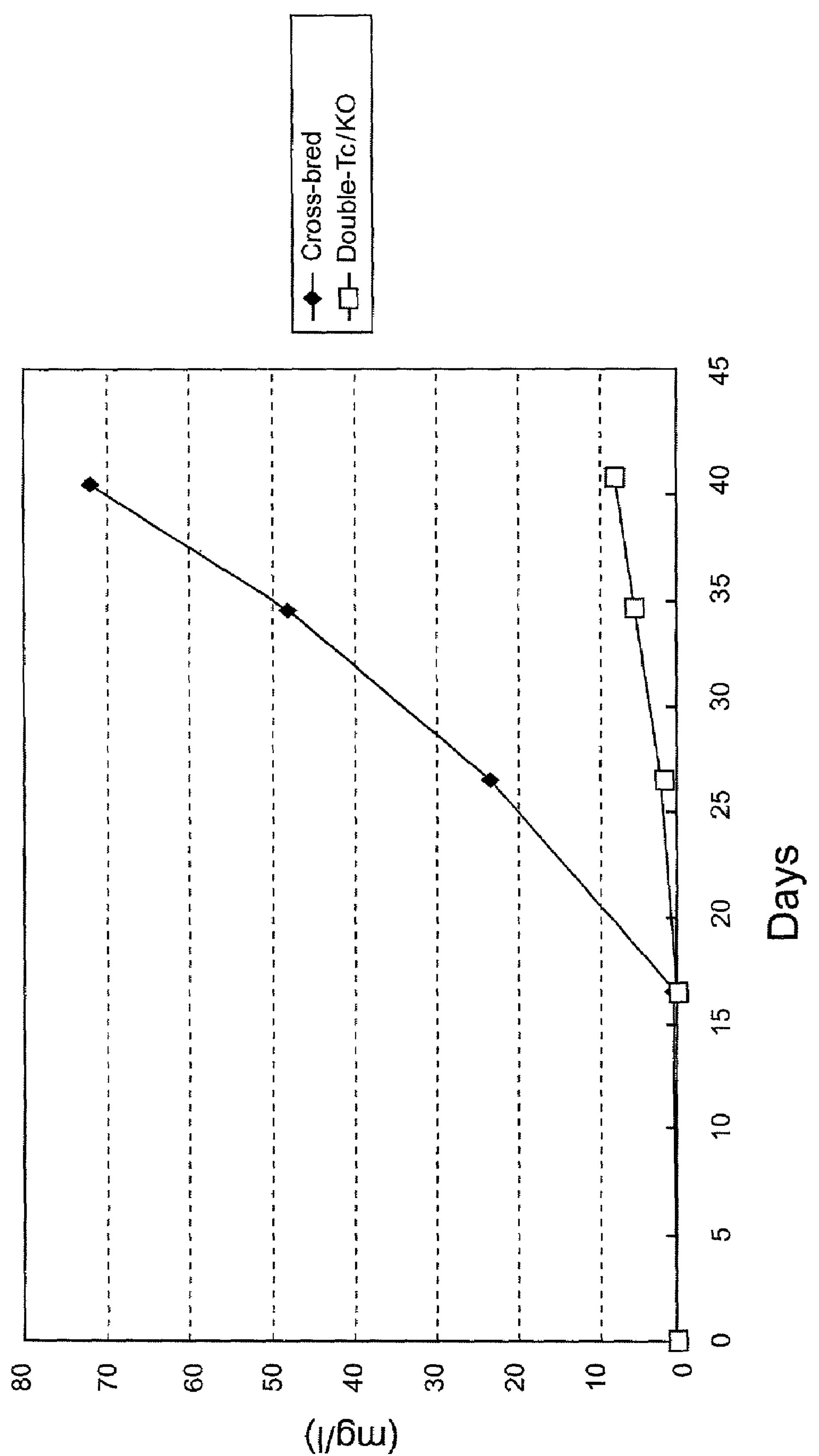
FIG. 10. Time course of anti-GCSF human Ig γ response in the double TC/KO and cross-bred mice that showed the highest serum titer among each group (N=5) on Day 34.
Figure 11:
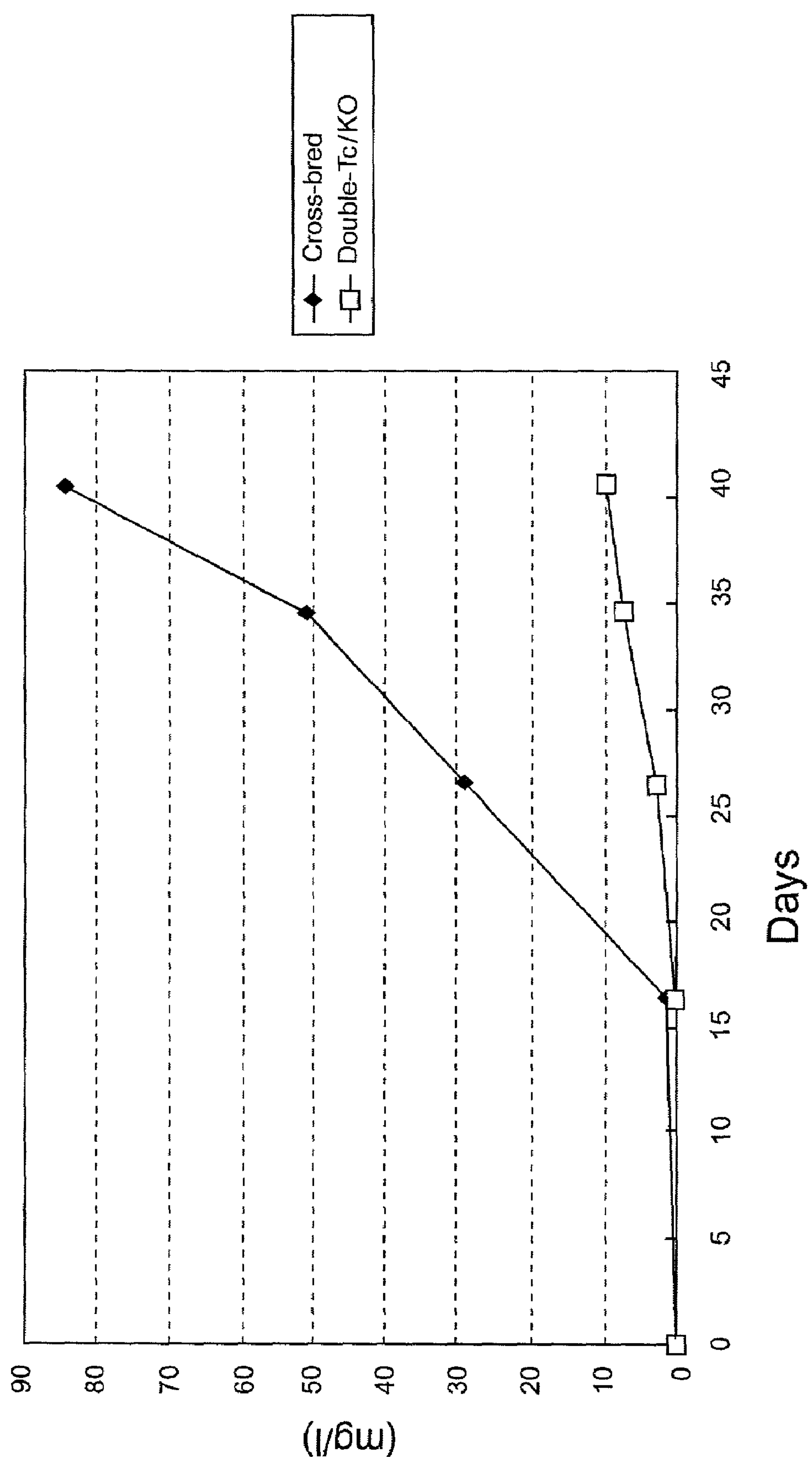
FIG. 11. Time course of anti-GCSF human Ig κ response in the double TC/KO and cross-bred mice that showed the highest serum titer among each group (N=5) on Day 34.

Growth Curve and Secretion Levels for an Anti-CD4Human $IgG_1$ Monoclonal Antibody in Small Scale Cultures. One of the hybridoma clones producing anti-CD4 human $IgG_{1\kappa}$ (KM2-3) was used for the determination of growth curve and secretion levels for the human monoclonal antibody in small scale cultures. KM2-3 hybridoma cells were seeded in 4 liter spinner flask (Bellco) at 1×10$^5$ cells/ml on day 0. One liter of ERDF medium supplied with ITS-X (Gibco BRL) and 1% low IgG serum (Hyclone) was used for culture. One ml of medium was collected every day, and the cell number and $IgG_{1\kappa}$ concentration was measured by ELI SA as described in the previous report (Tomizuka, K. et al., 2000, *Proc. Natl. Acad. Sci. U.S.A.* 97:722–727). The results were presented in FIG. 7. Estimated production rate was 24.6 pg/cell/day, which is within a range similar to that expected for excellent murine hybridomas under these conditions.

Example 6

Generation of Anti-human G-CSF Human Monoclonal Antibodies

Immunization of antigen. Cross-bred mice and double-Tc/KO mice (n=5) were immunized by subcutaneous injections with 100 g of soluble human G-CSF in TiterMaxGold adjuvant (CytRx) on day 0, 9, 19, 27. A final intravenous injection of 20 g of G-CSF in PBS was given to cross-bred mouse and double-Tc/KO mouse on day 37.

Humoral responses in each strain of mice. Serum was collected on days 0, 16, 26, 34 and 40. Concentrations of antigen-specific human Igs were quantified by ELISA. Antigen-specific plates were coated with antigen at 1 μg/ml in bicarbonate buffer (Sigma) overnight. Antigen-specific Igγ and Igκ were quantified using one of human monoclonal IgG specific for G-CSF as a standard. The results are shown in FIGS. 8, 9, 10 and 11. Concentration of antigen-specific hγ and hκ in the serum of cross-bred mice were about 10-fold higher than that of double-Tc/KO mice.

Productions of hybridomas. Splenocytes from immunized mice were fused to Sp2/0-Ag14 cells on day 40 and resulting hybridomas were screened by ELISA for production of monoclonal antibodies (MAbs) to G-CSF. The results are shown below in Table 2.

TABLE 2

Production of G-CSF monoclonal antibodies

| | Cross-bred | Double-Tc-KO |
|---|---|---|
| Number of wells with colonies | 3880 | 1580 |
| Number of antigen specific hγ/hκ positive wells | 13 | 3 |
| Number of antigen specific hγ/mλ positive wells | 13 | 0 |
| Number of subcloned parental wells | 11 | 2 |
| Efficiency of subcloning (%) | 83 | 64 |

Half of anti-G-CSF IgG producing hybridomas secreted human γ/human κ anti-G-CSF MAbs and remaining of hybridomas secreted human γ/murine κ anti-G-CSF MAbs. Hybridomas producing hγ/hκ antibodies were subcloned by two rounds of limiting dilution. Further ELISA experiments demonstrated that 5, 3, and 3 wells were hγ1$^+$, hγ2$^+$, and hγ4$^+$, respectively.

Example 7

Generation of Anti-human Serum Albumin Human Monoclonal Antibodies

Cross-bred mice were immunized by intraperitonial injections with 50 μg of human serum albumin in complete Freund's adjuvant (Sigma) on day 0, followed by immunizations in incomplete Freund's adjuvant (Sigma) on day 7, 14, and 21.

Generation of hybridomas. Splenocytes from immunized mice were fused to Sp2/0-Ag14 cells on day 24 and resulting hybridomas were screened by ELISA for production of monoclonal antibodies (MAbs) to antigen. Ten wells of hybridomas were chosen randomly from anti-albumin hγ producing hybridomas and subcloned. All of hybridomas secreted human γ/human κ anti-albumin. This data indicate that cross-bred mouse is superior to double-Tc/double-KO mouse for production of antigen-specific fully human monoclonal antibodies since two-thirds of anti-albumin IgG hybridomas obtained from double-Tc/double-KO mouse were mλ$^+$ (Tomizuka, K. et al., 2000, *Proc. Natl. Acad. Sci. U.S.A.* 97:722–727).

Example 8

Generation of Anti-human CTLA-4 Monoclonal Antibodies

Antigen. A DNA segment encoding a fusion protein comprising sequences from the human CTLA-4 and the murine CD3ζ genes was constructed by PCR amplification of cDNA clones together with bridging synthetic oligonucleotides. The encoded fusion protein contains the following sequences: i.) human CTLA-4 encoding amino acids 1–190 (containing the signal peptide, the extracellular domain of human CTLA-4 and the entirety of the presumed transmembrane sequence of human CTLA-4) and ii.) murine CD3ζ from amino acid 52 to the carboxy terminus. The amplified PCR product was cloned into a plasmid vector and the DNA sequence was determined. The cloned insert was then subcloned into the vector pBABE (which contains a gene encoding for puromycin resistance (Morganstem, JP and Land, H, 1990 *Nucl. Acids Res.* 18:3587–96) to create pBABE-huCTLA-4/CD3ζ. pBABE-huCTLA-4/CD3ζ was transfected into the retroviral packaging line, ψ-2, and a pool of puromycin resistant cells were selected. These cells were co-cultured with the murine T cell hybridoma BW5147 (ATCC #TIB-47). After 2 days of co-culture the non-adherent BW5147 cells were removed and selected for resistance to puromycin. The puromycin resistant cell pool was subcloned by limiting dilution and tested for surface expression of human CTLA-4 by FACS. A clone expressing high levels of human CTLA-4 at the cell surface was selected (BW-huCTLA-4CD3ζ-3#12). Soluble recombinant antigen comprising the extracellular domain of human CTLA-4 was purchased from R&D Systems (Cat. #325-CT-200).

Immunization. Three SC20/KCo5 cross-bred mice (ID#'s 22227, 22230, and 22231) were each immunized by intraperitoneal (i.p.) injection of 10e7 washed whole BW-huCTLA-4CD3ζ-3#12 cells expressing the human CTLA-4 extracellular domain. This immunization procedure was repeated two more times at approximately one month intervals for mice #22227 and 22230. At month 3, Mouse #22231 was given a third i.p. injection of whole washed cells, while mice #22227 and 22230 were each injected i.p. and subcutaneously (s.c.) with 20 micrograms of soluble recombinant antigen in MPL+TDM adjuvant (Sigma Cat. # M6536). The mice were then rested for 10 days and then two days prior to harvesting of spleen cells for hybridoma fusion, mice # 22227 and 22230 were each given tail vein (i.v.) injections of 20 micrograms soluble recombinant antigen together with i.p. injections of 20 micrograms of soluble recombinant antigen in MPL+TDM adjuvant. One day prior to harvesting splenocytes, these mice were given an additional i.v. injection of 20 micrograms of soluble recombinant antigen. Mouse #22231 was given 10e7 washed BW-huCTLA-4CD3ζ-3#12 cells in MPL+TDM adjuvant i.p. three days prior to harvesting spleen cells, followed by $10^7$ washed BW-huCTLA-4CD3ζ-3#12 cells without adjuvant i.p. two days prior to fusion.

Fusion. Spleen cells from mice #22227, 22230, and 22231 were fused, in three separate experiments, with mouse myeloma cells (line P3 X63 Ag8.6.53, ATCC CRL 1580, or SP2/0-Ag14, ATCC CRL 1581) by standard procedures (Harlow and Lane, 1988, Antibodies, A Laboratory Manual, Cold Spring Harbor Laboratory Press, Cold Spring Harbor N.Y.; Kennett et al., 1980, Monoclonal Antibodies, Hybridomas:A New Dimension in Biological Analysis. Plenum, New York; Oi and Herzenberg, 1980, *Immunoglobulin Producing Hybrid Cell Lines*, in SELECTED METHODS IN CELLULAR IMMUNOLOGY, ed. Mishell and Shiigi, pp. 357–372. Freeman, San Francisco; Halk, 1984, Methods in Enzymology:Plant Molecular Biology, ed. Weissbach and Weissbach, pp. 766–780, Academic Press, Orlando, Fla.). Cells were cultured in DMEM, 10% FBS, OPI (Sigma O-5003), BME (Gibco 21985-023), and 3% Origen Hybridoma Cloning Factor (Igen IG50-0615). HAT or HT supplement was added to the medium during initial growth and selection.

Hybridoma Screening. To identify hybridomas secreting antigen reactive human IgG antibodies, ELISA plates (Nunc MaxiSorp) were coated overnight at 4° C. with 100 l/well Human CD152 Mu-Ig fusion (Ancel # 501-820) at 0.2 μg/ml in PBS. Plates were washed and blocked with 100 μl/well PBS-Tween containing 1% BSA. Fifty μl of cell culture supernatant was added followed by a 1–2 hour incubation. Plates were washed and then incubated for one hour with 100 μl/well goat anti-human gamma heavy chain conjugated to alkaline phosphatase (Anti-human gamma (fc) AP Jackson # 109-056-098). Plates were washed three times in PBS-Tween between each step. Seventy six hybridomas were identified that secreted gamma positive, antigen reactive antibody. These clones were then further analyzed to determine the gamma heavy chain or light chain isotype, as well as the presence of contaminating IgM secreting cells (Table 3).

TABLE 3

Analysis of heavy chain isotypes from 1° hybridoma wells comprising antigen reactive human IgG antibodies.

| Mouse ID # | IgM | $IgG_1$ | $IgG_2$ | $IgG_3$ | $IgG_4$ | Igκ | Igλ | All IgG |
|---|---|---|---|---|---|---|---|---|
| 22227 | 0 | 4 | 1 | 0 | 3 | 7 | 0 | 8 |
| 22230 | 9 | 25 | 8 | 5 | 7 | 48 | 6 | 45 |
| 22231 | 1 | 11 | 2 | 3 | 7 | 23 | 1 | 23 |
| total | 10 | 40 | 11 | 8 | 17 | 75 | 7 | 76 |

Hybridoma supernatants were first tested for the presence of antigen reactive human IgG. Seventy six positive supernatants were then tested for antigen reactive human IgM, $IgG_1$, $IgG_2$, $IgG_3$, $IgG_4$, Igκ, and mouse Igλ. Capture reagent:human CD152 mu-Ig fusion (Ancel # 501-820). Detecting reagents:anti-human gamma (fc) HRP (Jackson # 109-036-098); anti-human kappa HRP (Bethyl # A80-115P); anti-human gamma 1 HRP (Southern Biotech #9050-05); anti-human gamma 2HRP (Southern Biotech #9070-05); anti-human gamma 3HRP (Southern Biotech #9210-05); anti-human gamma 4HRP (Southern Biotech #9200-05); anti-human mu HRP (Southern Biotech #1060-05).

Seventy five of the 76 IgG antigen positive wells were also positive for human kappa light chain antigen reactive antibody, while 7 of the wells were positive for mouse lambda containing hybrid antibody. However, 6 of the 7 lambda positive wells also contained kappa light chain, and 3 of these three wells were positive for contaminating IgM antigen reactive antibody. Because these contaminating IgM antibodies may have contributed include the lambda light chain, there are between 3 and 7 IgGλ clones out of the total of 76 IgG clones. Thus, the endogenous mouse lambda appears to contribute to only 4 to 9% of the IgG positive, antigen reactive hybridomas. Cells from 22 of the 76 positive hybridoma wells were then re-plated at limiting dilution to subclone individual monoclonal antibody secreting hybridomas. Stable antigen reactive, human IgG subclones were obtained from 19 out of 22 of the 1° hybridomas (see Table 4 below).

TABLE 4

Subcloning of Anti-CTLA-4 Hybridomas

| Clone | OD | # Clones Tested | # Positive | % Positive |
|---|---|---|---|---|
| 4C1 | 0.44 | 24 | 5 | 21% |
| 2E4 | 1.48 | 24 | 9 | 38% |
| 1H5 | 1.39 | 24 | 14 | 58% |
| 9C4 | 1.30 | 24 | 5 | 21% |
| 6D11 | 3.24 | 16 | 10 | 63% |
| 10H3 | 1.59 | 16 | 2 | 13% |
| 8H4 | 3.14 | 16 | 7 | 44% |
| 8G5 | 1.38 | 8 | 3 | 38% |
| 4A9 | 1.35 | 24 | 20 | 83% |
| 10E1 | 1.17 | 24 | 3 | 13% |
| 9F6 | 1.08 | 24 | 0 | 0% |
| 6B9 | 1.16 | 16 | 5 | 31% |
| 9B10 | 2.70 | 32 | 9 | 28% |
| 10D1 | 0.90 | 48 | 6 | 13% |
| 1B6 | 1.34 | 24 | 9 | 38% |
| 4C7 | 1.34 | 8 | 2 | 25% |
| 1D11 | 0.97 | 8 | 0 | 0% |
| 1B5 | 2.75 | 8 | 3 | 38% |
| 4E9 | 1.36 | 24 | 1 | 4% |
| 11H7 | 0.40 | 16 | 0 | 0% |
| 2D8 | 1.31 | 24 | 10 | 42% |
| 8F2 | 1.28 | 16 | 5 | 31% |

Thus 86% subcloning efficiency was obtained. On subcloning, it was found that one of the 1° hybridomas comprised 2 distinct clones, having different IgG isotypes (see Table 5 below).

TABLE 5

Isotype analysis of human IgGκ anti CTLA-4 subclones

| Mouse | Clone | Parent Well | $IgG_1κ$ | $IgG_2κ$ | $IgG_3κ$ | $IgG_4κ$ |
|---|---|---|---|---|---|---|
| 22227 | 8G5 | $IgG_1κ$ | + | – | – | – |
| 22227 | 6B9 | $IgG_1κ$ | + | – | – | – |
| 22230 | 1B5 | $IgG_3κ$ | – | – | + | – |
| 22230 | 2D8 | $IgG_1κ$ | + | – | – | – |
| 22230 | 6D11 | $IgG_4κ$ | – | – | – | + |
| 22230 | 8H4 | $IgG_4κ$ | – | – | – | + |
| 22230 | 9C4 | $IgG_3κ$ | – | – | + | – |

TABLE 5-continued

Isotype analysis of human IgGκ anti CTLA-4 subclones

| Mouse | Clone | Parent Well | $IgG_1κ$ | $IgG_2κ$ | $IgG_3κ$ | $IgG_4κ$ |
|---|---|---|---|---|---|---|
| 22230 | 10H3 | $IgG_3κ$ | − | − | + | − |
| 22231 | 1B6 | $IgG_1κ$ | + | − | − | − |
| 22231 | 1H5 | $IgG_1κ$ | + | − | − | − |
| 22231 | 2E4 | $IgG_1κ$ | + | − | − | − |
| 22231 | 4A9 | $IgG_1κ$ | + | − | − | − |
| 22231 | 4C1.1 | $IgG_4κ$ | − | − | − | + |
| 22231 | 9B10 | $IgG_1κ$ | + | − | − | − |
| 22231 | 4C7 | $IgG_3κ$ | − | − | + | − |
| 22231 | 10D1.1 | $IgG_1κ$, $IgG_4κ$ | + | − | − | − |
| 22231 | 10D1.4 | $IgG_1κ$, $IgG_4κ$ | − | − | − | + |
| 22231 | 10E1 | $IgG_4κ$ | − | − | − | + |
| 22231 | 8F2 | $IgG_1κ$ | + | − | − | − |
| 22231 | 4E9 | $IgG_1κ$ | + | − | − | − |

Thus, 20 different subclones were obtained. All 20 clones use the human κ light chain, and are fully human.

Figure 12:
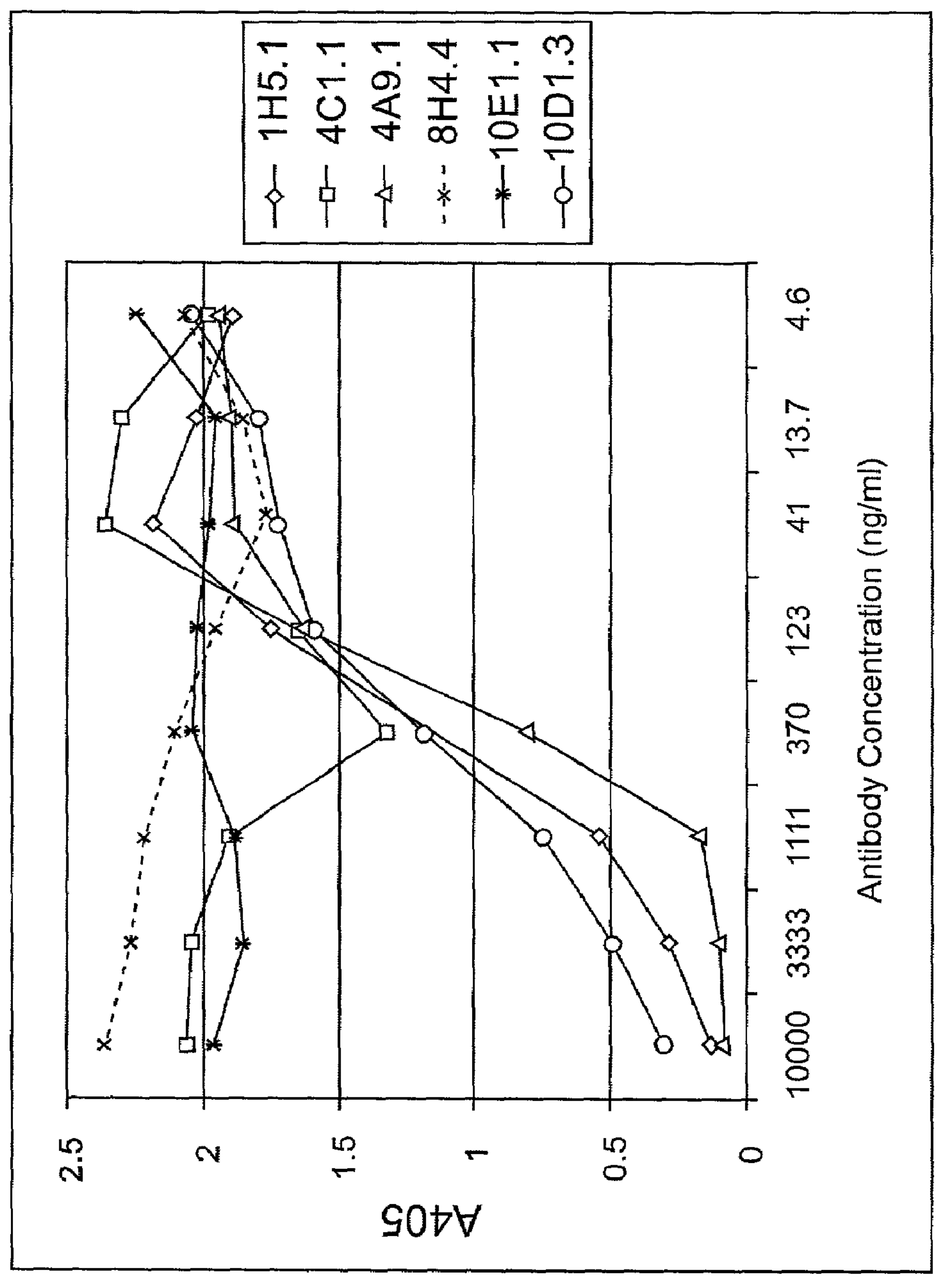
FIG. 12. Dose response curves of anti-CTLA-4 human monoclonal antibodies for blocking activity.
Figure 13:
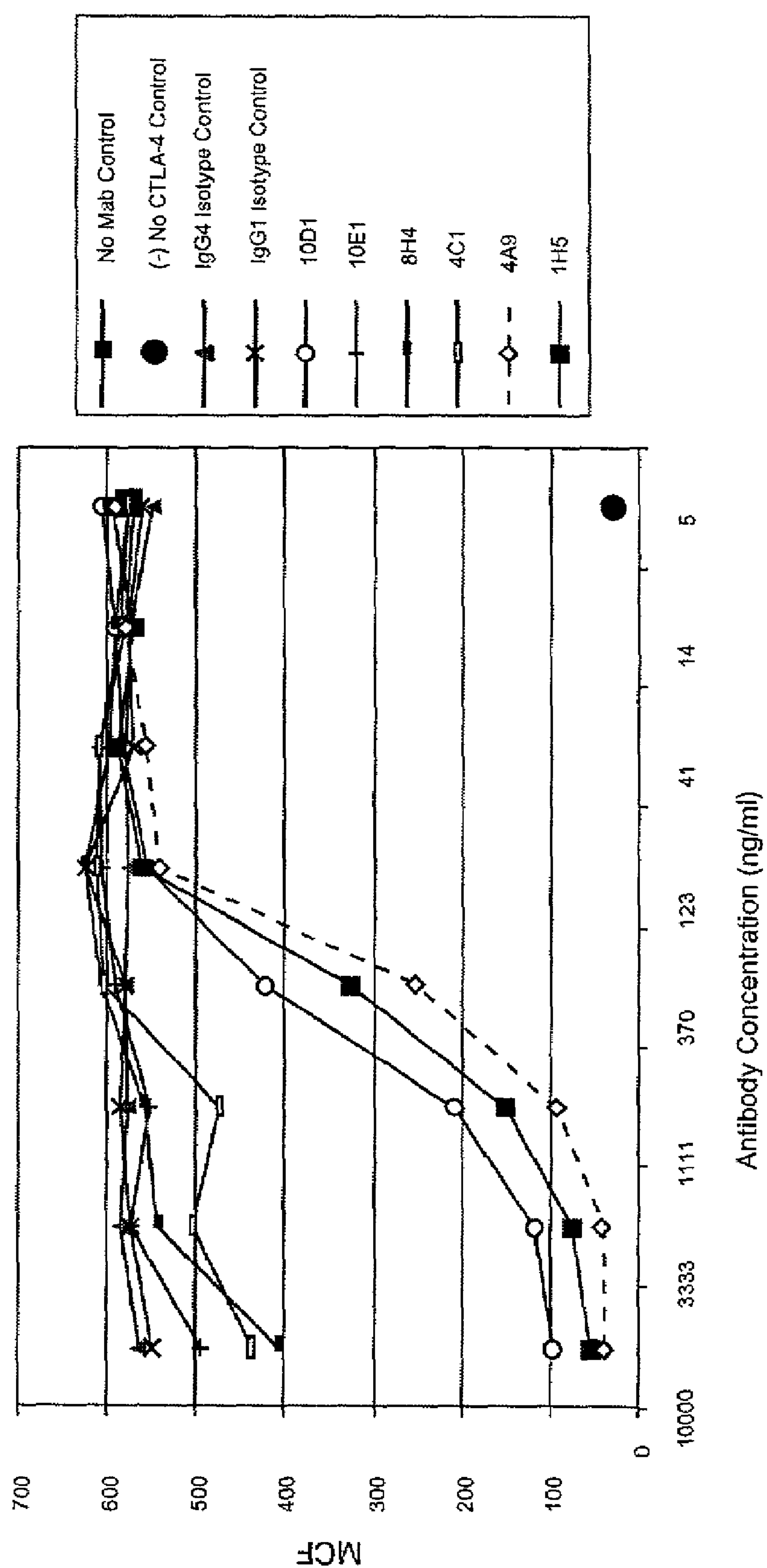
FIG. 13. Inhibition of CTLA-4(biotin) binding to B7.2 cells with monoclonal antibodies.

Monoclonal antibodies were isolated from five of the subcloned hybridomas (1H5, 4A9, 4C1, 8H4, and 10E1) and tested for their ability to block CTLA-4 binding to B7.2 (FIGS. 12 and 13).

Briefly, an ELISA plate was coated with a B7.2 Ig fusion protein at 0.7 μg/ml (100 μl/well)(see WO 01/14424, which is incorporated by reference in its entirety for all purposes). The plate was washed and blocked in PBS-T +1% BSA for 30 minutes. Antibody was mixed with an equal volume of biotin labeled CTLA-4 Ig (Ancell #501-030) at 0.2 μg/ml and pre-incubated for 1 hr at room temperature, then transferred to B7.2 coated ELISA plate and incubated for 1 hr. Plates were washed and 100 μl/well of streptavidin alkaline phosphatase (Kirkegaard and Perry Labs 15-30-0) was added and incubated for 1 hr. Plates were developed with pnpp substrate. Inhibition of biotin labeled CTLA-4 binding to B7.2 is plotted as antibody concentration versus absorbance at 405 nm. Antibody 10D1 is a CTLA-4 specific human $IgG_1$ (see WO 01/14424). Antibody isotypes are 1H5.1 ($\gamma_1$), 4A9.1 ($\gamma_1$) ($\gamma_4$), 8H4.4 ($\gamma_4$), 10E1.1($\gamma_4$), and 10D1 ($\gamma_1$).

Two of the antibodies (1H5 and 4A9) were found to be blocking antibodies, and three (4C1, 8H4, and 10E1) were found to be nonblocking antibodies (FIGS. 12 and 13).

Administration of anti-CTLA-4 can enhance T cell mediated immune responses (Krummel, 1995, *J. Exp. Med.* 182:459–465; Krummel et al., 1996, *Int'l Immunol.* 8:519–523). Thus CTLA-4 antibodies can be used as an adjuvant to increase the immunogenicity of another agent. When antibodies to CTLA-4 are administered together with another agent, the two can be administered in either order or simultaneously. The methods can be used for a variety of vaccines and treatments for which enhanced immune responses are beneficial. For example infectious diseases and cancers, including melanoma, colon cancer, prostate cancer, and renal cancer.

CTLA-4 antibodies can also be used to down-modulate a T cell mediated immune response. This activity can be obtained with multivalent preparations of anti-CTLA-4 antibody. For example, latex microspheres coated with anti-CTLA-4 (to increase the valency of the antibody) can inhibit T cell proliferation and activation. Agents having the same antibody combining site may act as a CTLA-4 antagonist when presented as an Fab or a -soluble IgG, and a CTLA-4 agonist when highly cross-linked. Thus multivalent forms of anti-CTLA-4 antibodies can be useful therapeutic agents for immunosuppression.

In addition to linking to latex microspheres or other insoluble particles, the antibodies can be cross-linked to each other or genetically engineered to form multimers. Cross-linking can be by direct chemical linkage, or by indirect linkage such as an antibody-biotin-avidin complex. Cross-linking can be covalent, where chemical linking groups are employed, or non-covalent, where protein-protein or other protein-ligand interactions are employed. Genetic engineering approaches for linking include, e.g., the re-expression of the variable regions of high-affinity IgG antibodies in IgM expression vectors or any protein moiety (e.g., polylysine, and the like). Converting a high affinity IgG antibody to an IgM antibody can create a decavalent complex with very high avidity. $IgA_2$ expression vectors may also be used to produce multivalent antibody complexes. $IgA_2$ can form polymers together with J chain and secretory component. $IgA_2$ may have the added advantage that it can be additionally crosslinked by the IgA receptor CD89, which is expressed on neutrophils, macrophages, and monocytes. Alternatively, because approximately 2% of the hybridomas generated from the C20/KCo5 cross-bred mice are IgA, these animals can be used to directly generate a human IgA isotype anti-CTLA-4 antibody.

Agonism can also be obtained using some preparations of polyclonal antibodies to CTLA-4 comprising antibodies to at least two non-overlapping epitopes on CTLA-4. One antibody in such a preparation containing two binding sites can bind to two molecules of CTLA-4 to form a small cluster. A second antibody possessing different binding sites can then link (aggregate) these small clusters to form large clusters, thereby forming a complex of CTLA-4 (on the cell surface) that can transduce a signal to the T cell to inhibit, reduce or prevent activation of the T-cell bearing (expressing) CTLA-4. Thus, some preparations of polyclonal antibodies show similar agonism to the polyvalent preparations described above.

Therefore, polyvalent or polyclonal preparations of anti CTLA-4 antibodies are useful for agonizing the CTLA-4 receptor, thereby suppressing immune responses otherwise mediated by T cells bearing the CTLA-4 receptor. Some examples of diseases that can be treated using such polyvalent or polyclonal preparations of antibodies induce autoimmune disease, transplant rejection, and inflammation.

Example 9

Generation of Anti-human EGFR Antibodies

Antigen. Purified soluble epidermal growth factor receptor (EGFR) from human carcinoma A431 cells was obtained from Sigma Chemical Co (E3641). The human carcinoma A431 cell line was obtained from the American Type Culture Collection (ATCC CRL-1555). Ribi MPL+TDM adjuvant was obtained from Sigma Chemical Co (M-6536).

Immunization. Two SC20/KCo5 cross-bred mice (ID#'s 22232, and 22239) were each immunized by intra-peritoneal (i.p.) injection of $10^7$ washed whole human carcinoma A431 cells. This immunization procedure was repeated a month later in both mice. At month 4, Mouse 22239 was immunized with 25 μg of soluble EGFR in MPL+TDM adjuvant i.p.; rested eleven days and then injected with 10 μg EGFR in PBS i.v. plus 10 μg EGFR in MPL+TDM adjuvant i.p. Two days later mouse 22239 received another 10 μg EGFR in PBS i.v., and the following day splenocytes from mouse 22239 harvested for fusion. Following the first two injections with A431 cells, mouse 22232 was rested for three months and then injected i.p with 107 A431 cells mixed with MPL+TDM adjuvant. Four days later spleen cells were harvested from mouse 22232 for fusion.

Fusion. Spleen cells from mice #22232, and 22239 were fused, in two separate experiments, with either the P3 X63 Ag8.6.53 (ATCC CRL 1580; mouse #22239), or the SP2/0-Agl4 (ATCC CRL 1581; mouse #22232) myeloma cell lines. Fusions were done by standard procedures outlined in example 8.

Hybridoma Screening. Screening procedures for EGFR hybridomas were similar to those used for the CTLA-4 in Example 8. ELISA plates (Nunc MaxiSorp) were coated overnight with 100 μl per well of soluble EGFR antigen at 1 μg/ml in PBS. Plates were washed and blocked with 100 μl/well PBS-Tween containing 1% BSA. Fifty μl of cell culture supernatant was added followed by a 1–2 hour incubation. Plates were washed and then incubated for one hour with 100 μl/well goat anti-human gamma heavy chain conjugated to alkaline phosphatase (Anti-human gamma (fc) AP Jackson # 109-056-098). Plates were washed three times in PBS-Tween between each step. Five and two hybridomas secreting human IgGic anti-EGFR specific antibodies were subcloned from the mouse 22232 and the mouse 22239 fusions respectively. Isotype analysis of the heavy and light chains of the EGFR specific antibodies included four $IgG_{1\kappa}$, one $IgG_{2\kappa}$ and one $IgG_{4\kappa}$ antibodies.

Example 10

Rate and Equilibrium Constants for Purified Human IgGκ Monoclonal Antibodies The hybridomas were cultured in eRDF containing 1% Fetal Bovine Serum (low-IgG). Human MAbs were purified using Protein G column. The rate equilibrium association constants of the purified MAbs for G-CSF and soluble CD4 were determined using BIAcore2000 instrument. Human G-CSF (120 RU) or CD4:Fc (1600 RU) was immobilized by covalent coupling through amine groups to the sensor chip surface of a BIAcore2000 (BIAcore) according to manufacture's instructions. The monoclonal antibody was flowed over the antigens. The chip was regenerated with Glycine-HCl buffer (PHl.5) or 4M $MgCl_2$ to remove any residual anti-human G-CSF MAb or anti-CD4 MAb, respectively. This cycle was repeated, using different concentration of MAb. The binding to and dissociation from antigen were determined using BIAevaluation 3.0 software. The Ka was derived by dividing the $k_{assoc}$ by the $k_{dissoc}$. As shown in Table 6 below, these values are comparable to those obtained for the murine anti-human G-CSF MAb, clone 3316.111 (R&D), or murine anti-CD4 MAb, Leu3a (Pharmingen)

TABLE 6

Rate and Equilibrium Constants for Purified Human IgGK MAbs

| MAb | Subclass | Mouse | Antigen | $k_{assoc}(M^{-1}s^{-1})$ | $K_{dissoc}(s^{-1})$ | $K_a(M^{-1})$ |
|---|---|---|---|---|---|---|
| #4 | $IgG_1$ | Double-Tc/KO | G-CSF | $4.1 \times 10^5$ | $3.1 \times 10^{-4}$ | $1.3 \times 10^9$ |
| #5 | $IgG_1$ | Double-Tc/KO | G-CSF | $5.9 \times 10^6$ | $5.8 \times 10^{-4}$ | $1.0 \times 10^{10}$ |
| #11 | $IgG_4$ | Cross-bred | G-CSF | $4.0 \times 10^6$ | $1.5 \times 10^{-3}$ | $2.8 \times 10^9$ |
| #21 | $IgG_1$ | Cross-bred | G-CSF | $1.1 \times 10^6$ | $2.0 \times 10^{-3}$ | $5.4 \times 10^8$ |
| #27 | $IgG_2$ | Cross-bred | G-CSF | $1.3 \times 10^6$ | $1.9 \times 10^{-3}$ | $6.5 \times 10^8$ |
| #23 | $IgG_1$ | Cross-bred | CD4 | $7.6 \times 10^5$ | $5.7 \times 10^{-5}$ | $1.3 \times 10^{10}$ |
| 3316.111 | Mouse | Wild-type | G-CSF | $1.5 \times 10^6$ | $2.3 \times 10^{-4}$ | $6.3 \times 10^9$ |
| Leu3a | Mouse | Wild-type | CD4 | $2.2 \times 10^5$ | $7.1 \times 10^{-6}$ | $3.1 \times 10^{10}$ |

Example 11

Generation of Cross-bred(Fc) Mice

It is well known that immunological tolerance avoids reactivity against self-antigens, usually preventing the production of mouse monoclonal antibodies against foreign antigens whose amino acid sequences are similar or identical to those of murine counterparts. Mouse monoclonals that bind to common epitopes between human antigens and their murine counterparts can be useful because the amino acid sequences in the active site of protein antigens tend to be well-conserved. In addition, any effect brought about by the in vivo administration of these antibodies can be easily studied in mouse models. However, it has also been difficult to obtain mouse monoclonal antibodies against such common epitopes. As described above, the cross-bred mice of the present invention can be used for obtaining human monoclonal antibodies against various human antigens. However, in certain circumstances it can be difficult to obtain human monoclonals that have the ability to bind to well-conserved human antigens or that cross-react with murine counterparts. Thus, in another aspect of the invention, additional cross-bred mice of the invention are provided in which an Fcγ receptor IIB has been inactivated. These mice, referred to herein as cross-bred(Fc) mice, allow for the generation of monoclonal antibodies that bind to well-conserved antigens or that cross-react with their murine counterparts. Biochemical and genetic studies indicate that the type IIB low-affinity receptor for immunoglobulin (Ig)G (FcγRIIB) inhibits cellular activation triggered through antibody or immune complexes and may be an important component in preventing the emergence of autoimmunity (Takai, T. et al., 1996, *Nature* 379:346–349). Animals deficient in the FcγRIIB, the inhibitory Fc receptor, have generalized enhanced antibody responses and heightened inflammation in all antibody-mediated classes of hyper sensitivity reactions (Takai, T. et al., 1996, *Nature* 379:346–349). For example, the mutant mice immunized with bovine collagen type IV (C-IV), but not wild-type mice, showed elevated autoantibody responses to mouse C-IV (Nakamura, A. et al., 2000, *J. Exp. Med.* 191:899–905). However, there has been no report studying whether FcγRIIB mutant mice could be used for efficient production of autoreactive monoclonal antibodies. Moreover, there has been no report demonstrating efficient production of human monoclonals that bind to both human antigens and murine counterparts in mice.

As described below, the FcγRIIB mutation was bred into cross-bred mice of the invention. Immunization of the resultant cross-bred(Fc) mice with bovine C-IV elicited in human antibody responses against both bovine and murine C-IV. Hybridomas secreting human monoclonals that bind to both bovine and murine C-Iv can also be generated. Therefore, the cross-bred(Fc) mice allow for the production of human monoclonals that can bind both immunized foreign antigens and their murine counterparts. The cross-bred (Fc) mice can also be useful for obtaining human monoclonal antibodies against well-conserved antigens. Mice homozygous for the FcγRIIB-knockout (Fc(−/−)) (Takai, T. et al., 1996, *Nature* 379:346–349) were provided by Dr. Toshifumi Takai (Tohoku University, JAPAN). The Fc(−/−) male mice were mated with female cross-bred mice (as described in Example 3). The retention of the KCo5 transgene and hCF(SC20) in each F1 individual was examined by ELISAs and PCRs as described in Example 3. Genotypes of FcγRIIB-knockout were determined by PCR analysis using the three primers as follows:

```
neo,  5'-CTCGTGCTTTACGGTATCGCC    (SEQ ID NO:8);
5'EC1, 5'-AAACTCGACCCCCCGTGGATC   (SEQ ID NO:9);
                                  and
3'EC1, 5'-TTGACTGTGGCCTTAAACGTGTAG (SEQ ID NO:10).
```

Genomic DNA samples prepared from tail biopsy were subjected to PCR using AmpliTaq DNA polymerase (Perkin Elmer). In the standard reaction mixture containing the above three primers (0.5 pM each) the samples were amplified for 35 cycles: 30 sec at 94° C., sec at 62° C., 30 sec at 72° C. (Gene Amp PCR system 9600, Perkin Elmer). The band size given by wild-type allele and homozygous allele are 161 bp and 232 bp, respectively. The F1 male whose genotype is KCo5/CMD or CM2D (−/+)/CKD or JKD (−/+)/Fc (−/+) and female whose genotype is hCF(SC20)/KCo5/CMD or CM2D (−/+)/CKD or JKD (−/+)/Fc (−/+) were selected and used for further breeding. Finally, mice (cross-bred (Fc)) whose genotype is hCF(SC20)/KCo5/CMD or CM2D (−/−)/CKD or JKD (−/−)/Fc (−/−) were obtained. The serum expression levels of human Ig μ, and κ in the cross-bred(Fc) mice were confirmed to be comparable to those in cross-bred mice (see Example 4)

Example 12

Generation of Anti-mouse Type IV Collagen Human Monoclonal Antibodies

Immunization of antigen. Bovine C-IV (Cellmatrix IV) was obtained from Nitta Gellatin, Inc. The C-IV solution (3.0 mg/ml in 1 mM HCl, pH 3.0) was neutralized by adding 1 mM NaOH (final concentration) before emulsifying with Freund's adjuvant. Cross-bred mice and cross-bred(FC) mice were immunized at the tail base with 150 μg of C-IV emulsified in CFA containing *Mycobacterium tuberculosis* strain $H_{37}Rv$ (Wako Pure Chemical Industries, Ltd.). The mice were boosted at the same location with 150 μg of C-IV plus IFA (Wako Pure Chemical Industries, Ltd.) 26, and 48 days later (Nakamura, A. et al., 2000, *J. Exp. Med.* 191: 899–905).

Figure 14:
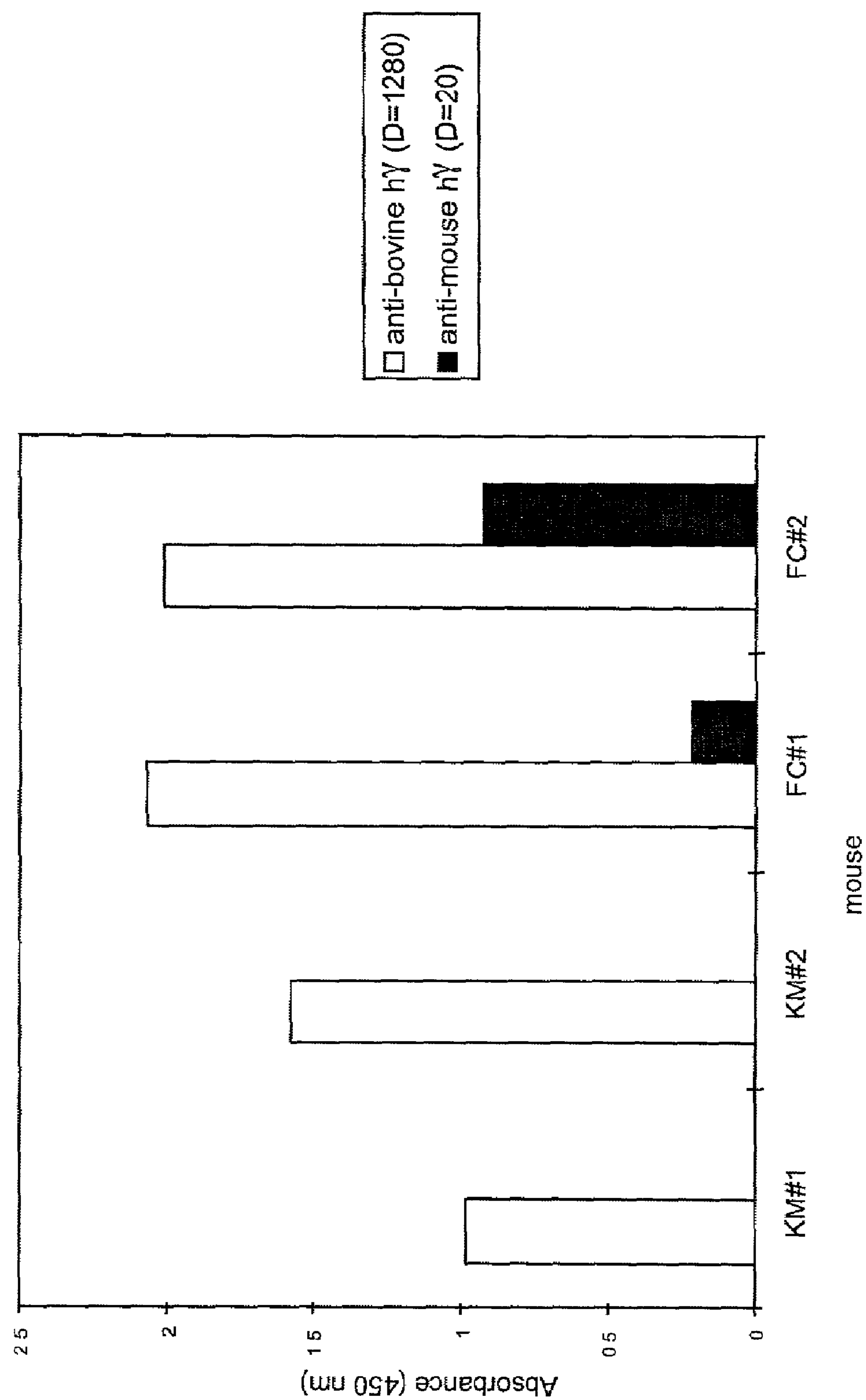
FIG. 14. Enhanced responses to bovine C-IV in the serum of cross-bred(Fc) mice.

Humoral Responses in mice. Serum was collected on days 58. Antigen reactive human Igγ in the serum were measured by ELISA as described with modification (Nakamura, A. et al., 2000, *J. Exp. Med.* 191:899–905). Antibodies to bovine C-IV were detected in a 96-well microplate assay (Nunc, MaxiSorp) in which wells were coated with 50 μl/well of a 20 μg/ml solution of bovine C-IV in PBS at 4 degree overnight. Antibodies to mouse C-IV were detected by the use of the BIOCOAT cellware mouse C-IV 96 well plate assay (Becton Dickinson Labware). The diluted serum (1:20–1280) was added at 50 μl/well and allowed to react overnight at 4 degree. The wells were washed and goat anti-human IgG (Fc) coupled to horseradish peroxydase (Sigma, A0170) at 4 degree for 2 hours, washed and developed at room temperature for 30 min with 50 μl of TMB substrate (Sumitomo Bakelite, ML-1120T). The OD at 450 nm was read using a micro-plate reader (Arvo, Wallac Berthold Japan). Specific human γ auto-antibody response to mouse C-IV were observed in the serum of cross-bred(Fc), but not cross-bred mice. Enhanced responses to bovine C-IV were observed in the serum of cross-bred(Fc) mice (FIG. 14).

Fusion and Hybridoma Screening. The mice were given an additional intraperitoneal (KM#1: cross-bred, FC#1: cross-bred(Fc)) or intravenous (KM#2: cross-bred, FC#2: cross-bred(Fc)) injections of 150 μg of antigen 66 days later and spleen cells were harvested 69 days later. Spleen cells from mice were fused with mouse myeloma cells (Sp2/0-Ag14) by standard procedures. The cell suspension were inoculated into 96-well plates at 200 thousands of splenocytes per well. Cells were cultured in DMEM, 10% FBS, Insulin, IL-6. HAT or HT supplement was added to the medium during initial growth and selection. The hybridomas were screened by ELISA. To identify hybridomas secreting mouse C-IV, ELISA plates (Nunc MaxiSorp) were coated overnight at 4 degree with 50 μl/well mouse C-IV (Sigma, C0534) at 40 μg/ml in PBS. Fifty μl of cell culture supernatant was added. Two hybridomas secreted hγ positive, mouse C-IV reactive antibody were obtained from a cross-bred(Fc) mice and were successfully subcloned by limiting dilution (see Table 7 below).

TABLE 7

Production of anti-collagen type IV monoclonal antibodies

| | Positive Wells | | |
|---|---|---|---|
| Mouse ID # | anti-bovine h( | anti-mouse h( | |
| KM#1 | 8 | 0 | ip |
| KM#1 | 52 | 0 | iv |
| FC#1 | 16 | 0 | ip |
| FC#2 | 85 | 2 | iv |

This data shows that the cross-bred(Fc) mice are useful for production of human monoclonal antibodies against well-conserved antigens or epitopes.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications and patent documents cited above are hereby incorporated by reference in their entirety for all purposes to the same extent as if each were so individually denoted.

What is claimed is:

1. A transgenic mouse comprising two human immunoglobulin loci, wherein one of said human immunoglobulin loci is a human heavy chain locus and the other locus is a human light chain locus; wherein the human heavy chain locus is carried by transchromosome SC20 and the human light chain locus is carried by a transgene integrated into the genome of said mouse; and wherein an endogenous mouse heavy chain locus and at least one endogenous mouse light chain locus are inactivated.

2. The transgenic mouse of claim 1, wherein the endogenous mouse heavy chain locus and the endogenous mouse kappa light chain locus are inactivated.

3. The transgenic mouse of claim 1, wherein at least a part of the human light chain locus is cloned into a YAC vector.

4. The transgenic mouse of claim 1, wherein the transgene is the KCo5 transgene.

* * * * *